US009993462B2

(12) United States Patent
Noda et al.

(10) Patent No.: US 9,993,462 B2
(45) Date of Patent: *Jun. 12, 2018

(54) HYDANTOIN DERIVATIVE-CONTAINING PHARMACEUTICAL COMPOSITION

(71) Applicant: Chugai Seiyaku Kabushiki Kaisha, Kita-ku, Tokyo (JP)

(72) Inventors: Hiroshi Noda, Shizuoka (JP); Hidetomo Kitamura, Shizuoka (JP); Tatsuya Tamura, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/317,221

(22) PCT Filed: Jun. 9, 2014

(86) PCT No.: PCT/JP2014/065262
§ 371 (c)(1),
(2) Date: Dec. 8, 2016

(87) PCT Pub. No.: WO2015/189901
PCT Pub. Date: Dec. 17, 2015

(65) Prior Publication Data
US 2017/0112812 A1 Apr. 27, 2017

(51) Int. Cl.
*A61K 31/435* (2006.01)
(52) U.S. Cl.
CPC .................................. *A61K 31/435* (2013.01)
(58) Field of Classification Search
None
See application file for complete search history.

(56) References Cited

U.S. PATENT DOCUMENTS 7,666,892 B2 2/2010 Eriksson et al.
7,981,904 B2 7/2011 Chang et al.
(Continued)

FOREIGN PATENT DOCUMENTS

CN  1516587 A   7/2004
EA  005762 B1   8/2003
(Continued)

OTHER PUBLICATIONS

Database CAPLUS Chemical Abstracts Service, Columbus, Ohio, US; Database Accession No. 2014:998822, Abstract of WO 2014092061 Chugai Seiyaku Kabushiki Kaisha, Japan, Nishimura et al., Jun. 19, 2014.*

(Continued)

*Primary Examiner* — Karl J Puttlitz
(74) *Attorney, Agent, or Firm* — Foley & Lardner LLP

(57) ABSTRACT

The present invention provides pharmaceutical compositions for inducing bone and/or cartilage anabolism, which comprises as an active ingredient a compound represented by formula (1) below and a pharmacologically acceptable salt thereof:

(1)

wherein $R_1$, $R_2$, $R_3$, and $R_4$ are as defined in the claims.

11 Claims, 9 Drawing Sheets

(56) References Cited

U.S. PATENT DOCUMENTS

| | | | |
|---|---|---|---|
| 8,476,286 | B2 | 7/2013 | Beerli et al. |
| 8,513,193 | B2 | 8/2013 | Rosier et al. |
| 9,169,254 | B2 | 10/2015 | Esaki et al. |
| 9,428,505 | B2 * | 8/2016 | Nishimura ........... C07D 519/00 |
| 9,487,517 | B2 | 11/2016 | Esaki et al. |
| 2005/0101574 | A1 | 5/2005 | Ishizuka et al. |
| 2007/0099940 | A1 | 5/2007 | Spearing |
| 2007/0123548 | A1 | 5/2007 | Cowan et al. |
| 2016/0326175 | A1 | 11/2016 | Nishimura et al. |

FOREIGN PATENT DOCUMENTS

| | | | |
|---|---|---|---|
| EP | 1321141 A1 | | 6/2003 |
| JP | 11-035470 A | | 2/1999 |
| JP | 2004-523583 A | | 8/2004 |
| JP | 2005-502605 A | | 1/2005 |
| JP | 2007-522214 A | | 8/2007 |
| JP | 2007-522215 A | | 8/2007 |
| JP | 2008-515895 A | | 5/2008 |
| WO | WO 00/35885 A1 | | 6/2000 |
| WO | WO 02/017911 A1 | | 3/2002 |
| WO | WO 02/34753 A2 | | 5/2002 |
| WO | WO 02/074751 A1 | | 9/2002 |
| WO | WO 02/102782 A2 | | 12/2002 |
| WO | WO 2005/077918 A1 | | 8/2005 |
| WO | WO 2005/077959 A1 | | 8/2005 |
| WO | WO 2006/041830 A2 | | 4/2006 |
| WO | WO 2007/135417 A1 | | 11/2007 |
| WO | WO 2007/149873 A2 | | 12/2007 |
| WO | WO 2008/148689 A1 | | 12/2008 |
| WO | WO 2009/074575 A2 | | 6/2009 |
| WO | WO 2010/045229 A2 | | 4/2010 |
| WO | WO 2010/126030 A1 | | 11/2010 |
| WO | 2014092061 | * | 6/2014 |
| WO | WO 2014/092061 A1 | | 6/2014 |

OTHER PUBLICATIONS

Abou-Samra et al., "Expression cloning of a common receptor for parathyroid hormone and parathyroid hormone-related peptide from rat osteoblast-like cells: A single receptor stimulates intracellular accumulation of both cAMP and inositol trisphosphates and increases intracellular free calcium," Proc. Nat. Acad. Sci. USA, Apr. 1992, 89(7):2732-2736.

Berenbaum, F., "Osteoarthritis as an inflammatory disease (osteoarthritis is not osteoarthrosis!)," Osteoarthritis and Cartilage, 2013, 21:16-21.

Bergwitz et al., "Full Activation of Chimeric Receptors by Hybrids between Parathyroid Hormone and Calcitonin," J. Biol. Chem., Oct. 25, 1996, 271(43):26469-26472.

Bingham et al., "Risedronate Decreases Biochemical Markers of Cartilage Degradation but Does Not Decrease Symptoms or Slow Radiographic Progression in Patients with Medial Compartment Osteoarthritis of the Knee," Nov. 2006, 54(11):3494-3507.

Bleicher et al., "Parallel solution- and solid-phase synthesis of spirohydantoin derivatives as neurokinin-1 receptor ligands," CAplus, Chemical Abstracts, Mar. 24, 2003, 138(12):138:170128h.

Bringhurst et al., "Cloned, Stably Expressed Parathyroid Hormone (PTH)/PTH-Related Peptide Receptors Activate Multiple Messenger Signals and Biological Responses in LLC-PK$_1$ Kidney Cells," Endocrinology, May 1993, 132(5):2090-2098.

Broadus et al., "Parathyroid Hormone-Related Protein," The Parathyroids, J.P. Bilezikian et al., Eds., 1994, Chapter 17, 259-294.

CPMP/EWP/784/97 Rev. 1, Jan. 20, 2010, Committee for Medicinal Products for Human Use (CHMP), European Medicines Agency, 14 pages.

Cross et al., Cerebrovasodilatation through selective inhibition of the enzymes carbonic Anhydrase, 1978.

Dörwald, Florencio Z., Side Reactions in Organic Synthesis, 2005, Wiley: VCH, Weinheim, p. IX of Preface.

Fosang et al., "Identifying the human aggrecanase," Osteoarthritis and Cartilage, 2010, 18:1109-1116.

Greenspan et al., "Effect of Recombinant Human Parathyroid Hormone (1-84) on Vertebral Fracture and Bone Mineral Density in Postmenopausal Women with Osteoporosis," Annals of Internal Medicine, Mar. 6, 2007, 146(5):326-339.

Hiligsmann et al., "Health economics in the field of osteoarthritis: An Expert's consensus paper from the European Society for Clinical and Economic Aspects of Osteoporosis and Osteoarthritis (ESCEO)," Seminars in Arthritis and Rheumatism, 2013, 43:303-313.

Hoare, Sam R.J., "Mechanisms of peptide and nonpeptide ligand binding to Class B G-protein-coupled receptors," Drug Discovery Today, Mar. 15, 2005, 10(6):417-427.

Ishihara et al., "Molecular cloning and expression of a cDNA encoding the secretin receptor," The EMBO Journal, Jul. 1991, 10(7):1635-1641.

Jelinek et al., "Expression Cloning and Signaling Properties of the Rat Glucagon Receptor," Science, Mar. 12, 1993, 259(5101):1614-1616.

Kamekura et al., "Contribution of Runt-Related Transcription Factor 2 to the Pathogenesis of Osteoarthritis in Mice After Induction of Knee Joint Instability," Arthritis & Rheumatism, Aug. 2006, 54(8):2462-2470.

Karaplis et al., "Letah skeletal dysplasia from targeted disruption of the parathyroid hormone-related peptide gene," Genes & Development, Feb. 1, 1994, 8(3):277-289.

Karsdal et al., "Lessons Learned From the Development of Oral Calcitonin: The First Tablet Formulation of a Protein in Phase III Clinical Trials," J. Clin. Pharmacol., 2011, 51:460-471.

Kolakowski, Lee F., Jr., "GCRDb: A G-Protein-Coupled Receptor Database," Receptors and Channels, 1994, 2(1):1-7.

Kronenberg et al.,. "Parathyroid Hormone: Biosynthesis, Secretion, Chemistry, and Action," Handbook of Experimental Pharmacology: Physiology and Pharmacology of Bone, 1993, 507-567.

Lanske et al., "PTH/PTHrP Receptor in Early Development and Indian Hedgehog-Regulated Bone Growth," Science, Aug. 2, 1996, 273(5275):663-666.

Lin et al., "Expression Cloning of an Adenylate Cyclase-Coupled Calcitonin Receptor," Science, Nov. 15, 1991, 254(5034):1022-1024.

Lin et al., "Modulating hedgehog signaling can attenuate the severity of osteoarthritis," Nature Medicine, Dec. 2009, 15(12):1421-1425.

Mittal et al., "Newer anabolic therapies in osteoporosis," Indian J. Endocrinol. Metab., Dec. 2012, 16(Supp2):S279-S281.

Neer et al., "Effect of Parathyroid Hormone (1-34) on Fractures and Bone Mineral Density in Postmenopausal Women with Osteoporosis," New England Journal of Medicine, May 10, 2001, 344(19):1434-1441.

Non-Final Office Action dated Aug. 11, 2016, in U.S. Appl. No. 15/214,729.

Patani et al., 1996, Bioisoterism.

Reginster et al., "Efficacy and safety of strontium ranelate in the treatment of knee osteoarthritis: results of a double-blind, randomised placebo-controlled trial," Ann. Rheum. Dis., 2013, 72:179-186.

Rejnmark et al., "PTH replacement therapy of hypoparathyroidism," Osteoporos. Int., May 2013, epub Nov. 27, 2012, 24:1529-1536.

Rickard et al., "Intermittent treatment with parathyroid hormone (PTH) as well as a non-peptide small molecule agonist of the PTH1 receptor inhibits adipocyte differentiation in human bone marrow stromal cells," Bone, Dec. 2006, epub Aug. 10, 2006, 39(6):1361-1372.

Sampson et al., "Teriparatide as a Chondroregenerative Therapy for Injury-Induced Osteoarthritis," Science Translational Medicine, Sep. 21, 2011, 3(101:101ra93:1-12.

Tashjian et al.,. "Perspective: Teriparatide [Human PTH(1-34)]: 2.5 Years of Experience on the Use and Safety of the Drug for the Treatment of Osteoporosis," Journal of Bone and Mineral Research, Mar. 2006, 21(3):354-365, Epub Nov. 11, 2005.

(56) References Cited

OTHER PUBLICATIONS

Urena et al., "Regulation of Parathyroid Hormone (PTH)/PTH-Related Peptide Receptor Messenger Ribonucleic Acid by Glucocorticoids and PTH in ROS 17/2.8 and OK Cells," Endocrinology, Jan. 1994, 134(1):451-456.
Usdin et al., "Identification and Functional Expression of a Receptor Selectively Recognizing Parathyroid Hormone, the PTH2 Receptor," J. Biol. Chem., Jun. 30, 1995, 270(26):15455-15458.
Winer et al., "Long-Term Treatment of Hypoparathyroidism: A Randomized Controlled Study Comparing Parathyroid Hormone-(1-34) Versus Calcitriol and Calcium," The Journal of Clinical Endocrinology & Metabolism, Sep. 2003, 88(9):4214-4220.
Office Action dated Sep. 28, 2015, in U.S. Appl. No. 14/426,408.
Final Office Action dated Mar. 3, 2016, in U.S. Appl. No. 14/426,408.
Office Action dated Aug. 11, 2016, in U.S. Appl. No. 15/214,729.
Final Office Action dated Mar. 20, 2017, in U.S. Appl. No. 15/214,729.
U.S. Appl. No. 15/548,267, filed Dec. 20, 2017, Yoshikazu et al.

\* cited by examiner

Vehicle (50% DMSO/physiological saline solution)

Low-dose Compound 7 (6.5 μg/day)

High-dose Compound 7 (65 μg/day)

HYDANTOIN DERIVATIVE-CONTAINING PHARMACEUTICAL COMPOSITION

CROSS-REFERENCE TO RELATED APPLICATIONS

This application is a National Stage application of PCT/JP2014/065262, filed Jun. 9, 2014.

TECHNICAL FIELD

The present invention relates to pharmaceutical preparations which contain as an active ingredient, a hydantoin derivative that has high metabolic stability and exhibits strong PTH-like effects, and provides pharmaceuticals that induce bone and/or cartilage anabolism for preventing, treating, and facilitating the recovery and healing for osteoporosis, decrease of bone mass in periodontal disease, alveolar bone defect after tooth extraction, osteoarthritis, articular cartilage deficiency, adynamic bone disease, achondroplasia, hypochondroplasia, osteomalacia, bone fracture, and such.

BACKGROUND ART

Parathyroid hormone (PTH) is known as a hormone that acts on target cells in the kidney and bone to regulate calcium (Ca) and phosphorus (Pi) homeostasis (Non-Patent Document 1). Serum Ca concentration level is maintained by PTH mainly through direct or indirect actions on the gastrointestinal tract, bone, and kidney. PTH promotes resorption of Ca from the renal tubules and thereby suppresses excretion of Ca in the body to the outside. It also increases the synthesis of an enzyme that converts vitamin D to active vitamin D in the kidney, and thereby contributes to the facilitation of active vitamin D-mediated Ca absorption from the gastrointestinal tract. Furthermore, PTH enhances the differentiation of osteoclasts indirectly via osteoblasts and promote Ca release from the bone. These actions of PTH are thought to occur mainly via the cyclic adenosine 3',5'-monophosphate (cAMP) elevation and/or phospholipase C (PLC) activation that occurs when PTH binds to the PTH1R.

In humans, PTH preparations [PTH (1-34) and PTH (1-84)] have a powerful bone anabolic effect, and induce significant increases in bone mineral density (BMD) and bone strength. Currently, most of the osteoporosis drugs available for humans are inhibitors of bone resorption, and the only type of drug with the bone anabolic effect that, e.g., actively increases BMD is PTH preparations. Thus, PTH preparation is regarded as one of the most effective treatments for osteoporosis (Non-Patent Document 2); however, since it is a peptide, it needs to be administered by an invasive method. Therefore, there is an expectation for production of a pharmaceutical agent that has PTH-like effects and which can be administered non-invasively.

Osteoarthritis is a degenerative disease characterized by degeneration and destruction of cartilage in the joints of the entire body such as knees, hip joints, spine, fingers; synovitis; hardening of the subchondral bone; or joint dysfunction due to osteophyte formation and chronic pain. Forty percent or more of the population aged 65 and older are said to be affected by osteoarthritis, and this has become a huge burden on medical economics (Non-Patent Documents 3 and 4). The causes of osteoarthritis include physically excessive weight load on articular cartilage, inflammation of the synovial membrane and bone marrow, genetic predisposition of the cartilage matrix components, and enhancement of bone metabolism of the subchondral bone; however, there are no therapeutic agents that suppress the degeneration and destruction of articular cartilage, and medical needs remain high.

Aggrecanases (ADAMTS-4, ADAMTS-5, etc.), matrix metalloproteases (MMP-3, MMP-9, MMP-13, etc.; Non-Patent Document 5), and inflammatory cytokines (IL-1, IL-6, etc.; Non-Patent Document 6), which are involved in destruction of the cartilage matrix, have been receiving attention as targets for therapeutic agents, but such agents have not been put to practical use. On the other hand, clinical trials have been carried out for pharmaceutical agents targeting enhancement of metabolic turnover of the subchondral bone (risedronate, calcitonin; Non-Patent Documents 7 and 8); however, degeneration and destruction of articular cartilage could not be suppressed. Furthermore, effects of suppressing destruction of articular cartilage in addition to this mechanism have been demonstrated in clinical trials of strontium ranelate which has the combined effects of promoting bone formation as well as promoting cartilage formation (Non-Patent Document 9); however, it has not reached the stage of practical use.

On the other hand, transformation of articular cartilage from permanent cartilage to calcified cartilage in pathogenesis of osteoarthritis has been reported in recent studies, and its suppression has come to draw attention as a target for therapeutic agents (Non-Patent Document 10). Pharmaceutical agents with multiple modes for suppressing terminal differentiation of articular chondrocytes based on this mechanism of action have been reported to suppress degeneration and destruction of articular cartilage in osteoarthritis model animals, which suggests a possibility of putting therapeutic agents based on this mechanism into practical use (Non-Patent Documents 11 and 12).

Under such circumstances, the present inventors submitted a patent application in advance based on their discovery that the compound represented by formula (A):

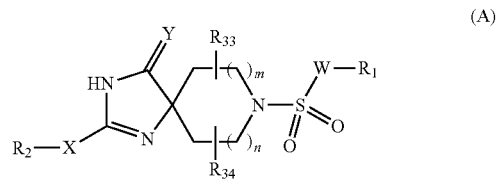

(A)

[Patent Document 1 may be referred to for W, X, Y, m, n, $R_1$, $R_2$, $R_{33}$, and $R_{34}$ in the formula] and pharmacologically acceptable salts thereof are useful as compounds having PTH-like effects, or more preferably, as a PTH1R agonist, and are useful for prevention and/or treatment of osteoporosis, fracture, osteomalacia, arthritis, thrombocytopenia, hypoparathyroidism, hyperphosphatemia, or tumoral calcinosis, or stem cell mobilization (Patent Document 1).

To produce pharmaceutical agents that have high clinical value and can be administered non-invasively, it is necessary to consider the in vivo kinetics such as absorption, distribution, metabolism, and excretion of the drug in addition to its direct actions on the target. For this purpose, it is desirable to have a pharmaceutical agent having PTH-like effects which are high metabolic stability against human liver microsomes and strong human PTH1R-mediated ability of producing cAMP.

PRIOR ART DOCUMENTS

Patent Documents

[Patent document 1] WO 2010/126030

Non-Patent Documents

[Non-patent document 1] Kronenberg, H. M., et al., In Handbook of Experimental Pharmacology, Mundy, G. R., and Martin, T. J., (eds), pp. 185-201, Springer-Verlag, Heidelberg (1993)
[Non-patent document 2] Tashjian and Gagel, J. Bone Miner. Res. 21:354-365 (2006)
[Non-patent document 3] Sem Arth Rheumatism 2013; 43: 303-13
[Non-patent document 4] CPMP/EWP/784/97 Rev. 1. 2010, European Medicines Agency
[Non-patent document 5] Osteoarth Cart 2010; 18: 1109-1116
[Non-patent document 6] Osteoarth Cart 2013; 21: 16-21
[Non-patent document 7] Arthritis Rheum. 2006; 54(11): 3494-507
[Non-patent document 8] J Clin Pharmacol. 2011; 51(4): 460-71
[Non-patent document 9] Ann Rheum Dis. 2013 February; 72(2):179-86
[Non-patent document 10] Arth Rheum 2006; 54(8): 2462-2470
[Non-patent document 11] Nat Med 2009; 15(12): 1421-1426
[Non-patent document 12] Sci Trans Med 2011; 3: 101ra93

SUMMARY OF THE INVENTION

Problems to be Solved by the Invention

An objective of the present invention is to provide methods for preventing, treating, and facilitating the recovery and healing of osteoporosis, decrease of bone mass in periodontal disease, alveolar bone defect after tooth extraction, osteoarthritis, articular cartilage deficiency, adynamic bone disease, achondroplasia, hypochondroplasia, osteomalacia, bone fracture, and such, by inducing bone/cartilage anabolism by non-invasive systemic exposure or local exposure to hydantoin derivatives having high metabolic stability and exhibiting strong PTH-like effects.

Means for Solving the Problems

Under such circumstances, the present inventors have discovered with further research that the newly found hydantoin derivatives of the present invention show a strong cAMP-producing ability in cells forced to express human PTH1R and is highly stable against metabolism in human liver microsomes. Furthermore, by administering compounds of the present invention, the present inventors discovered that they induce cartilage and/or bone anabolism, and are useful as pharmaceutical compositions for preventing, treating, and facilitating recovery and healing for osteoporosis, decrease of bone mass in periodontal disease, alveolar bone defect after tooth extraction, osteoarthritis, articular cartilage deficiency, adynamic bone disease, achondroplasia, hypochondroplasia, osteomalacia, bone fracture, and such.

The present invention relates to the following:

[1] A pharmaceutical composition for inducing bone and/or cartilage anabolism, which comprises as an active ingredient a compound represented by general formula (1) below or a pharmacologically acceptable salt thereof:

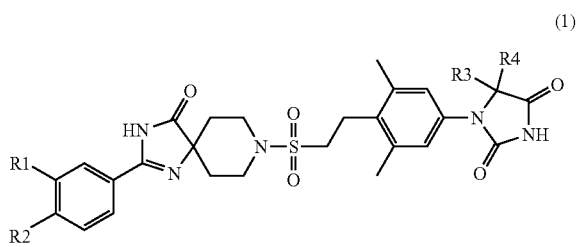

(1)

wherein,
when R1 and R2 are not both hydrogen atoms, R1 and R2 are independently:
1) hydrogen atom;
2) halogen atom;
3) an alkyl group comprising one or two carbons that may be substituted with one to five fluorine atoms; or
4) an alkoxy group comprising one or two carbons that may be substituted with one to five fluorine atoms; or R1 and R2 bond with each other to form a group represented by the formula below:

(wherein each * indicates the position of bonding with the phenyl portion); and

R3 and R4 are independently a methyl group that may be substituted with one to three fluorine atoms; or R3 and R4, together with a bound carbon atom, form a three- to six-membered carbocyclic ring (wherein, one of the carbon atoms forming the ring may be replaced with an oxygen atom, a sulfur atom, or a methyl-substituted or unsubstituted nitrogen atom).

For the compound contained as an active ingredient of a pharmaceutical composition of the present invention, a compound in which the combination of R1 and R2 is a trifluoromethyl group and a hydrogen atom, and where R3 and R4, together with a bound carbon atom, form a cyclopentyl ring, can be excluded from the above-mentioned compounds represented by formula (1).

[2] The pharmaceutical composition of [1], wherein R1 and R2 of the compound represented by general formula (1) or a pharmacologically acceptable salt thereof are selected from the combinations below:

1) R1 is a hydrogen atom or a halogen atom, and R2 is a hydrogen atom, a trifluoromethyl group, or a trifluoromethoxy group (provided that R1 and R2 are not both hydrogen atoms);
2) R1 is a trifluoromethyl group or a trifluoromethoxy group, and R2 is a hydrogen atom or a halogen atom;
3) R1 and R2 bond with each other to form a group represented by the formula below:

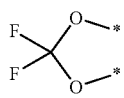

(wherein, each * indicates the position of bonding with the phenyl portion); and
R3 and R4 are methyl groups; or
R3 and R4, together with a bound carbon atom, form a ring selected from below:

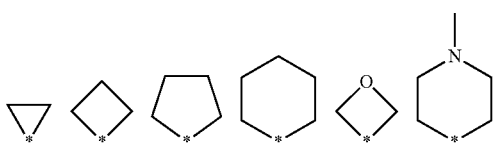

(wherein * indicates the position of bonding with the imidazolidine-2,4-dione portion).

[3] The pharmaceutical composition of [1], wherein R1 and R2 of the compound represented by general formula (1) or a pharmacologically acceptable salt thereof are selected from the combinations below:
1) R1 is a trifuloromethoxy group and R2 is a fluorine atom;
2) R1 is a bromine atom and R2 is a hydrogen atom;
3) R1 is a trifuloromethoxy group and R2 is a fluorine atom;
4) R1 is a fluorine atom and R2 is a trifluoromethoxy group;
5) R1 is a trifluoromethyl group and R2 is a hydrogen atom;
6) R1 is a hydrogen atom and R2 is a trifluoromethoxy group;
7) R1 and R2 bond with each other to form a group represented by the formula below:

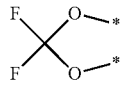

(wherein each * indicates the position of bonding with the phenyl portion); and
R3 and R4 are methyl groups; or
R3 and R4, together with a bound carbon atom, form a ring selected from below:

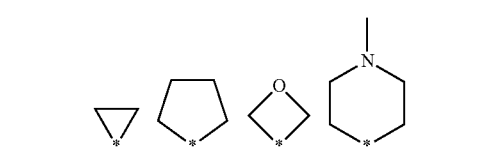

(wherein * indicates the position of bonding with the imidazolidine-2,4-dione portion).

[4] The pharmaceutical composition of [1], wherein R3 and R4 of the compound represented by general formula (1) or a pharmacologically acceptable salt thereof are methyl groups.

[5] The pharmaceutical composition of [1], wherein R3 and R4 of the compound represented by general formula (1) or a pharmacologically acceptable salt thereof, together with a bound carbon atom, form a ring selected from below:

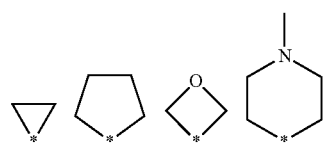

(wherein * indicates the position of bonding with the imidazolidine-2,4-dione portion).

[6] The pharmaceutical composition of [1], which comprises as an active ingredient a compound or pharmacologically acceptable salt thereof, wherein the compound is selected from the group consisting of:
1-(4-(2-((2-(4-fluoro-3-(trifluoromethoxy)phenyl)-4-oxo-1,3,8-triazaspiro[4.5]deca-1-en-8-yl)sulfonyl)ethyl)-3,5-dimethylphenyl)-5,5-dimethylimidazolidine-2,4-dione;
1-(4-(2-((2-(3-bromophenyl)-4-oxo-1,3,8-triazaspiro[4.5]deca-1-en-8-yl)sulfonyl)ethyl)-3,5-dimethylphenyl)-5,5-dimethylimidazolidine-2,4-dione;
1-(4-(2-((2-(4-fluoro-3-(trifluoromethyl)phenyl)-4-oxo-1,3,8-triazaspiro[4.5]deca-1-en-8-yl)sulfonyl)ethyl)-3,5-dimethylphenyl)-5,5-dimethylimidazolidine-2,4-dione;
1-(4-(2-((2-(3-fluoro-4-(trifluoromethoxy)phenyl)-4-oxo-1,3,8-triazaspiro[4.5]deca-1-en-8-yl)sulfonyl)ethyl)-3,5-dimethylphenyl)-5,5-dimethylimidazolidine-2,4-dione;
1-(4-(2-((2-(2,2-difluorobenzo[d][1,3]dioxol-5-yl)-4-oxo-1,3,8-triazaspiro[4.5]deca-1-en-8-yl)sulfonyl)ethyl)-3,5-dimethylphenyl)-5,5-dimethylimidazolidine-2,4-dione;
1-(3,5-dimethyl-4-(2-((4-oxo-2-(3-(trifluoromethyl)phenyl)-1,3,8-triazaspiro[4.5]deca-1-en-8-yl) sulfonyl)ethyl)phenyl)-5,5-dimethylimidazolidine-2,4-dione;
1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-5,5-dimethylimidazolidine-2,4-dione);
1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-1,3-diazaspiro[4.4]nonane-2,4-dione;
1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-8-methyl-1,3,8-triazaspiro[4.5]decane-2,4-dione;
5-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-2-oxa-5,7-diazaspiro[3.4]octane-6,8-dione; and
4-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-4,6-diazaspiro[2.4]heptane-5,7-dione.

[7] The pharmaceutical composition of [1], wherein the compound is 1-(3,5-dimethyl-4-(2-((4-oxo-2-(3-(trifluoromethyl)phenyl)-1,3,8-triazaspiro[4.5]deca-1-en-8-yl)sulfonyl)ethyl)phenyl)-5,5-dimethylimidazolidine-2,4-dione or pharmacologically acceptable salt thereof.

[8] The pharmaceutical composition of [1], wherein the compound is 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-5,5-dimethylimidazolidine-2,4-dione or pharmacologically acceptable salt thereof.

[9] The pharmaceutical composition of [1], wherein the compound is 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-1,3-diazaspiro[4.4]nonane-2,4-dione or pharmacologically acceptable salt thereof.

[10] the pharmaceutical composition of [1] for use in preventing or treating osteoporosis, improving decrease of bone mass in periodontal disease, facilitating recovery from alveolar bone defect after tooth extraction, preventing or treating osteoarthritis, facilitating recovery from articular cartilage deficiency, preventing or treating adynamic bone disease, preventing or treating achondroplasia, preventing or treating hypochondroplasia, preventing or treating osteomalacia, or facilitating recovery from bone fracture;

[11] a method for inducing bone and/or cartilage anabolism, which comprises administering a compound of any one of [1] to [9] or a pharmaceutically acceptable salt thereof in a pharmaceutically effective amount to a patient in need of prevention or treatment of osteoporosis, improvement of decrease of bone mass in periodontal disease, facilitation of recovery from alveolar bone defect after tooth extraction, prevention or treatment of osteoarthritis, facilitation of recovery from articular cartilage deficiency, prevention or treatment of adynamic bone disease, prevention or treatment of achondroplasia, prevention or treatment of hypochondroplasia, prevention or treatment of osteomalacia, or facilitation of recovery from bone fracture;

[12] the method of [11], wherein the method for inducing bone and/or cartilage anabolism is a method for preventing or treating osteoporosis, a method for improving decrease of bone mass in periodontal disease, a method for facilitating recovery from alveolar bone defect after tooth extraction, a method for preventing or treating osteoarthritis, a method for promoting recovery from articular cartilage deficiency, a method for preventing or treating adynamic bone disease, a method for preventing or treating achondroplasia, a method for preventing or treating hypochondroplasia, a method for preventing or treating osteomalacia, or a method for facilitating recovery from bone fracture;

[13] use of a compound of any one of [1] to [9] or a pharmaceutically acceptable salt thereof for manufacturing a pharmaceutical composition for preventing or treating osteoporosis, improving decrease of bone mass in periodontal disease, promoting recovery from alveolar bone defect after tooth extraction, preventing or treating osteoarthritis, facilitating recovery from articular cartilage deficiency, preventing or treating adynamic bone disease, preventing or treating achondroplasia, preventing or treating hypochondroplasia, preventing or treating osteomalacia, or facilitating recovery from bone fracture;

[14] use of a compound of any one of [1] to [9] or a pharmaceutically acceptable salt thereof for manufacturing a pharmaceutical composition for inducing bone and/or cartilage anabolism; and

[15] the compound of any one of [1] to [9] or a pharmaceutically acceptable salt thereof to be used for preventing or treating osteoporosis, improving decrease of bone mass in periodontal disease, facilitating recovery from alveolar bone defect after tooth extraction, preventing or treating osteoarthritis, promoting recovery from articular cartilage deficiency, preventing or treating adynamic bone disease, preventing or treating achondroplasia, preventing or treating hypochondroplasia, preventing or treating osteomalacia, or facilitating recovery from bone fracture.

Furthermore, the present invention provides methods for treating pathological conditions that may be prevented, treated, and/or cured through bone and/or cartilage anabolism by administering a compound of formula (1) or a pharmaceutically acceptable salt thereof.

Effects of the Invention

The present invention enables prevention, treatment, and facilitation of recovery and/or cure of osteoporosis, decrease of bone mass in periodontal disease, alveolar bone defect after tooth extraction, osteoarthritis, articular cartilage deficiency, adynamic bone disease, achondroplasia, hypochondroplasia, osteomalacia, and bone fracture through induction of bone and/or cartilage anabolism by using hydantoin derivatives that have strong PTH-like effects and high metabolic stability.

MODE FOR CARRYING OUT THE INVENTION

Figure 1:
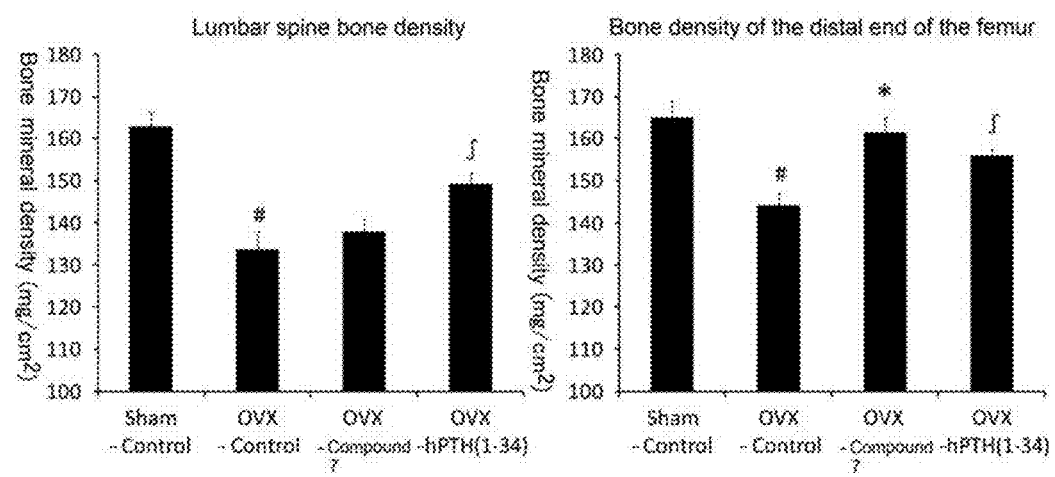
FIG. 1 shows the bone mineral density of the lumbar spine and femur in ovariectomized rats with six weeks of repeated administration. More specifically, it shows the results of bone mineral density measurements taken on the lumbar spine and femur using a dual X-ray bone mineral scanner, when a vehicle, Compound 7, or hPTH(1-34) was repeatedly administered once a day for six weeks to ovariectomized rats.

The present invention relates to hydantoin derivatives that have high metabolic stability and exhibiting strong PTH-like effects, and uses thereof. The present inventors synthesized compounds represented by the aforementioned formula (1) or pharmaceutically acceptable salts thereof, and discovered that these compounds or salts thereof induce bone and/or cartilage anabolism.

The "alkyl" herein refers to a monovalent group derived by removing any one hydrogen atom from an aliphatic hydrocarbon, and covers a subset of hydrocarbyl or hydrocarbon group structures not containing a heteroatom or an unsaturated carbon-carbon bond and containing hydrogen and carbon atoms in the backbone. Examples of the alkyl group include those of linear or branched structures. The alkyl group is preferably an alkyl group comprising one or two carbon atoms. The alkyl group is specifically, for example, a methyl group or an ethyl group, and is preferably a methyl group.

The term "alkoxy" as used herein refers to an oxy group to which the above-defined "alkyl" is bound, and preferably refers to an alkoxy group comprising one or two carbon atoms. Specific examples include methoxy and ethoxy groups, and a preferred example is methoxy group.

The "B optionally substituted with A" herein denotes that any hydrogen atom(s) in B may be substituted with any number of As.

In the present invention, the number of substituents is not limited unless otherwise indicated. For example, the number of substituents may be 1 to 5, 1 to 4, 1 to 3, 1 to 2, or 1.

The "halogen atom" herein refers to a fluorine atom, a chlorine atom, a bromine atom or an iodine atom.

Herein, the symbol "*" in the chemical formula refers to the position of bonding.

Compounds of the present invention represented by formula (1) has strong PTH-like effects and high metabolic stability.

The "PTH-like effect" herein refers to activity of generating intracellular cAMP (cAMP: cyclic adenosine monophosphate) by action on the PTH receptor or action on the signal transduction pathway through the PTH receptor.

In the present invention, whether there is a "strong PTH-like effect", or whether "a PTH-like effect is strong", or whether to "have a strong PTH-like effect" can be confirmed by measuring the cAMP signaling activity by analyzing cAMP signaling, for example, according to the method described in J. Bone. Miner. Res. 14:11-20, 1999. Specifically, for example, according to the method described in Reference Test Example 1, the amount of cAMP produced in cells forced to express human PTH1R is determined using a commercially available cAMP EIA kit (for example, Biotrack cAMP EIA system, GE health care) to measure the concentration of each compound at 20% cAMP signaling activity (EC20) or their concentration at 50% cAMP signaling activity (EC50), with the cAMP signaling activity obtained upon administration of 100 nM of human PTH (1-34) being defined as 100%. In the present invention, for a "strong PTH-like effect" or "a PTH-like effect is strong", for example, the EC20 value (µM) measured by the above-mentioned method is preferably 5.0 or less, more preferably 3.0 or less, and even more preferably 2.0 or less. For EC50, the value (µM) measured by the above-mentioned method is, for example, preferably 25.0 or less, more preferably 15.0 or less, and even more preferably 10.0 or less.

Whether there is "high metabolic stability" or whether the "metabolic stability is high" can be confirmed using a general measurement method. For example, liver cells, small intestinal cells, liver microsomes, small intestinal microsomes, liver S9, and such may be used for the confirmation. Specifically, for example, the stability of a compound in liver microsomes can be confirmed by taking measurements according to description in T. Kronbach et al. (Oxidation of midazolam and triazolam by human liver cytochrome P450IIIA4. Mol. Pharmacol, 1989, 36(1), 89-96). More specifically, the stability can be confirmed by following the method described in Reference Test Example 3. In the present invention, "high metabolic stability" or "metabolic stability is high" are when the clearance (4/min/mg) value in the metabolic stability test using human liver microsomes described in the above-mentioned Reference Test Example is preferably 60 or less, more preferably 40 or less, and even more preferably 35 or less. Specifically, high metabolic stability can be obtained in the aforementioned formula (1), except where the combination of R1 and R2 is a trifluoromethyl group and a hydrogen atom, and R3 and R4, together with a bound carbon atom, form a cyclopentyl ring.

Whether "bone and/or cartilage anabolism is induced" can be confirmed using known methods.

Induction of bone anabolism can be confirmed, for example, by continuously administering a test compound for a certain period, and then measuring the bone mineral density or bone mass using a general measurement method, and then comparing it with a control. Specifically, for example, bone mineral density measurements can be taken using a dual X-ray bone mineral scanner [for example, DCS-600EX (Aloka)] by following the method described in the document by Takeda et al. (Bone 2013; 53(1):167-173). If bone mineral density is high compared to the vehicle control, one can consider that bone anabolism is being induced. Compounds of the present invention are preferably, for example, those that show increases equivalent to or greater than the level of increase in bone mineral density when hPTH(1-34) is administered as a therapeutic agent for osteoporosis to test subjects at a clinically equivalent dose level. More specifically, for example, an increase of 8% to 12% in bone mineral density relative to the vehicle control is preferred, and an increase of 12% or more is more preferred.

Induction of cartilage anabolism can be confirmed, for example, by culturing chondrocytes in the presence of a compound of the present invention, and then measuring the level of chondrocyte matrices (such as proteoglyan) produced. It can also be confirmed by determining whether terminal differentiation and calcification of chondrocytes are suppressed. Specifically, for example, the amount of cartilage matrix production can be measured by following the methods described in the documents by Loester et al. (Atrh Rheum 2003; 48(8): 2188-2196) and Ab-Rahim et al. (Mol Cell Biochem 2013; 376: 11-20). Suppression of terminal differentiation can be evaluated according to the method described in the document by Okazaki et al. (Osteoarth Cart 2003; 11(2):122-32). If the amount of cartilage matrix production is enhanced, and terminal differentiation and calcification are suppressed compared to the control, induction of cartilage anabolism may be taking place. Compounds of the present invention are preferably, for example, those that have effects equivalent to or greater than that of PTH with regard to cartilage matrix production and suppression of terminal differentiation of chondrocytes. Compared to PTH, compounds of the present invention have high metabolic stability, and therefore they have sufficient effects on the aforementioned diseased conditions and multiple routes of administration may be selected. Furthermore, when a higher-than-PTH effect can be obtained for the amount of cartilage matrix production, it becomes possible to obtain superior-to-PTH effects against the above-mentioned pathological conditions For example, induction of cartilage anabolism can be confirmed by collecting the cartilage bone of a subject continuously administered with a test substance for a certain period of time, observing this histopathologically, and observing the thickening of the articular cartilage and growth plate. Specifically, the thickness of articular cartilage and cartilage of the growth plate can be measured histologically. When the thickness of the cartilage is increased compared to that of the control, the test compound may be inducing cartilage anabolism. In particular, when cartilage thickening is noticeable compared to that of PTH, it is preferable that there are sufficient effects against the aforementioned pathological conditions, and it is more preferable when the effects are obtained through oral administration.

This can also be confirmed, for example, by following the method of Kikuchi et al. (Osteoarth Cart 1996; 4(2):99-110) and the method of Sampson et al. (Sci Transl Med 2011; 3: 101ra93) to continuously administer a test compound for a certain period of time to animals (rodents and non-rodents) with partially removed meniscus to destabilize the knee joint and induce osteoarthritis, and then visually or histopathologically evaluate the degenerated state of the articular cartilage of the knee joint. If degeneration of articular cartilage at the knee joint is suppressed in a similar manner to the case with PTH, one can determine that the test compound is effective through actions of cartilage anabolism and suppression of terminal differentiation. It is more preferable if these effects are obtained through oral administration of the test compound.

Evaluation can also be carried out, for example, by following the method of Wakitani et al. (Bone Joint Surg Br. 1989; 71(1):74-80) to administer a test compound for a certain period of time to subjects whose articular cartilage and subcartilaginous bone have been damaged, and analyze the state of cartilage regeneration at the damaged site. Observation of a cartilage regeneration effect superior to that of the control suggests induction of a cartilage anabolism effect of the test compound. In particular, a prominent cartilage regeneration effect compared to that of PTH is favorable since sufficient effects may be obtained against the aforementioned pathological conditions, and it is more preferable if the test compound exhibits these effects through oral administration.

These effects can also be confirmed by measuring PTH-like actions. PTHrP which activates PTH1R, a receptor of PTH, by paracrine action is an important factor involved in the regulation of growth and differentiation of chondrocytes, and it is known to suppress the terminal differentiation of chondrocytes and function to maintain cartilage tissues (Science 1996; 273: 663-666). Cartilage anabolism by activation of PTH1R can also be evaluated, for example, by following the method of Xie et al. (Human Mol Genet 2012; 21(18): 3941-3955) to administer a test compound for a certain period of time to normal subjects or to subjects with a genetic growth disorder, and analyze the growth speed of the cartilaginous bone and histologically analyze the thickening of the growth plate. If increases in the growth speed and growth plate thickening can be confirmed by comparison to the control, one can judge that the test compound has an cartilage anabolism effect. In particular, effects of the test compound are preferably superior to those of PTH, and it is more preferable if the test compound exhibits effects through oral administration.

The compounds according to the present invention, whether free forms or pharmacologically acceptable salts, are included in the present invention. Examples of such "salts" include inorganic acid salts, organic acid salts, inorganic base salts, organic base salts and acidic or basic amino acid salts.

Preferred examples of the inorganic acid salts include hydrochlorides, hydrobromides, sulfates, nitrates and phosphates. Preferred examples of the organic acid salts include acetates, succinates, fumarates, maleates, tartrates, citrates, lactates, stearates, benzoates, methanesulfonates, benzenesulfonates, and p-toluenesulfonates.

Preferred examples of the inorganic base salts include alkali metal salts such as sodium salts and potassium salts, alkaline earth metal salts such as calcium salts and magnesium salts, aluminum salts and ammonium salts. Preferred examples of the organic base salts include diethylamine salts, diethanolamine salts, meglumine salts and N,N-dibenzylethylenediamine salts.

Preferred examples of the acidic amino acid salts include aspartates and glutamates. Preferred examples of the basic amino acid salts include arginine salts, lysine salts and ornithine salts.

The compounds of the present invention may absorb moisture, have adsorbed water or form hydrates when left in the air. Such hydrates are also included in the salts of the present invention.

Further, the compounds of the present invention may absorb certain other solvents to form solvates. Such salts are also encompassed in the present invention as salts of the compounds of the formula (1).

Herein, a structural formula of a compound may represent a certain isomer for the sake of convenience. However, the compounds of the present invention include all isomers such as geometric isomers, optical isomers based on asymmetric carbons, stereoisomers and tautomers as well as mixtures of these isomers which occur due to the structures of the compounds, without being limited to the formulas described for the sake of convenience, and may be either one of isomers or a mixture thereof. Thus, the compounds of the present invention may have an asymmetric carbon atom in the molecule and may be present as optically active forms and racemates, but the present invention is not limited to either of them and includes both of them.

The present invention includes all isotopes of the compounds represented by the formula (1). In the isotopes of the compounds of the present invention, at least one atom is replaced by an atom having the same atomic number (proton number) but having a different mass number (sum of the number of protons and the number of neutrons). Examples of the isotopes contained in the compounds of the present invention include a hydrogen atom, a carbon atom, a nitrogen atom, an oxygen atom, a phosphorus atom, a sulfur atom, a fluorine atom and a chlorine atom, including $^{2}H$, $^{3}H$, $^{13}C$, $^{14}C$, $^{15}N$, $^{17}O$, $^{18}O$, $^{31}F$, $^{32}F$, $^{35}S$, $^{18}F$ and $^{36}Cl$, respectively. In particular, radioisotopes that decay by emitting radioactivity such as $^{3}H$ and $^{14}C$ are useful in body tissue distribution tests for pharmaceuticals or compounds. Stable isotopes do not decay, are almost equal in abundance and do not emit radioactivity, and thus they can be used safely. The isotopes of the compounds of the present invention can be converted according to conventional methods by substituting a reagent containing a corresponding isotope for a reagent used for synthesis.

The compounds according to the present invention may exhibit crystalline polymorphism, but are not particularly limited to any one of these, but may be in any one of these crystal forms or exist as a mixture of two or more crystal forms.

The compounds according to the present invention include prodrugs thereof. The prodrugs are derivatives of the compounds of the present invention which have chemically or metabolically decomposable groups and are converted back to the original compounds after administration in vivo to exhibit their original efficacy, including complexes not formed with covalent bonds, and salts.

The compounds represented by the above formula (1) according to the present invention are preferably as follows.

In the formula, R1 and R2 are selected from the combinations below:
1) R1 is a hydrogen atom or a halogen atom, and R2 is a hydrogen atom, a trifluoromethyl group, or a trifluoromethoxy group (provided that R1 and R2 are not both hydrogen atoms);
2) R1 is a trifluoromethyl group or a trifluoromethoxy group, and R2 is a hydrogen atom or a halogen atom;
3) R1 and R2 bond with each other to form a group represented by the formula below:

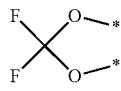

(wherein, * each indicates the position of bonding with the phenyl portion); and
R3 and R4 are methyl groups; or
R3 and R4, together with a bound carbon atom, form a ring selected from below:

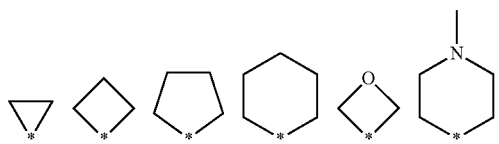

(wherein * indicates the position of bonding with the imidazolidine-2,4-dione portion).

The compounds represented by the above formula (1) according to the present invention are more preferably as follows.

In the formula, R1 and R2 are selected from the combinations below:
1) R1 is a trifuloromethoxy group and R2 is a fluorine atom;
2) R1 is a bromine atom and R2 is a hydrogen atom;
3) R1 is a trifuloromethoxy group and R2 is a fluorine atom;
4) R1 is a fluorine atom and R2 is a trifluoromethoxy group;
5) R1 is a trifluoromethyl group and R2 is a hydrogen atom;
6) R1 is a hydrogen atom and R2 is a trifluoromethoxy group;
7) R1 and R2 bond with each other to form a group represented by the formula below:

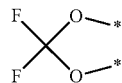

(wherein * each indicates the position of bonding with the phenyl portion); and
R3 and R4 are methyl groups; or
R3 and R4, together with a bound carbon atom, form a ring selected from below:

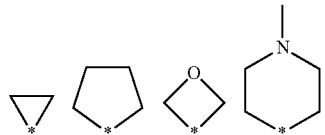

(wherein * indicates the position of bonding with the imidazolidine-2,4-dione portion).

The compounds represented by the above formula (1) according to the present invention are further preferably a compound selected from the group consisting of the following, or a pharmacologically acceptable salt thereof.

Compound 1:
1-(4-(2-((2-(4-fluoro-3-(trifluoromethoxy)phenyl)-4-oxo-1,3,8-triazaspiro[4.5]deca-1-en-8-yl)sulfonyl)ethyl)-3,5-dimethylphenyl)-5,5-dimethylimidazolidine-2,4-dione;

Compound 2:
1-(4-(2-((2-(3-bromophenyl)-4-oxo-1,3,8-triazaspiro[4.5]deca-1-en-8-yl)sulfonyl)ethyl)-3,5-dimethylphenyl)-5,5-dimethylimidazolidine-2,4-dione;

Compound 3:
1-(4-(2-((2-(4-fluoro-3-(trifluoromethyl)phenyl)-4-oxo-1,3,8-triazaspiro[4.5]deca-1-en-8-yl)sulfonyl)ethyl)-3,5-dimethylphenyl)-5,5-dimethylimidazolidine-2,4-dione;

Compound 4:
1-(4-(2-((2-(3-fluoro-4-(trifluoromethoxy)phenyl)-4-oxo-1,3,8-triazaspiro[4.5]deca-1-en-8-yl)sulfonyl)ethyl)-3,5-dimethylphenyl)-5,5-dimethylimidazolidine-2,4-dione;

Compound 5:
1-(4-(2-((2-(2,2-difluorobenzo[d][1,3]dioxol-5-yl)-4-oxo-1,3,8-triazaspiro[4.5]deca-1-en-8-yl)sulfonyl)ethyl)-3,5-dimethylphenyl)-5,5-dimethylimidazolidine-2,4-dione;

Compound 6:
1-(3,5-dimethyl-4-(2-((4-oxo-2-(3-(trifluoromethyl)phenyl)-1,3,8-triazaspiro[4.5]deca-1-en-8-yl)sulfonyl)ethyl)phenyl)-5,5-dimethylimidazolidine-2,4-dione;

Compound 7:
1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-5,5-dimethylimidazolidine-2,4-dione);

Compound 8:
1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-1,3-diazaspiro[4.4]nonane-2,4-dione;

Compound 9:
1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-8-methyl-1,3,8-triazaspiro[4.5]decane-2,4-dione;

Compound 10:
5-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-2-oxa-5,7-diazaspiro[3.4]octane-6,8-dione; and Compound 11:

4-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-4,6-diazaspiro[2.4]heptane-5,7-dione.

Of Compounds 1 to 11 above, Compounds 6, 7 and 8 are more preferred.

Such compounds of the present invention represented by the above-mentioned formula (1) or pharmaceutically acceptable salts thereof induce bone and/or cartilage anabolism, and because of such effects, they are useful for preventing or treating osteoporosis, improving decrease of bone mass in periodontal disease, facilitating recovery from alveolar bone defect after tooth extraction, preventing or treating osteoarthritis, facilitating recovery from articular cartilage deficiency, preventing or treating adynamic bone disease, preventing or treating achondroplasia, preventing or treating hypochondroplasia, or preventing or treating osteomalacia.

The compounds or salts thereof according to the present invention can be formulated by conventional methods into tablets, powders, fine granules, granules, coated tablets, capsules, syrups, troches, inhalations, suppositories, injections, ointments, ophthalmic ointments, ophthalmic preparations, nasal preparations, ear preparations, cataplasms, lotions and the like. Commonly used carriers such as excipients, binders, lubricants, colorants, correctives, and as necessary, stabilizers, emulsifiers, absorption promoters, surfactants, pH adjusters, preservatives, antioxidants and the like can be used for formulation, and they are blended with ingredients commonly used as raw materials of pharmaceutical preparations and formulated by conventional methods.

For example, oral preparations are manufactured by adding, to the compound or a pharmacologically acceptable salt thereof according to the present invention, an excipient, and as necessary, a binder, a disintegrant, a lubricant, a colorant, a corrective and the like and then formulating them into powder, fine granules, granules, tablets, coated tablets, capsules and the like by a conventional method.

Examples of these ingredients include animal and vegetable oils such as soybean oil, beef tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; silicone resin; silicone oil; surfactants such as polyoxyethylene fatty acid ester, sorbitan fatty acid ester, glycerol fatty acid ester, polyoxyethylene sorbitan fatty acid ester, polyoxyethylene hydrogenated castor oil and a polyoxyethylene-polyoxypropylene block copolymer; water-soluble polymers such as hydroxyethylcellulose, polyacrylic acid, a carboxyvinyl polymer, polyethylene glycol, polyvinylpyrrolidone and methylcellulose; lower alcohols such as ethanol and isopropanol; polyhydric alcohols such as glycerol, propylene glycol, dipropylene glycol and sorbitol; sugars such as glucose and sucrose; inorganic powders such as silicic anhydride, magnesium aluminum silicate and aluminum silicate; and purified water.

Examples of the excipients include lactose, corn starch, white soft sugar, glucose, mannitol, sorbitol, microcrystalline cellulose and silicon dioxide.

Examples of the binders include polyvinyl alcohol, polyvinyl ether, methylcellulose, ethylcellulose, acacia, tragacanth, gelatin, shellac, hydroxypropylmethylcellulose, hydroxypropylcellulose, polyvinylpyrrolidone, a polypropylene glycol-polyoxyethylene block polymer and meglumine.

Examples of the disintegrants include starch, agar, gelatin powder, microcrystalline cellulose, calcium carbonate, sodium bicarbonate, calcium citrate, dextrin, pectin and carboxymethylcellulose calcium.

Examples of the lubricants include magnesium stearate, talc, polyethylene glycol, silica and hydrogenated vegetable oil.

Colorants used are those approved as additives to pharmaceuticals. Correctives used are cocoa powder, peppermint camphor, empasm, mentha oil, borneol, powdered cinnamon bark and the like.

Obviously, these tablets and granules may be sugar-coated or otherwise coated appropriately as necessary. Liquid preparations such as syrups and injectable preparations are manufactured by adding a pH adjuster, a solubilizer, a tonicity adjusting agent and the like, and as necessary, a solubilizing agent, a stabilizer and the like to the compound or a pharmacologically acceptable salt thereof according to the present invention and formulating them by a conventional method.

The method of manufacturing external preparations is not limited and they can be manufactured by conventional methods. Specifically, various raw materials commonly used for pharmaceuticals, quasi drugs, cosmetics and the like can be used as base materials for formulation. Specific examples of the base materials used include raw materials such as animal and vegetable oils, mineral oils, ester oils, waxes, higher alcohols, fatty acids, silicone oil, surfactants, phospholipids, alcohols, polyhydric alcohols, water-soluble polymers, clay minerals and purified water. Further, pH adjusters, antioxidants, chelators, preservatives and fungicides, colorants, flavors and the like may be added as necessary. The base materials for external preparations according to the present invention are not limited to these materials.

Ingredients such as ingredients having a differentiation-inducing effect, blood flow promoters, bactericides, anti-inflammatory agents, cell activators, vitamins, amino acids, humectants and keratolytic agents may also be blended as necessary. The aforementioned base materials are added in an amount corresponding to the concentration usually chosen for the manufacture of external preparations.

The mode of administration of the compounds or salts thereof, or hydrates of the compounds or salts according to the present invention is not particularly limited, and they may be orally or parenterally administered by methods commonly used. For example, they can be formulated into preparations such as tablets, powders, granules, capsules, syrups, troches, inhalations, suppositories, injections, ointments, ophthalmic ointments, ophthalmic preparations, nasal preparations, ear preparations, cataplasms and lotions and administered.

The dosage and administration method of the medicine according to the present invention can be appropriately selected depending on the severity of the symptom, the age, the sex, the body weight, the mode of administration, the type of the salt, the specific type of the disease, and the like.

Although the dosage significantly varies according to the type of the disease and the severity of the symptom of the patient, the age of the patient, the sex difference and the difference in sensitivity to drugs between the patients, and the like, the dosage is usually about 0.03 to 1000 mg, preferably 0.1 to 500 mg and more preferably 0.1 to 100 mg per day for adults and is administered divided into one to several doses a day.

The administration route is selected appropriately by considering the type of disease and degree of symptoms of the patient, patient age and gender, difference in drug sensitivity, and such. The method of administration is not particularly limited as long as it is a method where a compound of the present invention is non-invasively exposed systemically or locally, and an effect of inducing bone and/or cartilage anabolism is obtained. Examples of such administration methods include oral administration, intravenous administration, transnasal administration, transdermal administration, transpulmonary administration, and intraarticular administration.

In the manufacture of the compounds of the present invention represented by the above formula (1), raw material compounds and various reagents may form salts, hydrates or solvates, all vary according to the starting material, the solvent used, and the like, and are not particularly limited insofar as they do not inhibit the reaction.

The solvent used also varies according to the starting material, the reagent and the like, and is not particularly limited insofar as it does not inhibit the reaction and dissolves the starting material to a certain extent, obviously.

Various isomers (e.g., geometric isomers, optical isomers based on asymmetric carbons, rotamers, stereoisomers and tautomers) can be purified and isolated using common separation means, e.g., recrystallization, diastereomeric salt methods, enzymatic resolution methods and various chromatography methods (e.g., thin-layer chromatography, column chromatography, high performance liquid chromatography and gas chromatography).

The compounds according to the present invention obtained as free forms can be converted to salts that may be formed by the compounds or to hydrates of the compounds according to conventional methods. The compounds according to the present invention obtained as salts or hydrates of the compounds can also be converted to free forms of the compounds according to conventional methods.

The compounds according to the present invention can be isolated and purified by applying common chemical operations such as extraction, concentration, evaporation, crystallization, filtration, recrystallization and various chromatography methods.

All prior art documents cited herein are hereby incorporated by reference.

General Synthesis Methods

The compounds of the present invention can be synthesized by various methods, some of which will be described with reference to the following schemes. The schemes are illustrative and the present invention is not limited only by the chemical reactions and conditions explicitly indicated. Although some substituents are excluded in the following schemes for the sake of clarity, such exclusion is not intended to limit the disclosure of the schemes. Representative compounds of the present invention can be synthesized using appropriate intermediates, known compounds, and reagents. $R_1$, $R_2$, $R_3$ and $R_4$ in the formulas in the following general synthesis methods are as defined for $R_1$, $R_2$, $R_3$ and $R_4$ in the compounds represented by the above general formula (1) (compounds represented by formula 1 in the following general synthesis methods).

The compounds of the present invention (Formula 1) can be synthesized by the manufacturing methods (Methods A and B) shown below.

Scheme 1 (Method A)

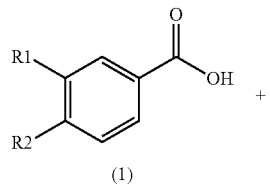

(1)

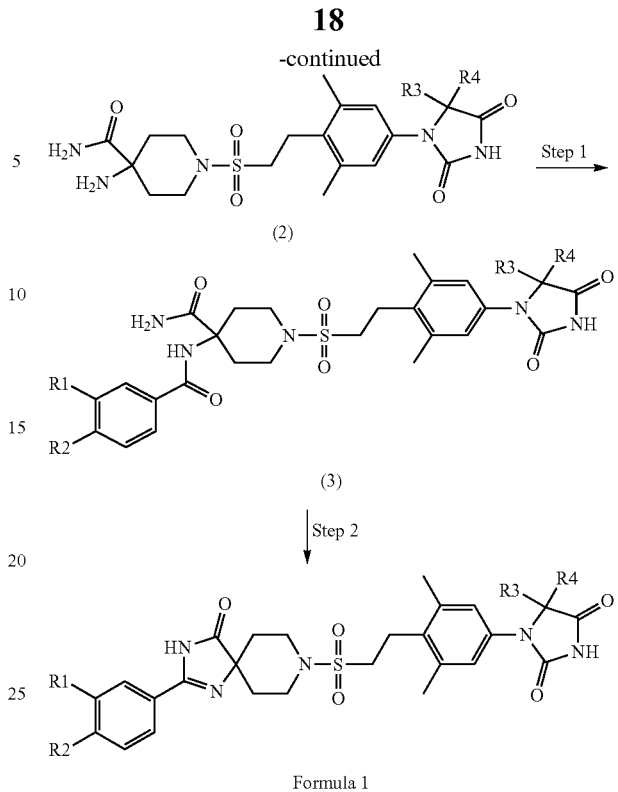

Formula 1

Scheme 1 shows a method for obtaining a hydantoin derivative (Formula 1) by amidation of the carboxylic acid derivative (1) and the amino-amide derivative (2) to obtain the amide-amide derivative (3), and then constructing the spiroimidazolone ring by intramolecular cyclization.

Step 1 is a method of the amidation of a carboxylic acid derivative (1) and an amino-amide derivative (2). Examples of the coupling reagent include N,N'-dicyclohexylcarbodiimide (DCC), 1-ethyl-3-(3-dimethylaminopropyl)carbodiimide hydrochloride (EDC), O-(7-azabenzotriazol-1-yl)-1,1,3,3-tetramethyluronium hexafluorophosphate (HATU) and 4-(4,6-dimethoxy-1,3,5-triazin-2-yl)-4-methylmorpholinium chloride n-hydrate (DMT-MM). Examples of the base include triethylamine or N,N-diisopropylethylamine. If necessary, 4-(dimethylamino)pyridine (DMAP) may be used as a catalyst. Examples of the appropriate solvent include dichloromethane or N,N-dimethylformamide. Examples of the appropriate reaction solvent when DMT-MM is used include methanol, ethanol and acetonitrile. The reaction temperature is 0° C. to room temperature, for example, and the reaction time is 0.5 to 24 hours. The resulting amino-amide derivative (3) is isolated by a common technique and, if necessary, may be purified by crystallization or chromatography.

Step 2 is a method for the cyclization of the amide-amide derivative (3) in the presence of a suitable base such as an aqueous sodium hydroxide solution or potassium t-butoxide in a suitable solvent such as ethanol, tert-butanol, or dimethylsulfoxide. The reaction temperature is carried out, for example, under room temperature to refluxing conditions for one to 24 hours. The obtained hydantoin derivative (Formula 1) is isolated by common techniques, and when necessary, it can be purified by crystallization or chromatography.

The amino-amide derivative (2) indicated in Scheme 1 can be synthesized from the piperidine derivative (4). The synthetic method for the amino-amide derivative (2) is shown in Scheme 2.

Scheme 2

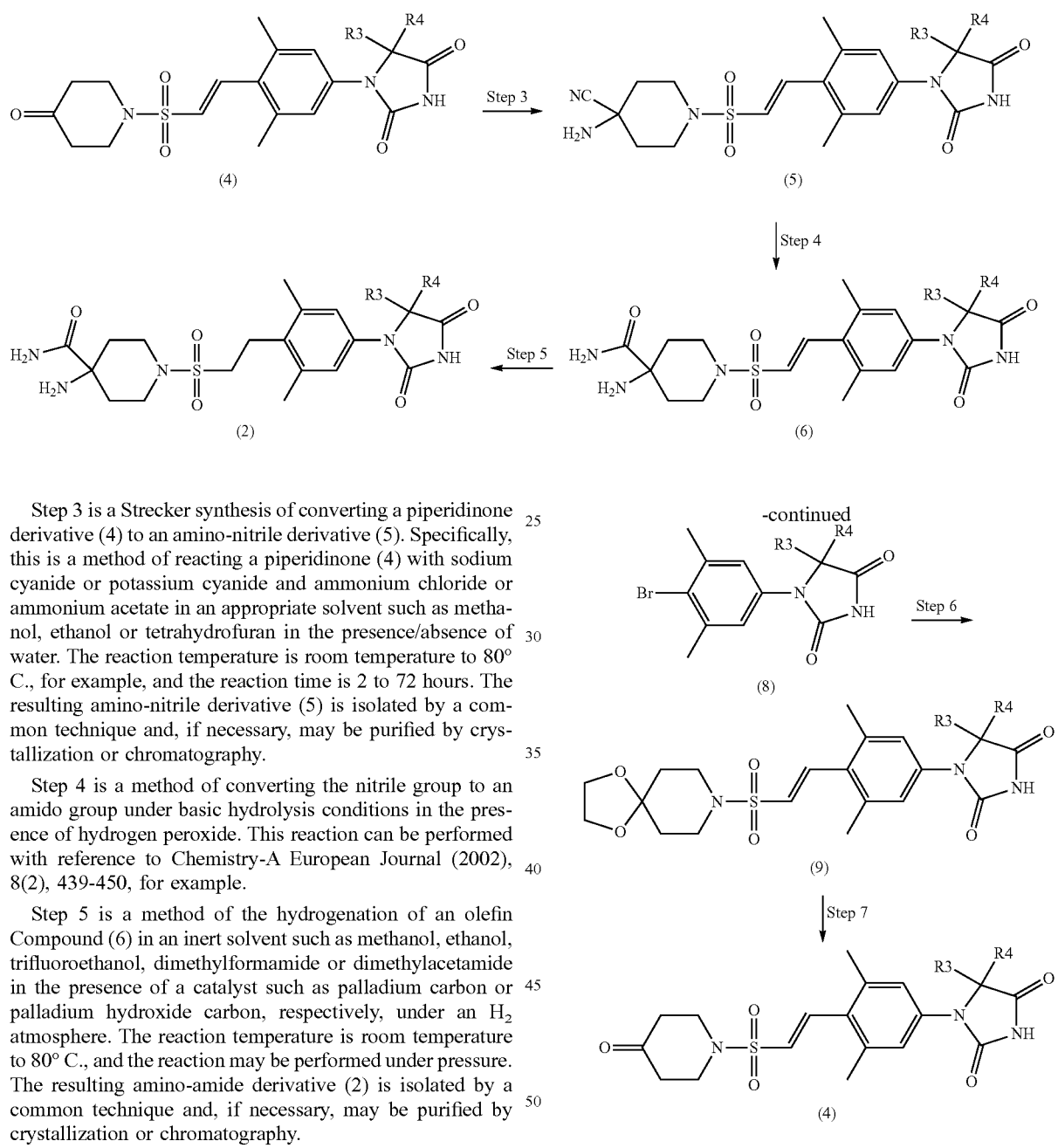

Step 3 is a Strecker synthesis of converting a piperidinone derivative (4) to an amino-nitrile derivative (5). Specifically, this is a method of reacting a piperidinone (4) with sodium cyanide or potassium cyanide and ammonium chloride or ammonium acetate in an appropriate solvent such as methanol, ethanol or tetrahydrofuran in the presence/absence of water. The reaction temperature is room temperature to 80° C., for example, and the reaction time is 2 to 72 hours. The resulting amino-nitrile derivative (5) is isolated by a common technique and, if necessary, may be purified by crystallization or chromatography.

Step 4 is a method of converting the nitrile group to an amido group under basic hydrolysis conditions in the presence of hydrogen peroxide. This reaction can be performed with reference to Chemistry-A European Journal (2002), 8(2), 439-450, for example.

Step 5 is a method of the hydrogenation of an olefin Compound (6) in an inert solvent such as methanol, ethanol, trifluoroethanol, dimethylformamide or dimethylacetamide in the presence of a catalyst such as palladium carbon or palladium hydroxide carbon, respectively, under an $H_2$ atmosphere. The reaction temperature is room temperature to 80° C., and the reaction may be performed under pressure. The resulting amino-amide derivative (2) is isolated by a common technique and, if necessary, may be purified by crystallization or chromatography.

The piperidinone derivative (4) shown in Scheme 2 can be synthesized from a known ketal vinylsulfonyl derivative (7) and a hydantoin-arylbromide derivative (8). The synthetic method for the piperidine derivative (4) is shown in Scheme 3.

Scheme 3

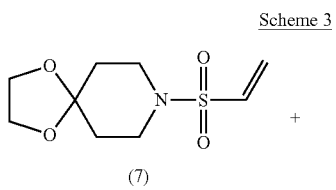

Step 6 is a method for the synthesis of a ketal-arylvinylsulfonyl derivative (9) by coupling the ketal vinylsulfonyl derivative (7) and the hydantoin-arylbromide derivative (8) under $N_2$ atmosphere in the presence of a palladium catalyst such as tris(dibenzilidineacetone)palladium(0) or bis(dibenzylidineacetone)palladium, and by adding a phosphine ligand such as tri-tert-butylphosphine tetrafluoroboric acid and a suitable base such as methyldicyclohexylamine, in a suitable solvent such as N-methyl-2-piperidone (NMP). The reaction temperature is between 90° C. and refluxing temperature. The obtained ketal-arylvinylsulfonyl derivative (9) is isolated by common techniques, and when necessary, it can be purified by crystallization or chromatography.

Step 7 is a method for the conversion of ketal of the ketal-arylvinylsulfonyl derivative (9) to ketone in a suitable solvent such as aqueous tetrahydrofuran in the presence of an acid such as hydrochloric acid. The reaction temperature is, for example, the boiling point of the solvent, and the reaction time is approximately 1 to 24 hours. The obtained piperidine derivative (4) is isolated by common techniques, and when necessary, it can be purified by crystallization or chromatography.

The hydantoin-arylbromide derivative (8) shown in Scheme 3 can be synthesized from 4-bromo-3,5-dimethylaniline (10) and the bromoacetic acid derivative (11), or from 2-bromo-5-iodo-1,3-dimethylbenzene (13) and the amino acid derivative (14). A synthetic method for the hydantoin-aryl bromide derivative (8) is shown in Scheme 4.

amino acid derivative (12) with sodium cyanate under an acidic condition. The solvent is, for example, a mixed solvent such as acetic acid—dichloromethane; the reaction temperature is room temperature to 60° C.; and the reaction time is 1 to 24 hours. The obtained hydantoin-arylbromide derivative (8) may be isolated by common techniques, and when necessary, it can be purified by crystallization or chromatography.

The hydantoin-arylbromide derivative (8) shown in Scheme 3 can also be synthesized from 4-bromo-3,5-dimethylaniline (10) and a ketone derivative (15). A synthetic method for the hydantoin-arylbromide derivative (8) is shown in Scheme 5.

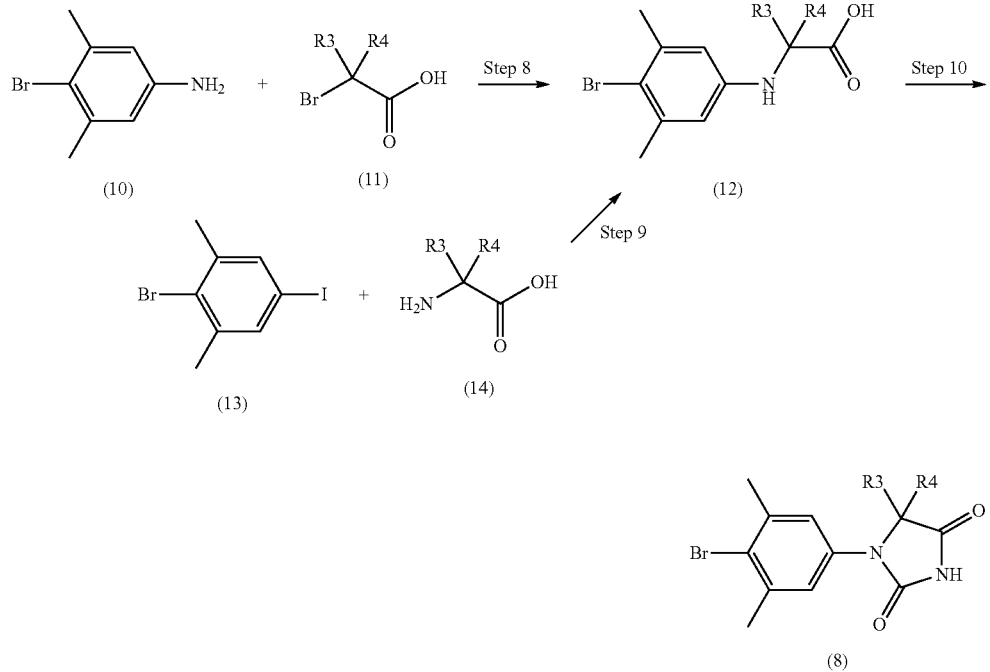

Step 8 is a method for the alkylation of 4-bromo-3,5-dimethylaniline (10) with the bromoacetic acid derivative (11) in the presence of a suitable base such as diisopropylethylamine and in a suitable solvent such as N-methyl-2-piperidone (NMP). The reaction temperature is, for example, room temperature to 100° C., and the reaction time is 1 to 24 hours. The obtained arylbromide-amino acid derivative (12) is isolated by common techniques, and when necessary, it can be purified by crystallization or chromatography.

Step 9 is a method for the synthesis of the arylbromide-amino acid derivative (12), by coupling of 2-bromo-5-iodo-1,3-dimethylbenzene (13) and the amino acid derivative (14) in the presence of a metal catalyst such as copper iodide (I). The reaction can be carried out in the presence of a suitable base such as diazabicycloundecene (DBU) and in a suitable solvent such as N,N-dimethylacetamide (DMA), at a reaction temperature of about 80° C. to 120° C. The obtained arylbromide-amino acid derivative (12) is isolated by common techniques, and when necessary, it can be purified by crystallization or chromatography.

Step 10 is a method for the synthesis of the hydantoin-arylbromide derivative (8) by reacting the arylbromide-

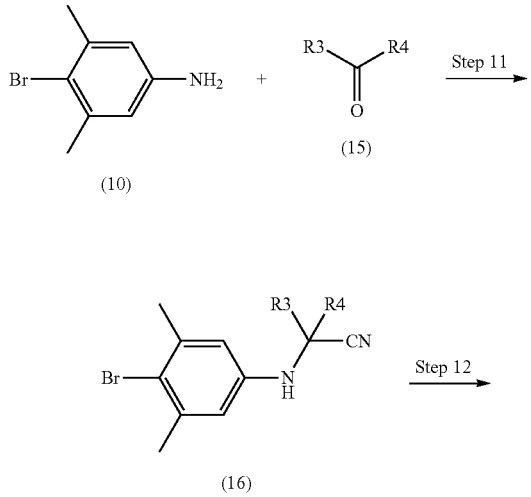

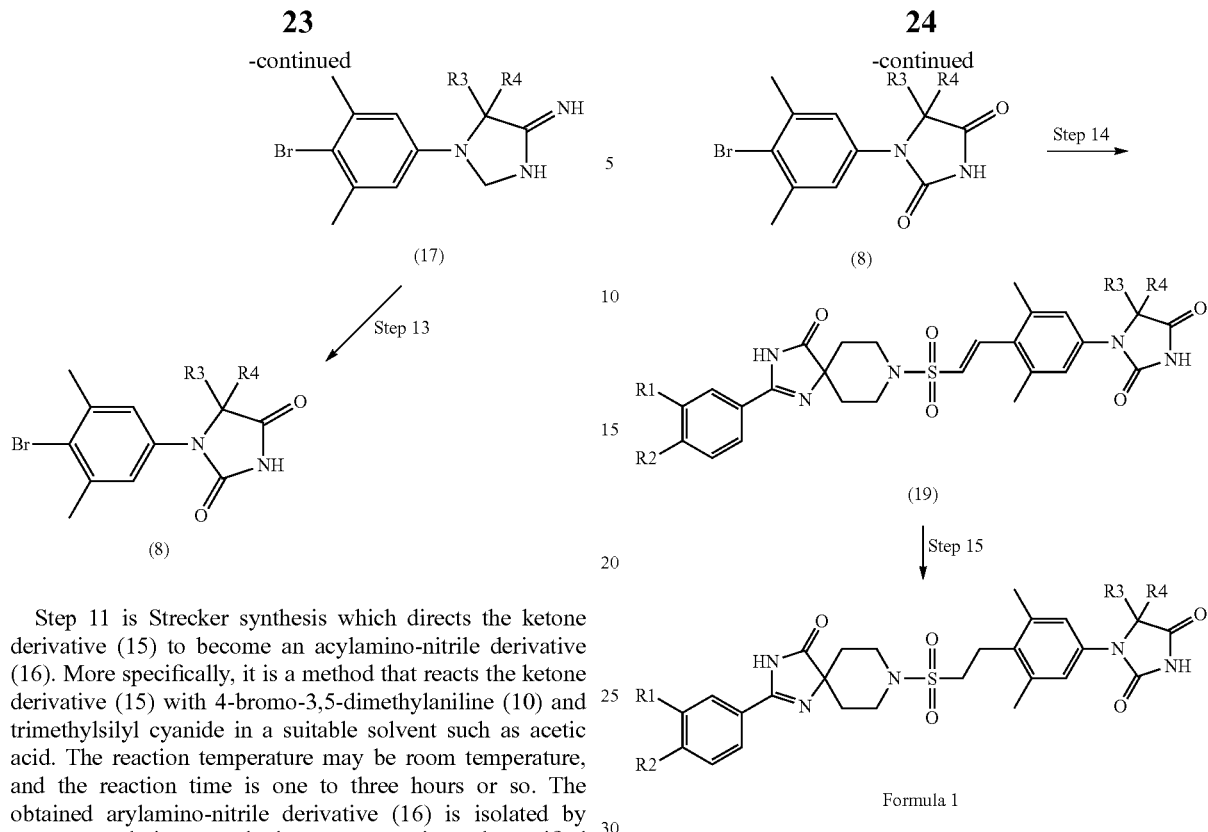

Step 11 is Strecker synthesis which directs the ketone derivative (15) to become an acylamino-nitrile derivative (16). More specifically, it is a method that reacts the ketone derivative (15) with 4-bromo-3,5-dimethylaniline (10) and trimethylsilyl cyanide in a suitable solvent such as acetic acid. The reaction temperature may be room temperature, and the reaction time is one to three hours or so. The obtained arylamino-nitrile derivative (16) is isolated by common techniques, and when necessary, it can be purified by crystallization or chromatography.

Step 12 is a method for reacting the aryl amino-nitrile derivative (16) with 2,2,2-trichloroacetylisocyanate in a suitable solvent such as dichloromethane, and then synthesizing an iminohydantoin derivative (17) by adding reagents such as methanol, water, and triethylamine and allowing them to react under heating conditions. The obtained iminohydantoin derivative (17) is isolated by common techniques, and when necessary, it can be purified by crystallization or chromatography.

Step 13 is a method for the conversion of the iminohydantoin derivative (17) into the hydantoin-arylbromide derivative (8) under an acidic condition. For example, the synthesis can be carried out in an acetic acid-water solvent with heating at approximately 65° C. for one to six hours or so. The obtained hydantoin-arylbromide derivative (8) is isolated by common techniques, and when necessary, it can be purified by crystallization or chromatography.

Scheme 6 is a method for a Heck reaction of a vinylsulfonamide derivative (18) and the hydantoin-arylbromide derivative (8) in the presence of a metal catalyst, and then the hydrogenation of olefin compound (19) to give the hydantoin derivative (Formula 1).

Scheme 6 (Method B)

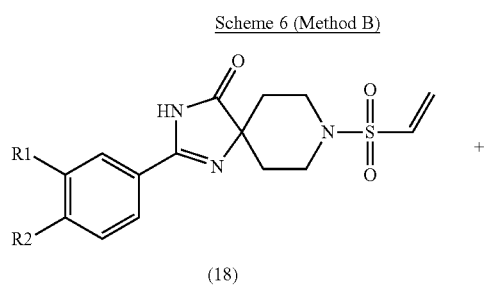

The hydantoin derivative (Formula 1) can be synthesized by performing the reaction of Step 14 according to the method of Step 6 and the reaction of Step 15 according to the method of Step 5. The obtained hydantoin derivative (Formula 1) is isolated by common techniques, and when necessary, it can be purified by crystallization or chromatography.

The vinylsulfonamide derivative (18) used in Step 14 can be synthesized by referring to Schemes 2, 3, and 12 of WO2010/126030(A1).

All prior art documents cited in this specification are incorporated herein by reference.

Herein below, the present invention will be further exemplified with reference to the Examples, but it is not to be construed as being limited thereto.

EXAMPLES

Example 1

Effects on Bone Mineral Density Upon Six Weeks of Repeated Administration to Ovariectomized Rats Female Crl:CD(SD) rats obtained from Charles River Japan, Inc. were acclimated for one week or longer under standard laboratory conditions of 20° C. to 26° C. and 35% to 75% humidity, and then used in experiments. The rats had free access to tap water and a standard rodent diet (CE-2) (Clea Japan Inc.) containing 1.1% calcium, 1.0% phosphoric acid, and 250 IU/100 g vitamin D3.

Twelve-week old rats were subjected to removal of both ovaries by surgery (OVX) or to sham surgery (Sham). After the body weight was determined in the fourth week after surgery, the rats were divided into groups so that the average body weight of each group of six rats would be even. From the subsequent day after group division, each rat was subjected to repeated administration once a day for six weeks. The solvent for oral administration (vehicle) and the solvent for subcutaneous administration (PC buffer) were respectively administered orally and subcutaneously to rats of the Sham-Control group. Vehicle and PC buffer were orally and subcutaneously administered to rats of the OVX-Control group, respectively. To rats of OVX-Compound 7, the above-mentioned Compound 7 dissolved in the vehicle was orally administered at a dose of 30 mg/kg, and PC buffer was administered subcutaneously. To rats of the OVX-hPTH(1-34) group, the vehicle was orally administered, and hPTH (1-34) dissolved in PC buffer was subcutaneously administered at a dose of 0.9 nmol/kg.

The level of AUC (area under the curve for blood concentration vs. time) was the same as when 20 μg of Forteo®, a therapeutic agent clinically used for osteoporosis, is administered to humans when the administration dose for rats was set to 0.9 nmol/kg. The administration doses were 5 mL/kg for oral administration and 1 mL/kg for subcutaneous administration in all groups. The vehicle used was a composition prepared from 10% dimethyl sulfoxide (Wako Pure Chemical Industries, Ltd.), 10% Kolliphor EL (Sigma-Aldrich Japan), and 10% hydroxypropyl-β-cyclodextrin (Nihon Shokuhin Kako Co., Ltd), whose pH was adjusted to 10 using glycine (Wako Pure Chemical Industries, Ltd.) and sodium hydroxide (Wako Pure Chemical Industries, Ltd.). The PC buffer used was a composition prepared from 25 mmol/L phosphate-citrate buffer, 100 mmol/L NaCl, and 0.05% Tween80, adjusted to pH 5.0. Rats were euthanized under anesthesia one day after the final administration by collecting blood from the abdominal aorta, and then autopsy was performed to collect the lumbar spine and femur. The lumbar spine and femur were stored in 70% ethanol. The bone mineral densities of the lumbar spine and femur were determined using a dual X-ray bone mineral scanner (DCS-600EX, Aloka). The lumbar spine bone mineral density was determined by measuring the second to fourth lumbar vertebrae; and the femur bone mineral density was determined by vertically dividing the femur into ten parts, and measuring the three parts at the distal end of the knees. The results are shown in FIG. 1.

The data are shown as mean value+standard error (SE). SAS preclinical package ver. 5.00 (SAS Institute Japan) was used to perform the following statistical analyses. The significance level was set to 5% on both sides. With regard to the lumbar spine and femur bone mineral density, a two-group t-test was used for comparison of the Sham-Control group and the OVX-Control group (#P<0.05), comparison of the OVX-Control group and the OVX-Compound 7 group (*P<0.05), and comparison of the OVX-Control group and the OVX-hPTH(1-34) group (ʃP<0.05).

As shown in FIG. 1, regarding femur bone mineral density, the OVX-Control group showed a significant decrease in bone mineral density with respect to the Sham-Control group, and the OVX-hPTH(1-34) group which is the positive control showed a significant increase with respect to the OVX-Control group. The percentage of increase in the OVX-hPTH(1-34) group with respect to the OVX-Control group was 8%. The OVX-Compound 7 group showed a significant increase with respect to the OVX-Control group, and the percentage of increase was 12%. Regarding lumbar spine bone mineral density, the OVX-Control group showed a significant decrease in bone mineral density with respect to the Sham-Control group, and the OVX-Compound 7 group showed an increasing trend with respect to the OVX-Control group, although the increase was not significant. The OVX-hPTH(1-34) group showed a significant increase with respect to the OVX-Control group, and the percentage of increase was 12%. As described above, repeated oral administration of Compound 7 caused an increase of bone mineral density in OVX rats, a pathological model for osteoporosis. Therefore, Compound 7 may be effective for preventing, treating, improving, and facilitating recovery from pathological conditions that require induction of bone anabolism, increase of bone mass, or bone regeneration, such as osteoporosis, decrease of bone mass in periodontal disease, and alveolar bone defect after tooth extraction. Furthermore, compounds represented by formula (1) have been confirmed to have strong PTH-like effects and high metabolic stability in Reference Examples 1 to 5, and they may yield an effect of increasing bone mineral density through bone anabolism by PTH-like functions. Therefore, compounds represented by formula (1) may be effective for preventing, treating, improving, and facilitating recovery from pathological conditions that require induction of bone anabolism, increase of bone mass, or bone regeneration, such as osteoporosis, decrease of bone mass in periodontal disease, and alveolar bone defect after tooth extraction.

Example 2

Effects on Bone Mineral Density Upon Four Weeks of Repeated Administration to Normal Rats Female RccHan: WIST rats obtained from Japan Laboratory Animals Inc. were acclimated for one week or longer under standard laboratory conditions of 20° C. to 26° C. and 30% to 70% humidity, and then used in experiments. The rats had free access to tap water and a standard rodent diet (CR-LPF) (Oriental Yeast Co., Ltd.).

Intravenous catheter was placed into eight-week old rats. The catheter was inserted from the femoral vein in the inguinal region, and the tip was extended into the caudal vena cava for placement at that site. The body weight was determined in the first week post-surgery, and the rats were divided into groups of ten animals per group so that the average body weight of each group would be even. Two days after group division, all rats were intravenously administered once a day repeatedly for four weeks. Administration was carried out by connecting an infusion pump (MEDFUSION SYRINGE INFUSION PUMP Model 2001) to the indwelling catheter.

The solvent (vehicle) was administered intravenously to the Vehicle-Control group. To the Compound 7-20 mg/kg, −30 mg/kg, and −50 mg/kg groups, Compound 7 dissolved in the vehicle was administered intravenously at a dose of 20 mg/kg, 30 mg/kg, and 50 mg/kg, respectively. For all groups, the administration volume was 5 mL/kg and the administration speed was 5 mL/kg/minute. The composition of the vehicle used was 5% dimethyl sulfoxide (Wako Pure Chemical Industries, Ltd.), 25% propylene glycol (Kanto Chemical Co., Inc.)/20% ethanol (Junsei Chemical Co., Ltd.)/15% hydroxypropyl-β-cyclodextrin (Nihon Shokuhin Kako Co., Ltd)/300 mM glycine (Wako Pure Chemical Industries, Ltd.)/192 mM sodium hydroxide (Wako Pure Chemical Industries, Ltd.)/physiological saline solution (Otsuka Pharmaceutical Factory, Inc.). Rats were euthanized under anesthesia the day after final administration by collecting blood from the abdominal aorta, and then autopsy was performed to collect the lumbar spine, lower leg bone, and mandible. The lumbar spine, lower leg bone, and mandible were stored in 70% ethanol. The bone mineral densities of the lumbar spine (second to fourth lumbar vertebrae), lower leg bone, and mandible were determined using a dual X-ray bone mineral scanner (DCS-600EX, Aloka). The results are shown in FIGS. 2 and 3.

The data are shown as mean value+standard error (SE). SAS preclinical package ver. 5.00 (SAS Institute Japan) was used to perform the following statistical analyses. The significance level was set to 5% on both sides. With regard to the lumbar spine, lower leg bone, and mandible bone mineral density, parametric Dunnett multiple comparison (*P<0.05) was performed for the three dosage groups of Compound 7 with the Vehicle-Control group as control.

Figure 2:
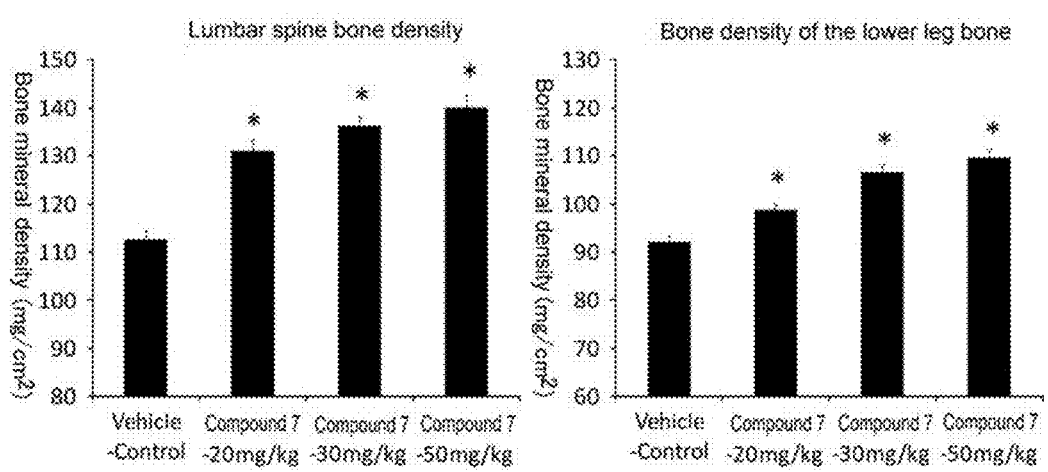
FIG. 2 shows the bone mineral densities of the lumbar spine and lower leg bone in normal rats with four weeks of repeated administration. More specifically, it shows the results of bone mineral density measurements taken on the lumbar spine and lower leg bone using a dual X-ray bone mineral scanner, when a vehicle, Compound 7, or hPTH(1-34) was repeatedly administered once a day for four weeks to normal rats.
Figure 3:
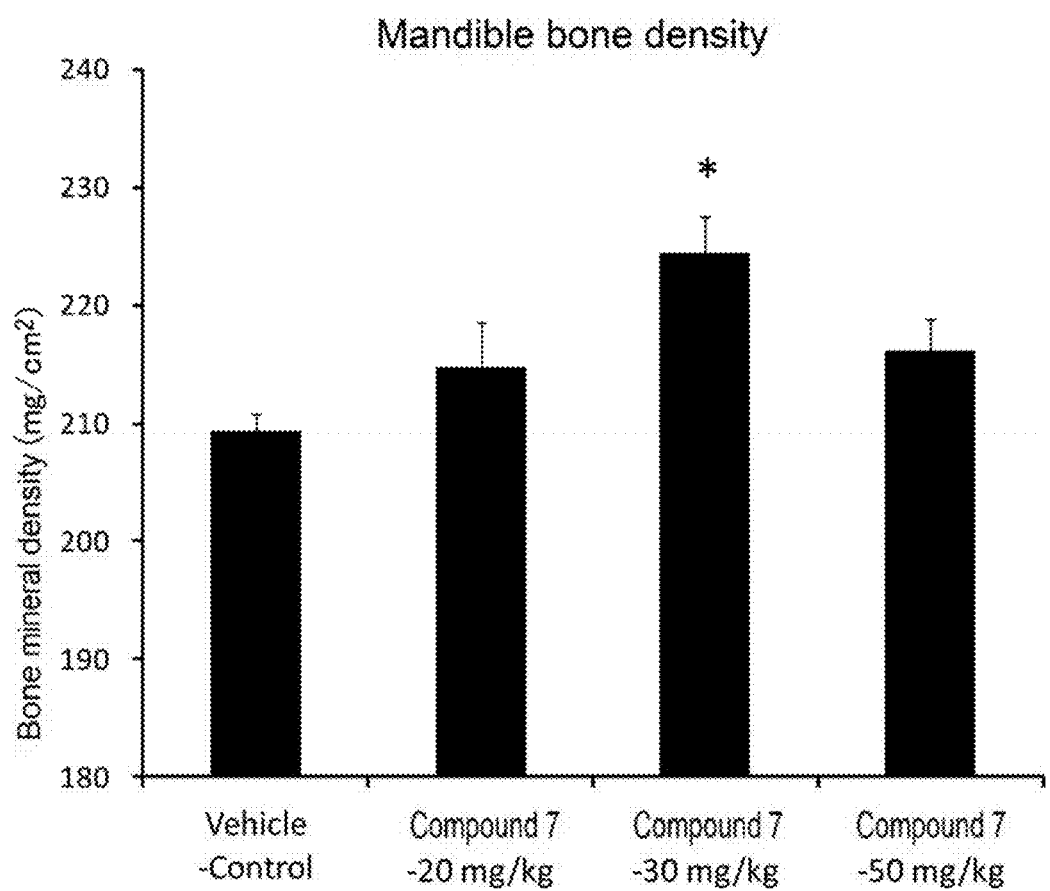
FIG. 3 shows the bone mineral densities of the mandible (lower jaw bone) in normal rats with four weeks of repeated administration. More specifically, it shows the results of bone mineral density measurements taken on the mandible using a dual X-ray bone mineral scanner, when a vehicle, Compound 7, or hPTH(1-34) was repeatedly administered once a day for four weeks to normal rats.

As shown in FIG. 2, regarding the bone mineral density of the lumbar spine and lower leg bone, the Compound 7-administered groups showed a significant effect in increasing the bone mineral density in a dose-dependent manner in comparison to the Vehicle-Control group. Furthermore, the percentage of increase in the lumbar spine bone mineral density for the three Compound 7-administered groups: 20 mg/kg group, 30 mg/kg group, and 50 mg/kg group, with respect to the Vehicle-Control group was 16%, 21%, and 25%, respectively; and the percentage of increase of bone mineral density in the lower leg bone was 7%, 16%, and 19%, respectively. As shown in FIG. 3, regarding the mandible bone mineral density, the Compound 7-30 mg/kg group showed a significant effect of increasing the bone mineral density relative to the Vehicle-Control group. The percentage of increase relative to the Vehicle-Control group was 7%.

As described above, since repeated oral administration of Compound 7 to OVX rats, a pathological model for osteoporosis caused an increase in femur bone mineral density, and repeated intravenous administration of Compound 7 caused increases in the bone mineral density of the lumbar spine, lower leg bone, and mandible in normal rats, systemic exposure of Compound 7 may be effective for preventing, treating, improving, and facilitating recovery from pathological conditions that require induction of bone anabolism, increase of bone mass, or bone regeneration, such as osteoporosis, decrease of bone mass in periodontal disease, and alveolar bone defect after tooth extraction. Furthermore, compounds represented by formula (1) have been confirmed to have strong PTH-like effects and high metabolic stability in Reference Examples 1 to 5, and they may yield an effect of increasing bone mineral density through bone anabolism by PTH-like actions. Therefore, compounds represented by formula (1) may be effective for preventing, treating, improving, and promoting recovery from pathological conditions that require induction of bone anabolism, increase of bone mass, or bone regeneration, such as osteoporosis, decrease of bone mass in periodontal disease, and alveolar bone defect after tooth extraction.

Example 3

Suppressive Effects of Compound 7 on Terminal Differentiation of Rabbit Articular Chondrocytes NZW rabbits (4-week old, Oriental Yeast Co., Ltd.) were euthanized, and then the articular cartilage of the lower leg bone was collected, and transferred to a 50-mL test tube (Nippon Becton Dickinson Company). PBS (Nacalai Tesque, Inc.) containing 1% trypsin (Wako Pure Chemical Industries, Ltd.) was added to this, and the soft tissue was digested at 37° C. for one hour. This was followed by centrifugation at 1,200 rpm for five minutes, then supernatant was removed and PBS(−) was added to suspend the cartilage tissue. This was centrifuged at 1,200 rpm for five minutes, followed by removal of the supernatant, and washed three times by suspending in PBS(−). This was centrifuged at 1,200 rpm for five minutes, and then the cell pellet was digested by treatment with DMEM (Life Technologies Japan, Ltd.) containing 0.2% Type II collagenase (CLS-2, Worthington Biochemical Corp.) at 37° C. for three hours. Fetal bovine serum (Life Technologies Japan, Ltd.) was added at 10% v/v to stop the reaction, and this was vigorously pipetted using a 10-mL pipette (Nippon Becton Dickinson Company) to isolate the chondrocytes. This was centrifuged at 1,200 rpm for five minutes, followed by removal of the supernatant, and washed three times by suspending in 10% FCS-containing DMEM, and the chondrocytes were seeded at $1 \times 10^4$ cells/well on an I-type collagen-coated 96-well culture plate (AGC TECHNO GLASS CO., LTD.). Medium exchange was performed three times a week; and after the cells reached confluency, they were cultured in DMEM containing 100 μg/mL L-ascorbic acid phosphate magnesium salt n-hydrate (Wako Pure Chemical Industries, Ltd.), 10 mmol/L β-glycerophosphate pentahydrate (Wako Pure Chemical Industries, Ltd.) and 10% FCS. The following conditions were used to culture the cells, and alkaline phosphatase staining (cultured for 14 days) and alizarin red staining (cultured for 21 days) were performed to evaluate terminal differentiation of chondrocytes.

| | |
|---|---|
| 1) Control | |
| 2) BMP-2 | 100 ng/mL |
| 3) Compound 7 | $10^{-7}$ mol/L |
| 4) Compound 7 | $10^{-6}$ mol/L |
| 5) Compound 7 | $3 \times 10^{-6}$ mol/L |
| 6) Compound 7 | $10^{-5}$ mol/L |
| 7) PTH (1-34) | $10^{-10}$ mol/L |
| 8) PTH (1-34) | $10^{-9}$ mol/L |
| 9) PTH (1-34) | $10^{-8}$ mol/L |
| 10) PTH (1-34) | $10^{-7}$ mol/L |

Alkaline phosphatase staining was performed by discarding the medium, then washing the chondrocytes once with 200 mmol/L Tris-HCl pH8.2 buffer, staining the cells according to the protocol supplied with the alkaline phosphatase staining kit (Vector Red Alkaline Phosphatase Substrate Kit I, Vector Laboratories, Inc.), and taking photographs with an inverted microscope (Nikon Corporation) (4× objective).

As a result, BMP-2 was shown to increase alkaline phosphatase activity, and both Compound 7 and PTH(1-34) suppressed alkaline phosphatase activity in a concentration-dependent manner (FIG. 4A).

Alizarin red staining was performed by discarding the medium, then washing the chondrocytes twice with PBS, fixing the cells using 100% ethanol (Wako Pure Chemical Industries Ltd.) for 15 minutes, discarding the ethanol, and then staining with 1% alizarin red S (Wako Pure Chemical Industries Ltd.) for 15 minutes, followed by washing with distilled water; and photographs were taken with an inverted microscope. As a result, BMP-2 remarkably increased the alizarin red staining property and promoted calcification. Both Compound 7 and PTH(1-34) suppressed the alizarin staining property in a concentration-dependent manner and suppressed calcification (FIG. 4B).

Example 4

Effects of Compound 7 on Proteoglycan Synthesis by Human Articular Chondrocytes

After purchase of cryopreserved human articular chondrocytes (Lot 2867, Cell Applications Inc.), the cells were thawed in a 37° C. water bath, 15 mL of Basal Medium supplemented with 10% Growth Supplement (Growth Medium, Cell Applications Inc.) was placed in a T75 culture flask (CORNING, Corning Japan K. K.) to culture the cells, and exchanged the next day with 15 mL of Growth Medium; and the cells were cultured for three days. Growth Medium was then removed, and HBSS (Cell Applications Inc.) was used to wash the chondrocyte layer. With addition of 1 mL of trypsin/EDTA solution (Cell Applications Inc.), this was left to stand at room temperature for approximately five minutes, and chondrocytes were detached from the flask. With 10 mL of Neutralization solution (Cell Applications Inc.) added, Bulker-Turk hemocytometer was used to determine the cell count, and the cells were then transferred to a 15-mL test tube for centrifugation (1,200 rpm for five minutes, Tomy Seiko Co., Ltd.) to produce a chondrocyte pellet. The supernatant was discarded, and the cells were placed in a 1.2% sodium alginate solution (25 mmol/L HEPES/150 mmol/L sodium chloride solution, pH7.0) at $2 \times 10^6$ cells/mL. This was drawn into a 1-mL syringe (Terumo Corporation) equipped with a 22G injection needle, five drops were added to each well of a 24-well plate (Corning Japan K.K.) containing 2 mL of 102 mmol/L aqueous $CaCl_2$ solution, and this was left to stand for five minutes to form beads. Subsequently, this was washed three times with a 150 mmol/L sodium chloride solution and incubated for one day in Growth Medium, and the medium was exchanged with Basal Medium supplemented with 1% Growth supplement (Cell Applications Inc.). In this procedure, the following factors were added to the medium, and the cells were cultured for 13 days with three times of medium exchange performed per week.

| | |
|---|---|
| 1) Control | |
| 2) TGF-β1 | 10 ng/mL |
| 3) PTH(1-34) | $10^{-8}$ mol/L |
| 4) Compound 7 | $10^{-6}$ mol/L |
| 5) Compound 7 | $10^{-5}$ mol/L |

On day 12 of culturing, $^{35}$S-labeled sulfuric acid (PerkinElmer Japan Co., Ltd.) was added at 370 kBq/well, and the medium was collected 24 hours later into a test tube and stored at 4° C. To the alginate gel, a 55 mmol/L sodium citrate solution (Nacalai Tesque, Inc.; 1 mL/well) was added, and this was incubated at 37° C. for ten minutes for solation. This was collected into a microtube (Eppendorf AG) and then centrifuged (1,200 rpm, five minutes) to produce a chondrocyte pellet. This was suspended by adding 0.5 mL of 1 mg/mL actinase E (Kaken Pharmaceutical Co., Ltd.)-containing 0.2 mol/L Tris-HCl (Sigma-Aldrich Co. LLC.)/5 mmol/L $CaCl_2$ (Nacalai Tesque, Inc.) pH7.8 to the microtube. The suspension was transferred to a 12-well plate (Corning Japan K.K.), sealed, and then incubated overnight in an egg incubator (ESPEC CORP.) set to 50° C. 0.4 mL of this digested solution was transferred to a test tube, 250 µL of a 0.1 mg/mL aqueous chondroitin sulfate solution (Wako Pure Chemical Industries, Ltd.), and 2.5 mL each of 2 mmol/L $MgSO_4$ (Wako Pure Chemical Industries, Ltd.), 0.2 mol/L Tris-HCl (Sigma Aldrich)/5 mmol/L $CaCl_2$ (Nacalai Tesque, Inc.) at pH7.8, 1% Cetylpyridinium chloride (CPC, Wako Pure Chemical Industries, Ltd.)/20 mmol/L NaCl (Nacalai Tesque, Inc.) were added, and this was incubated at 37° C. for three hours. This solution was filtered through a glass filter (GC-50, ADVANTEC) by suction using a vacuum pump, and 1% CPC/20 mmol/L NaCl was used for washing to remove free $^{35}$S-labeled sulfuric acid. The glass filter was transferred to a liquid scintillation counter vial, 5 mL of scintillator (Hionic-Fluor, PerkinElmer Japan Co., Ltd.) was added and radioactivity was measured on a liquid scintillation counter (TRI-CARB, PerkinElmer Japan Co., Ltd.).

The remaining 0.1 mL of the digested solution was used for DNA quantification. To 1 mL of buffer included in a DNA quantification kit (Cosmo Bio Co., Ltd.), 100 µL of the coloring solution and 450 µL of the digested solution were added together, and fluorescence intensities were measured at 458 nm with excitation at 356 nm (Infinite M200, Tecan Group Ltd.).

A standard curve for the DNA concentration was produced by preparing two-fold serially diluted solutions of the standard solution (100 µg/mL) attached to the kit. A linear regression equation was produced (Excel, Microsoft) from the results of measuring this standard curve, and DNA concentrations of the samples were calculated.

The radioactivity of each well was standardized by the DNA content (cpm/µg DNA).

Figure 5:
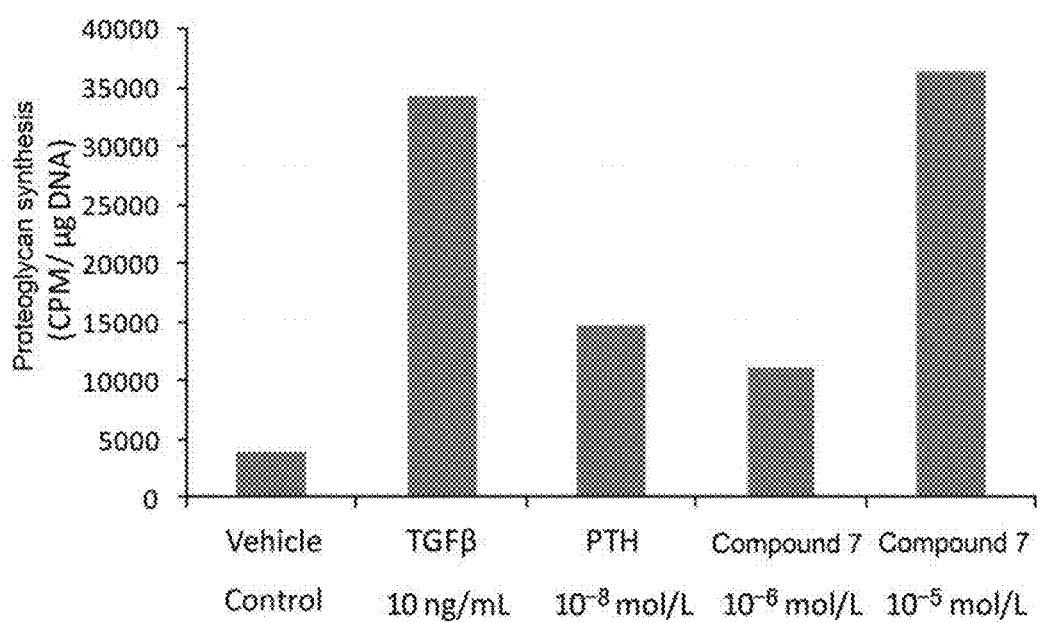
FIG. 5 shows the amount of proteoglycan synthesized in human chondrocytes. More specifically, it shows the results of evaluating the effect of Compound 7 and hPTH(1-34) in promoting proteoglycan synthesis in human chondrocytes.

As a result, the positive control, TGF-β1, showed a 10-fold radioactivity of the vehicle control, and increased the amount of proteoglycan synthesis. PTH(1-34) showed a 6-fold radioactivity of the vehicle control. Compound 7 showed a 3-fold radioactivity of the vehicle control at $10^{-6}$ mol/L, and a 10-fold radioactivity of the vehicle control at $10^{-5}$ mol/L (FIG. 5). These results showed that Compound 7 has an effect of promoting cartilage matrix synthesis in human articular chondrocytes.

Example 5

Effects of Compound 7 on Model Rabbits with Partially Removed Meniscus

Figure 4:
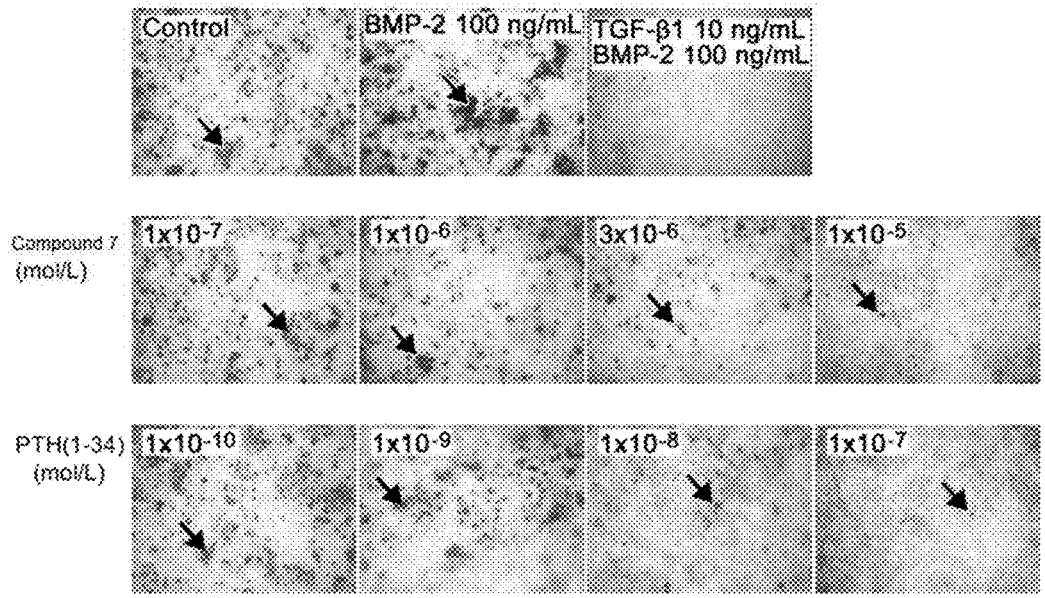
FIG. 4 shows the suppressive action of Compound 7 against terminal differentiation of articular chondrocytes of the rabbit lower leg bone. More specifically the photographs show the results of evaluating the suppressive action of Compound 7 and hPTH(1-34) against terminal differentiation of articular chondrocytes of the rabbit lower leg bone using alkaline phosphatase staining (A) and alizarin red S staining (B).
Figure 4:
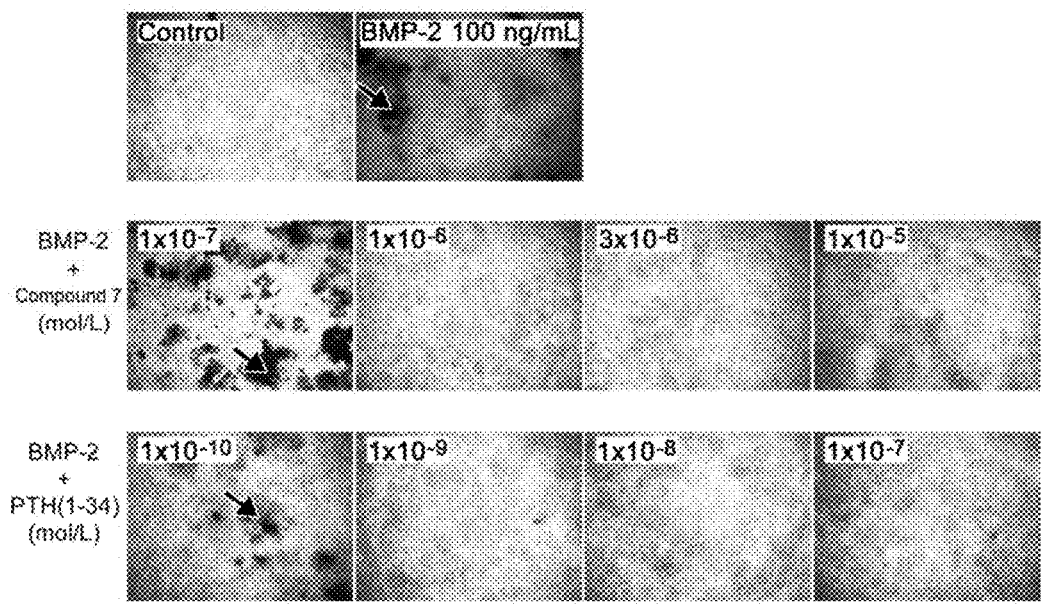
Figure 6:
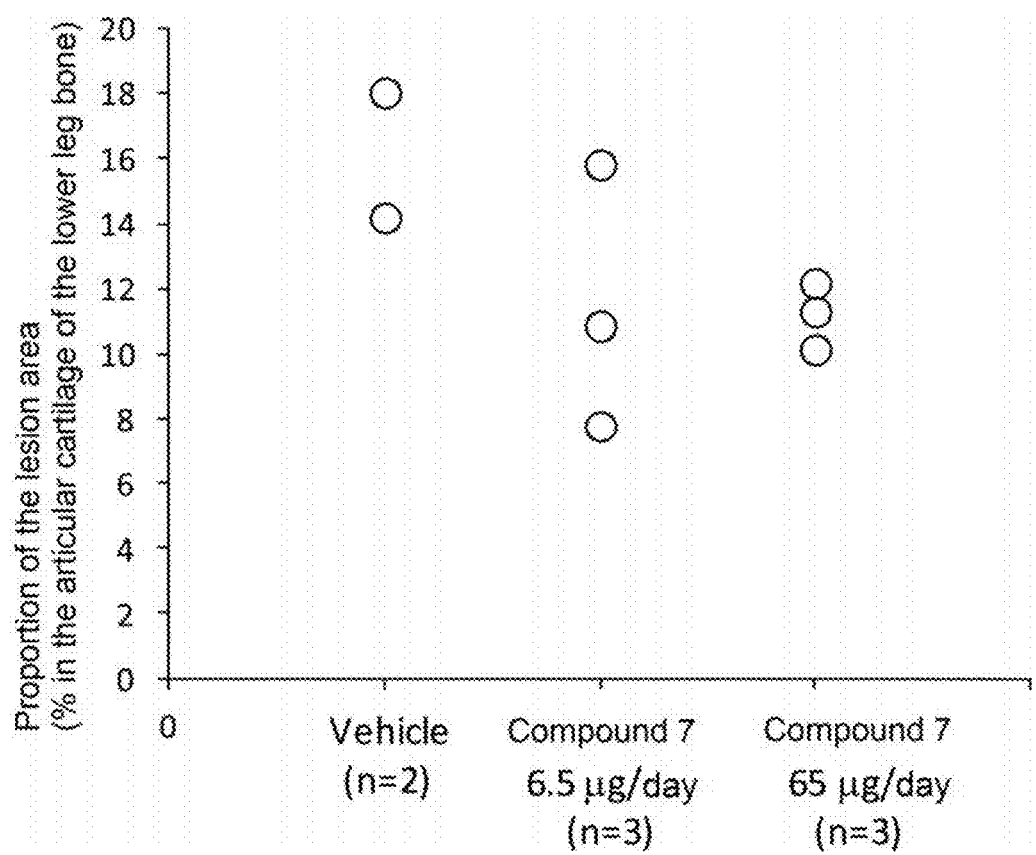
FIG. 6 shows the proportion of lesion area in the articular cartilage of the lower leg bone of model rabbits with partially removed meniscus. More specifically, it shows the results of measuring the proportion of lesion area in the articular cartilage of the lower leg bone when a vehicle or Compound 7 was continuously administered to the knee joints of model rabbits with partially removed meniscus.
Figure 7:
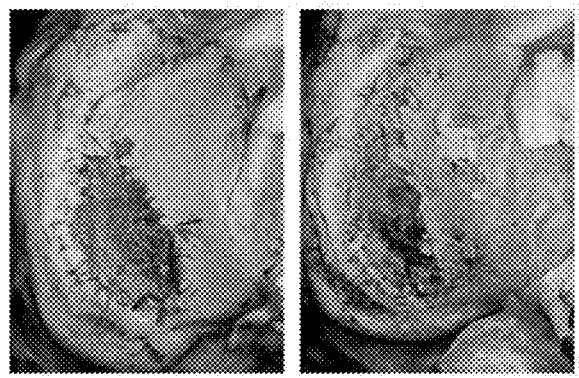
FIG. 7 shows the visually observed changes of the articular cartilage of the lower leg bone two weeks after surgery in model rabbits with partially removed meniscus. More specifically, it shows the results of visually observing the changes of the articular cartilage of the lower leg bone two weeks after surgery when a vehicle or Compound 7 was continuously administered to the knee joints of model rabbits with partially removed meniscus.
Figure 7:
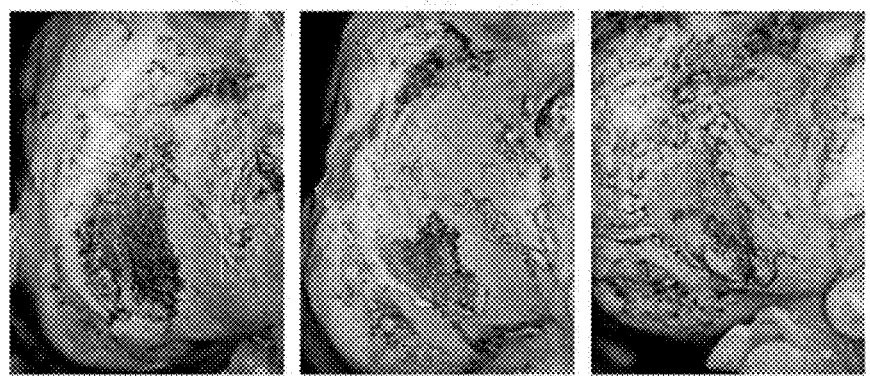
Figure 7:
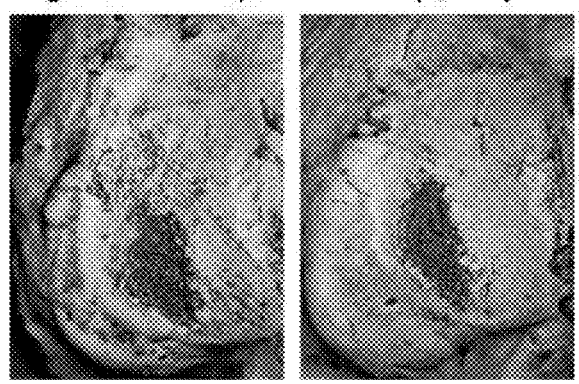

Twelve-week old male NZW rabbits (Oriental Yeast Co., Ltd.) were acclimated for five days, and then under isoflurane anesthesia, the lateral skin of the left knee joint was incised and the lateral collateral ligament and the sesamoid ligament were surgically removed to expose the lateral meniscus. The center of the lateral meniscus was excised at a width of 3 to 4 mm to produce an osteoarthritis model (Kikuchi T et al., Osteoarth Cart 1999; 4(2): 99-110). The tips of the three polyethylene tubes (PE60, Nippon Becton Dickinson Company) connected to three osmotic pumps (2ML1, Durect, Road Cupertino, Calif., US) that were embedded subcutaneously in the left femur were placed into the joint, and the drug solution was continuously administered to the knee joint. Each osmotic pump was filled with any of 1) vehicle control (50% dimethyl sulfoxide/50% physiological saline v/v); 2) Compound 7 at 3.0 µg/mL; or 3) Compound 7 at 30 µg/mL. On day 7 after surgery, the rabbits were subjected again to isofluran anesthesia, and the initial pump was replaced with an osmotic pump filled with the same pharmaceutical agent as the initially transplanted pump. The rabbits were euthanized 14 days after surgically removing a portion of the meniscus. The femur and the lower leg bone were collected, and these were fixed by soaking in 20% neutral buffered formalin. Then, the crude construction on the surface of the articular cartilage was stained using Indian ink (FIG. 7). Images of the surface structure of the lower leg bone were taken on a digital microscope (VHX-2000, Keyence Corporation), the area of the Indian ink-positive lesion site and the area of the entire lateral condyle were determined, and the proportion of the lesion site occupying the entire lateral condyle was calculated (FIG. 6). As a result, Compound 7 was found to reduce the area of the lesion site in a dose-dependent manner. Photographs of the articular cartilage surface of the lower leg bone during this experiment are shown in FIG. 4.

Example 6

Effects on Growth Plate Cartilage Upon Four Weeks of Repeated Oral Administration to Normal Rats Female RccHan: WIST rats obtained from Japan Laboratory Animals Inc. were acclimated for at least one week under standard laboratory conditions of 20° C. to 26° C. and 30% to 70% humidity, and then used in experiments. The rats had free access to tap water and a standard rodent diet (CE-2, Clea Japan Inc.) containing 1.1% calcium, 1.0% phosphoric acid, and 250 IU/100 g vitamin D3.

Figure 8:
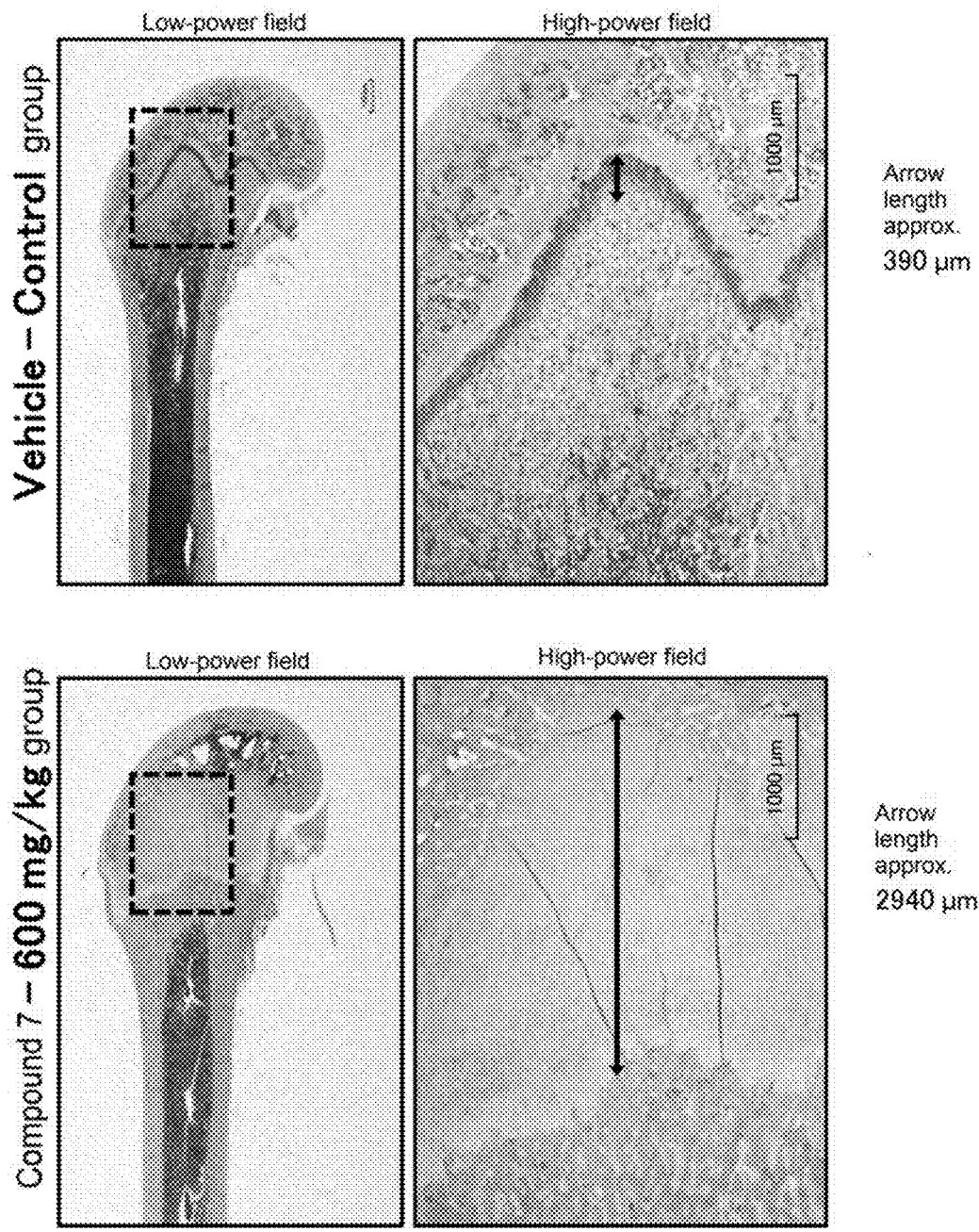
FIG. 8 shows photomicrographs of representative examples of the articular cartilage on the distal end of the femur in normal rats after four weeks of repeated oral administration. More specifically, it shows the result of histopathological observation of representative examples of the articular cartilage on the distal end of the femur under a light microscope in normal rats after four weeks of repeated daily oral administration of a vehicle or Compound 7.

After body weight measurement for the six-week old rats, they were divided into groups so that the average body weight of each group of ten rats would be even. From the day following group division, all rats were administered once a day repeatedly for four weeks. The solvent (vehicle) was orally administered to the Vehicle-Control group. To the Compound 7-6 mg/kg group, Compound 7-60 mg/kg group, and Compound 7-600 mg/kg group, Compound 7 suspended in the vehicle was administered orally at a dose of 6 mg/kg, 60 mg/kg, and 600 mg/kg, respectively. For all groups, the volume of administration was 2 mL/kg. Propylene glycol (special grade, Kanto Chemical Co., Inc.) was used for the vehicle. The rats were euthanized under anesthesia one day after the final administration by collecting blood from the abdominal aorta, and then autopsy was performed to collect the femur. The femur was fixed using a 10% neutral buffered formalin solution, and after demineralization, samples of paraffin-embedded tissue sections (hematoxylin-eosin stained) were prepared. Distal ends of the femur of the produced samples were observed histopathologically under a light microscope. The results are shown in Table 1, and representative histological images are shown in FIG. 8.

TABLE 1

Histological changes in the femoral growth plate cartilage after four weeks of repeated oral administration to normal rats.

| | | | Vehicle-Control | Compound 7 6 mg/kg | Compound 7 60 mg/kg | Compound 7 600 mg/kg |
|---|---|---|---|---|---|---|
| Group | | | | | | |
| Number of examples per group | | | 10 | 10 | 10 | 10 |
| | Overall | | — | — | 8 | 10 |
| Number of cases in which growth plate cartilage thickening was observed | Classification | Grade 1 | — | — | 5 | — |
| | | Grade 2 | — | — | 3 | — |
| | | Grade 3 | — | — | — | 1 |
| | | Grade 4 | — | — | — | 9 |

As shown in Table 1, the Compound 7 groups caused dose-dependent thickening of the femoral growth plate cartilage in comparison to the Vehicle-Control group. When the width of a representative growth plate cartilage (indicated by an arrow) was determined from the tissue image of FIG. 8 based on the scale, it was approximately 390 μm for an individual in the Vehicle-Control group and approximately 2940 μm for an individual in the Compound 7-600 mg/kg group.

As described above, repeated oral administration of Compound 7 caused thickening of the rat femoral growth plate cartilage. Such effects are due to induction of cartilage anabolism, suppression of the terminal differentiation of cartilage, or promotion of cartilage growth by Compound 7, and thus oral administration of Compound 7 may be effective for treating osteoarthritis. Furthermore, compounds represented by formula (1) have been confirmed to have strong PTH-like effects and high metabolic stability in Reference Examples 1 to 5, and they are expected to be effective for treatment of osteoarthritis through cartilage anabolism by PTH-like actions.

REFERENCE EXAMPLES

The content of the present invention will be described in more detail by the following examples and test example; however, the present invention is not limited to the content of the examples and test example. All starting materials and reagents were obtained from commercial suppliers or synthesized using known methods. $^1$H-NMR spectra were measured using Mercury300 (manufactured by Varian), ECP-400 (manufactured by JEOL) or 400-MR (manufactured by Varian) with or without Me$_4$Si as the internal standard (s=singlet, d=doublet, t=triplet, brs=broad singlet, m=multiplet). Mass spectrometry measurement was performed using a mass spectrometer, ZQ2000 (manufactured by Waters), SQD (manufactured by Waters) or 2020 (manufactured by Shimazu).

Reference Example 1

1-(4-(2-((2-(4-fluoro-3-(trifluoromethoxy)phenyl)-4-oxo-1,3,8-triazaspiro[4.5]deca-1-en-8-yl)sulfonyl)ethyl)-3,5-dimethylphenyl)-5,5-dimethylimidazolidine-2,4-dione (Compound 1)

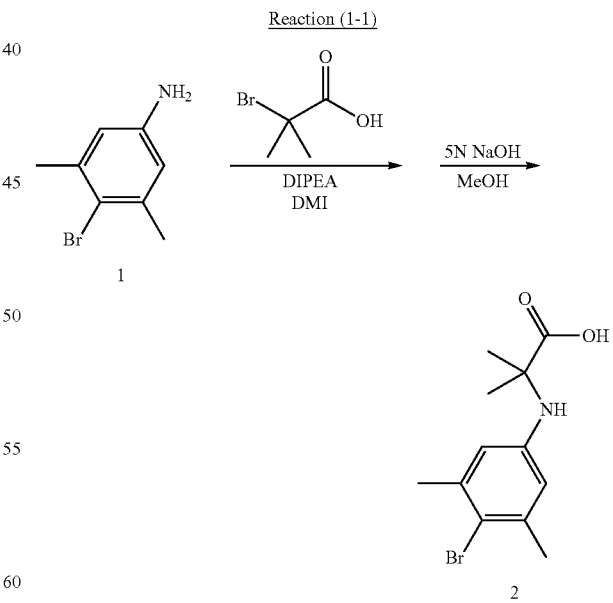

To a solution of 4-bromo-3,5-dimethylaniline (3.47 g, 17.4 mmol) and diisopropylethylamine (5.3 mL, 30.4 mmol) in DMI (13 mL), 2-bromoisobutyric acid (3.86 g, 23.1 mmol) was added at room temperature. The mixture was stirred at 100° C. for one hour. And then 2-bromoisobutyrate (496 mg, 2.97 mmol) and diisopropylethylamine (0.8 mL, 4.59 mmol) was added and the mixture was stirred at 100° C. for one hour.

Methanol (52 mL) and a 5 N aqueous sodium hydroxide solution (52 mL, 260 mmol) were added to the reaction mixture at room temperature, and then this mixture was stirred at 75° C. for 1.5 hours. The reaction mixture was cooled, followed by addition of water and adjustment of the pH to 5 using a 1 N aqueous potassium hydrogen sulfate solution, and then extracted using ethyl acetate. The organic layer was washed with water, then dried over anhydrous magnesium sulfate, and concentrated to yield 2-((4-bromo-3,5-dimethylphenyl)amino)-2-methyl propanoic acid as a crude product (5.79 g).

MS(ESI) m/z=286, 288 (M+H)+

(Reaction 1-2)

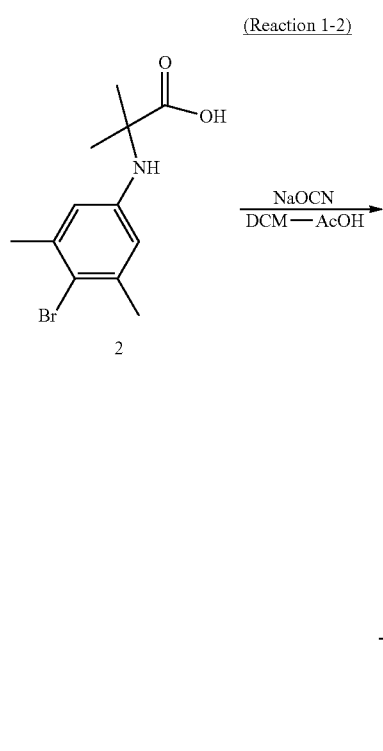

To a mixture of 2-((4-bromo-3,5-dimethylphenyl)amino)-2-methyl propanoic acid (5.79 g of the compound obtained from Reaction 1-1) in dichloromethane (62 mL) and acetic acid (62 mL), sodium cyanate (5.03 g, 59.8 mmol) was added at room temperature. The mixture was stirred at room temperature for three hours. A saturated solution of sodium hydrogen carbonate (400 mL) was added to adjust the pH to 7-8 using a 5 N aqueous sodium hydroxide, and this mixture was extracted with ethyl acetate. The organic layer was dried over anhydrous magnesium sulfate, and then concentrated under reduced pressure. The obtained solid was washed sequentially with ethyl acetate-hexane and then with dichloromethane-hexane to obtain 1-(4-bromo-3,5-dimethylphenyl)-5,5-dimethylimidazolidine-2,4-dione (3.80 g, 66%).

MS(ESI) m/z=311, 313 (M+H)+

(Reaction 1-3)

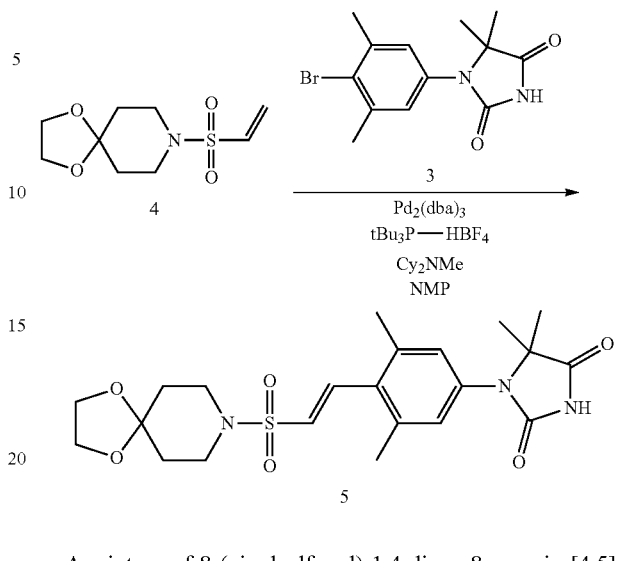

A mixture of 8-(vinylsulfonyl)-1,4-dioxa-8-azaspiro[4.5]decane (431 mg, 1.85 mmol), 1-(4-bromo-3,5-dimethylphenyl)-5,5-dimethylimidazolidine-2,4-dione (575 mg, 1.85 mmol), tris(dibenzylidineacetone)palladium(0) (508 mg, 0.55 mmol), tri-tert-butylphosphine tetrafluoroboric acid (165 mg, 0.55 mmol), and methyldicyclohexylamine (2.1 mL, 9.25 mmol) in N-methyl-2-pyrrolidone (18.5 mL) was stirred under nitrogen atmosphere at 110° C. for two hours. The reaction mixture was cooled, quenched with water, and then extracted with ethyl acetate. The organic layer was washed with water and brine, dried over anhydrous magnesium sulfate, and then concentrated under reduced pressure. The residue was purified by amino-silica gel column chromatography (dichloromethane—methanol) to afford (E)-1-(4-(2-(1,4-dioxa-8-azaspiro[4.5]decan-8-ylsulfonyl)vinyl)-3,5-dimethylphenyl)-5,5-dimeth ylimidazolidine-2,4-dione (584 mg, 68%).

MS(ESI) m/z=464 (M+H)+

(Reaction 1-4)

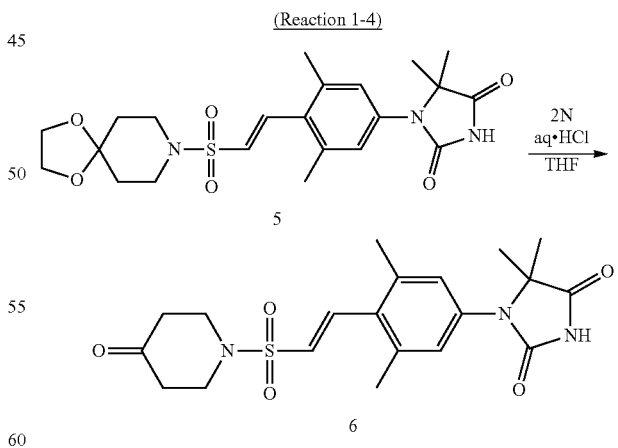

To a solution of (E)-1-(4-(2-(1,4-dioxa-8-azaspiro[4.5]decan-8-ylsulfonyl)vinyl)-3,5-dimethylphenyl)-5,5-dimeth ylimidazolidine-2,4-dione (1.2 g, 2.58 mmol) in tetrahydrofuran (26 mL), a 2 N aqueous hydrochloric acid solution (26 mL, 52 mmol) was added dropwise over ten minutes. The mixture was stirred at 60° C. for two hours. The reaction mixture was cooled, followed by adjustment of its pH to 7 using a 2 N aqueous sodium hydroxide solution, and this mixture was extracted with ethyl acetate. The organic layer was washed with brine, dried over anhydrous magnesium sulfate, and then concentrated under reduced pressure. The residue was purified by silica gel column chromatography (dichloromethane—ethyl acetate) to afford (E)-1-(3,5-dimethyl-4-(2-((4-oxopipedridin-1-yl)sulfonyl)vinyl)phenyl)-5,5-dimethylimidazolidine-2,4-dione (998 mg, 92%).

MS(ESI) m/z=420 (M+H)+

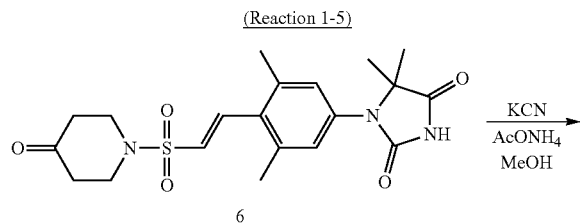

(Reaction 1-5)

6

7

To a solution of (E)-1-(3,5-dimethyl-4-(2-((4-oxopipedridin-1-yl)sulfonyl)vinyl)phenyl)-5,5-dimethylimidazolidine-2,4-dione (994 mg, 2.37 mmol) in methanol (24 mL), potassium cyanide (188 mg, 2.84 mmol) and ammonium acetate (237 mg, 3.08 mmol) were added at room temperature. The mixture was stirred at 60-70° C. for three hours. The reaction mixture was cooled, concentrated under reduced pressure, and then diluted with ethyl acetate. The organic layer was washed with water and brine, dried over anhydrous magnesium sulfate, and then concentrated under reduced pressure. The residue was purified by silica gel column chromatography (dichloromethane—ethyl acetate) to afford (E)-4-amino-1-((4-(5,5-dimethyl-2,4-dioxoimidazolidin-1-yl)-2,6-dimethylstyryl)sulfonyl)piperidine-4-carbonitrile (681 mg, 68%).

¹H-NMR (300 MHz, DMSO-d₆) δ: 1.3 (6H, s), 1.7 (2H, m), 2.0 (2H, m), 2.3 (6H, s), 2.7 (2H, s), 2.9 (2H, m), 3.4 (2H, m), 6.9 (1H, d, J=15.9 Hz), 7.1 (2H, s), 7.4 (1H, d, J=15.9 Hz), 11.2 (1H, brs)

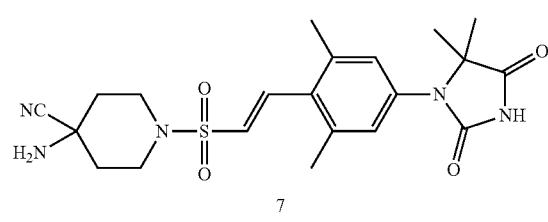

(Reaction 1-6)

7

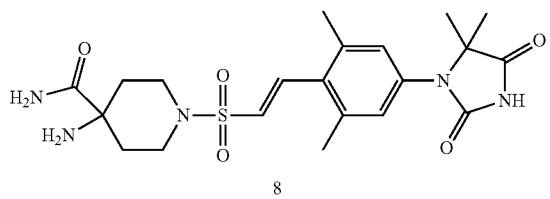

8

To a solution of (E)-4-amino-1-((4-(5,5-dimethyl-2,4-dioxoimidazolidin-1-yl)-2,6-dimethylstyryl)sulfonyl)piperidine-4-carbonitrile (675 mg, 1.50 mmol) in methanol (7.5 mL) and dimethylsulfoxide (0.195 mL) at room temperature, a 2 N aqueous sodium hydroxide solution (1.6 ml, 1.6 mmol) was added and then a 30% aqueous hydrogen peroxide solution (0.2 mL, 1.95 mmol) were slowly added dropwise. The mixture was stirred at room temperature for one hour. Ethyl acetate, hexane, and a saturated aqueous ammonium chloride solution were added to the reaction mixture. The solid was collected by filtration, washed, and dried to afford (E)-4-amino-1-((4-(5,5-dimethyl-2,4-dioxoimidazolidine-1-yl)-2,6-dimethylstyryl)sulfonyl)piperidine-4-carboxamide (498 mg, 72%).

MS(ESI) m/z=464 (M+H)+

(Reaction 1-7)

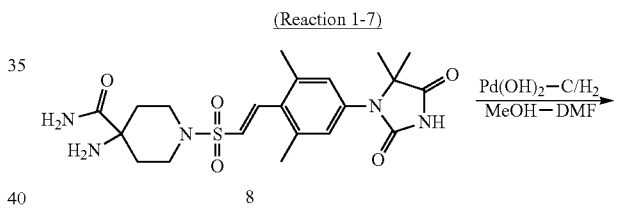

8

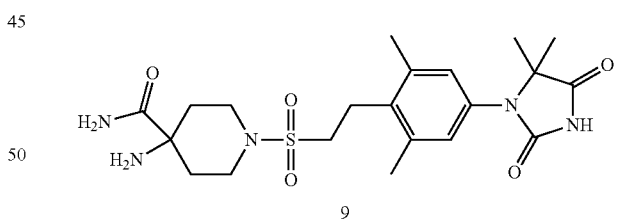

9

A mixture of (E)-4-amino-1-((4-(5,5-dimethyl-2,4-dioxoimidazolidine-1-yl)-2,6-dimethylstyryl)sulfonyl)piperidine-4-carboxamide (1.3 g, 2.8 mmol) and palladium hydroxide on carbon (20% Pd) (wetted with approximately 50% water) (1.3 g) in methanol (21 mL) and dimethylformamide (7 mL) was stirred under hydrogen atmosphere at room temperature for four hours. The reaction mixture was filtered and washed, and then the filtrate was concentrated under reduced pressure to afford 4-amino-1-((4-(5,5-dimethyl-2,4-dioxoimidazolidin-1-yl)-2,6-dimethylphenethyl)sulfonyl)piperidin-4-carboxamide (998 mg, 77%).

MS(ESI) m/z=466 (M+H)+

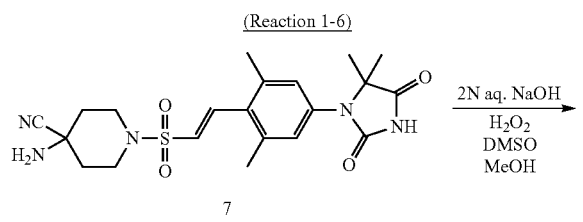

(Reaction 1-8)

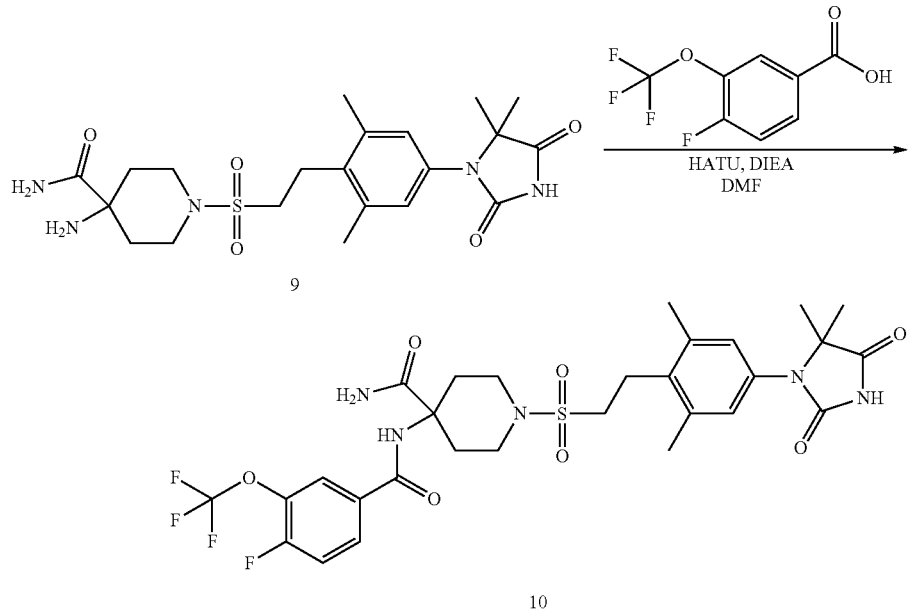

To a solution of 4-amino-1-((4-(5,5-dimethyl-2,4-dioxoimidazolidin-1-yl)-2,6-dimethylphenethyl)sulfonyl)piperidin-4-carboxamide (120 mg, 0.258 mmol), 4-fluoro-3-(trifluoromethoxy)benzoic acid (69 mg, 0.309 mmol), and diisopropylethylamine (0.09 ml, 0.516 mmol) in dimethylformamide (2.5 mL), O-(7-azabenzotriazol-1-yl)-1,1,3,3-tetramethyluroniumhexafluorophosphate (HATU) (118 mg, 0.309 mmol) was added. The mixture was stirred at room temperature for 1.5 hours. The reaction mixture was quenched with water, and then extracted with dichloromethane. The organic layer was washed with brine, washed with anhydrous sodium sulfate, and then concentrated under reduced pressure to afford 1-((4-(5,5-dimethyl-2,4-dioxoimidazolidin-1-yl)-2,6-dimethylphenethyl)sulfonyl)-4-(4-fluoro-3-(trifluoromethoxy)benzamide)piperidine-4-carboxamide (150 mg, 67%).

MS(ESI) m/z=672 (M+H)+

(Reaction 1-9)

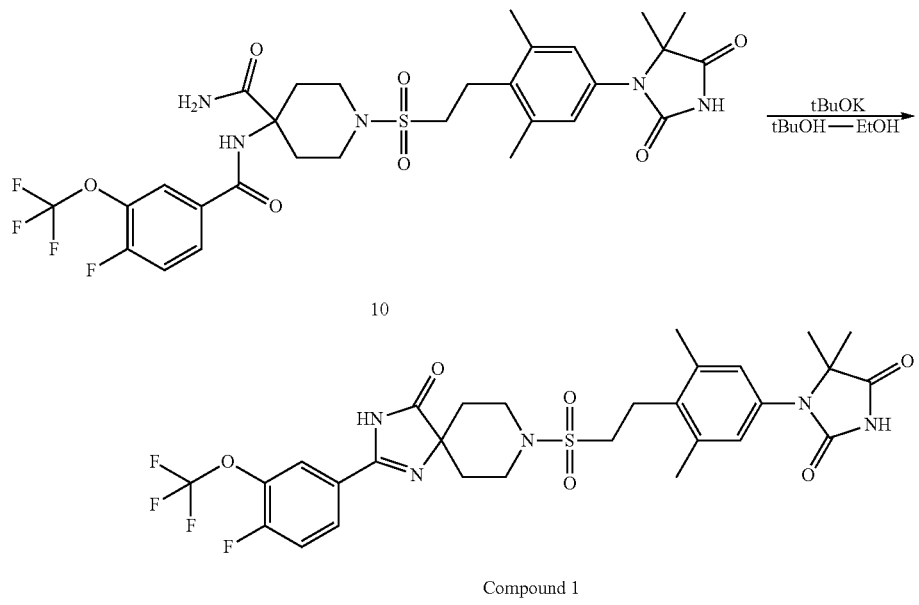

Compound 1

To a mixed solution of 1-((4-(5,5-dimethyl-2,4-dioxoimidazolidin-1-yl)-2,6-dimethylphenethyl)sulfonyl)-4-(4-fluoro-3-(trifluoromethoxy)benzamide)piperidine-4-carboxamide (150 mg, 0.223 mmol) in tert-butanol (2.5 mL) and ethanol (2.5 mL), potassium tert-butoxide (75 mg, 0.670 mmol) was added at 0° C. The mixture was stirred under nitrogen atmosphere at 50° C. for 1.5 hours. The reaction mixture was cooled, diluted with water, quenched with a saturated aqueous ammonium chloride solution, and then extracted with dichloromethane. The organic layer was washed with water and brine, dried over anhydrous sodium sulfate, and then concentrated under reduced pressure. The obtained residue was purified by silica gel column chromatography (dichloromethane—methanol) to afford 1-(4-(2-((2-(4-fluoro-3-(trifluoromethoxy)phenyl)-4-oxo-1,3,8-triazaspiro[4.5]deca-1-en-8-yl)sulfonyl)ethyl)-3,5-dimethylphenyl)-5,5-dimethylimidazolidine-2,4-dione 118 mg, 81%).

MS(ESI) m/z=654 (M+H)+. $^1$H-NMR (400 MHz, CD$_3$OD) δ: 1.40 (6H, s), 1.71-1.80 (2H, m), 2.00-2.08 (2H, m), 2.43 (6H, s), 3.22 (4H, s), 3.47-3.57 (2H, m), 3.80-3.88 (2H, m), 7.01 (2H, s), 7.50-7.57 (1H, m), 7.97-8.04 (1H, m), 8.05-8.12 (1H, m)

The following compounds of the Reference Examples were synthesized by operations similar to those of Reactions 1-8 and 1-9 in Reference Example 1, using appropriate carboxylic acid starting materials, reagents, and solvents. (Compound 2-5)

TABLE 2

| Compound | Carboxylic acid starting material | Structural formula of compound | Analytical data |
|---|---|---|---|
| 2 | 3-bromobenzoic acid | [structure] | MS(ESI) m/z = 630, 632 (M + H)+. $^1$H-NMR (400 MHz, DMSO-d$_6$) δ: 1.30 (6H, s), 1.56-1.63 (2H, m), 1.80-1.90 (2H, m), 2.37 (6H, s), 3.00-3.08 (2H, m), 3.23-3.30 (2H, m), 3.32-3.41 (2H, m), 3.67-3.73 (2H, m), 7.00 (2H, s), 7.50 (1H, dd, J = 8.8 Hz), 7.77-7.82 (1H, m), 7.95-8.00 (1H, m), 8.13-8.20 (1H, m), 11.10 (1H, brs), 11.70 (1H, brs) |
| 3 | 4-fluoro-3-(trifluoromethyl)benzoic acid | [structure] | MS(ESI) m/z = 638 (M + H)+. $^1$H-NMR (400 MHz, CDCl$_3$) δ: 1.47 (6H, s), 1.70-1.78 (2H, m), 2.09-2.18 (2H, m), 2.40 (6H, s), 3.00-3.08 (2H, m), 3.20-3.28 (2H, m), 3.44-3.54 (2H, m), 3.80-3.88 (2H, m), 6.94 (2H, s), 7.34 (1H, t, J = 9.6 Hz), 8.02 (1H, brs), 8.08-8.13 (1H, m), 8.20-8.24 (1H, m), 10.10 (1H, brs) |
| 4 | 3-fluoro-4-(trifluoromethoxy)benzoic acid | [structure] | MS(ESI) m/z = 654 (M + H)+. $^1$H-NMR (400 MHz, DMSO-d$_6$) δ: 1.30 (6H, s), 1.58-1.64 (2H, m), 1.81-1.91 (2H, m), 2.37 (6H, s), 3.00-3.08 (2H, m), 3.22-3.31 (2H, m), 3.32-3.42 (2H, m), 3.68-3.73 (2H, m), 7.00 (2H, s), 7.76-7.82 (1H, m), 7.95 (1H, d, J = 9.6 Hz), 8.05 (1H, dd, J = 9.8, 2 Hz), 11.09 (1H, s), 11.79 (1H, s) |
| 5 | 2,2-difluoro-1,3-benzodioxole-5-carboxylic acid | [structure] | MS(ESI) m/z = 632 (M + H)+. $^1$H-NMR (400 MHz, CDCl$_3$) δ: 1.47 (6H, s), 1.65-1.73 (2H, m), 2.11-2.20 (2H, m), 2.39 (6H, s), 2.98-3.04 (2H, m), 3.18-3.25 (2H, m), 3.40-3.52 (2H, m), 3.82-3.90 (2H, m), 6.94 (2H, s), 7.17 (1H, d, J = 8.4 Hz), 7.63 (1H, d, J = 8.4 Hz), 7.75 (1H, s), 8.49 (1H, brs), 10.46 (1H, brs) |

Reference Example 2

1-(3,5-dimethyl-4-(2-((4-oxo-2-(3-(trifluoromethyl)phenyl)-1,3,8-triazaspiro[4.5]deca-1-en-8-yl)sulfonyl)ethyl)phenyl)-5,5-dimethylimidazolidine-2,4-dione (Compound 6)

(Reaction 2-1)

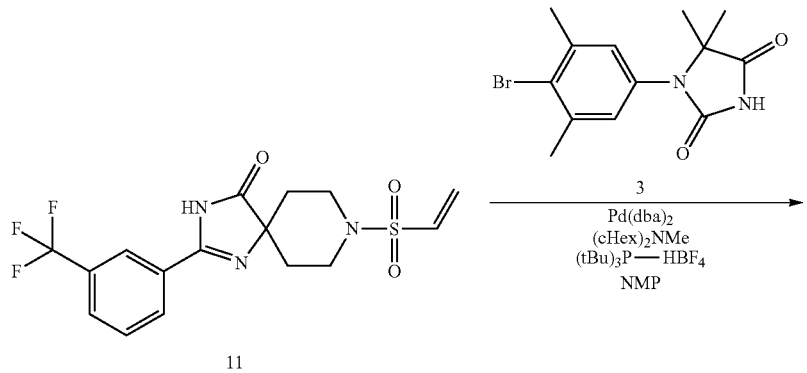

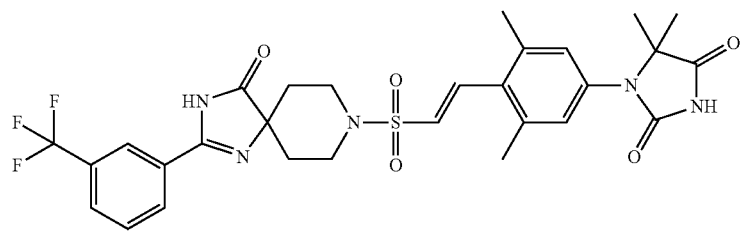

A mixture of 2-(3-(trifluoromethyl)phenyl)-8-(vinylsulfonyl)-1,3,8-triazaspiro[4.5]deca-1-en-4-one (150 mg, 0.387 mmol) synthesized according to the method described in Schemes 2, 3, and 12 of WO2010/126030(A1), 1-(4-bromo-3,5-dimethylphenyl)-5,5-dimethylimidazolidine-2,4-dione (169 mg, 0.542 mmol), bis(dibenzylidineacetone) palladium (45 mg, 0.077 mmol), tri-tert-butylphosphine tetrafluoroboric acid (22 mg, 0.077 mmol), and methyldicyclohexylamine (0.123 mL, 0.581 mmol) in N-methyl-2-pyrrolidone (0.97 mL) was stirred at 100° C. for one hour under nitrogen atmosphere. The reaction mixture was cooled, quenched with water, and then extracted with ethyl acetate. The organic layer was washed with water and brine, dried over anhydrous sodium sulfate, and then concentrated under reduced pressure. The obtained residue was purified by silica gel column chromatography (ethyl acetate—hexane) to afford (E)-1-(3,5-dimethyl-4-(2-((4-oxo-2-(3-(trifluoromethyl)phenyl)-1,3,8-triazaspiro[4.5]deca-1-en-8-yl)sulfonyl)vinyl)phenyl)-5,5-dimethylimidazolidine-2,4-dione (197 mg, 82%).

MS(ESI) m/z=618 (M+H)+

(Reaction 2-2)

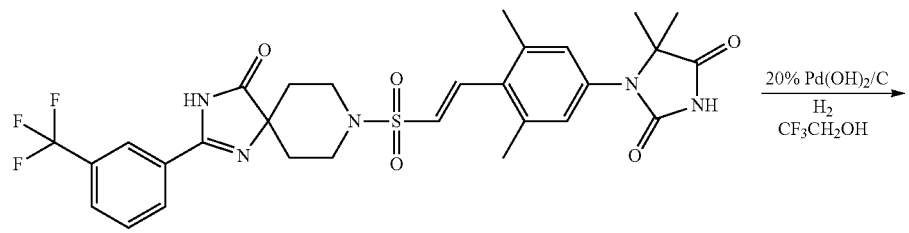

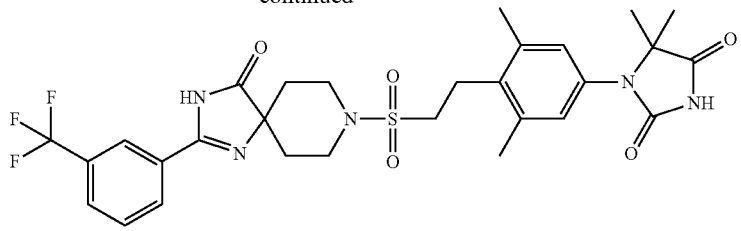

Compound 6

A mixture of (E)-1-(3,5-dimethyl-4-(2-((4-oxo-2-(3-(trifluoromethyl)phenyl)-1,3,8-triazaspiro[4.5]deca-1-en-8-yl)sulfonyl)vinyl)phenyl)-5,5-dimethylimidazolidine-2,4-dione (195 mg, 0.316 mmol) and palladium hydroxide/carbon (20% Pd) (wetted with approximately 50% water) (195 mg, 0.139 mmol) in 2,2,2-trifluoroethanol (6 mL) was stirred at room temperature for 14 hours under hydrogen atmosphere. The mixture was filtered, and the filtrate was concentrated under reduced pressure. The obtained residue was purified by silica gel column chromatography (ethyl acetate—hexane) to afford 1-(3,5-dimethyl-4-(2-((4-oxo-2-(3-(trifluoromethyl)phenyl)-1,3,8-triazaspiro[4.5]deca-1-en-8-yl)sulfonyl)ethyl)phenyl)-5,5-dimethylimidazolidine-2,4-dione (121 mg, 62%).

MS(ESI) m/z=620 (M+H)+. $^1$H-NMR (400 MHz, CD$_3$OD) δ: 1.40 (6H, s), 1.72-1.81 (2H, m), 2.00-2.10 (2H, m), 2.44 (6H, s), 3.22 (4H, s), 3.50-3.58 (2H, m), 3.80-3.88 (2H, m), 7.01 (2H, s), 7.72-7.79 (1H, m), 7.88-7.94 (1H, m), 8.16-8.23 (1H, m), 8.31 (1H, s)

Reference Example 3

1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-5,5-dimethylimidazolidine-2,4-dione (Compound 7)

(Reaction 3)

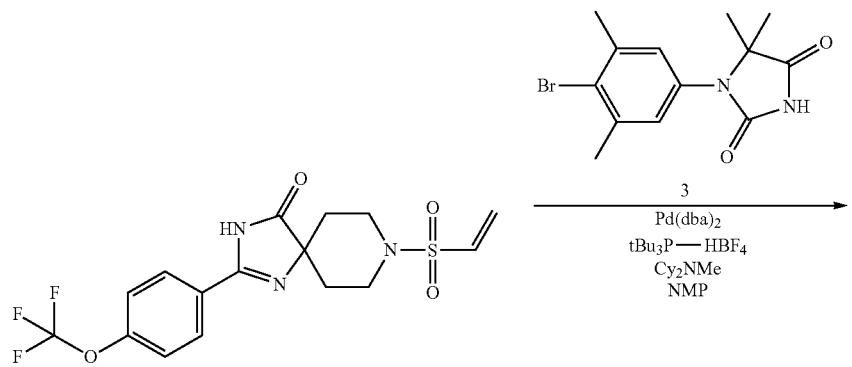

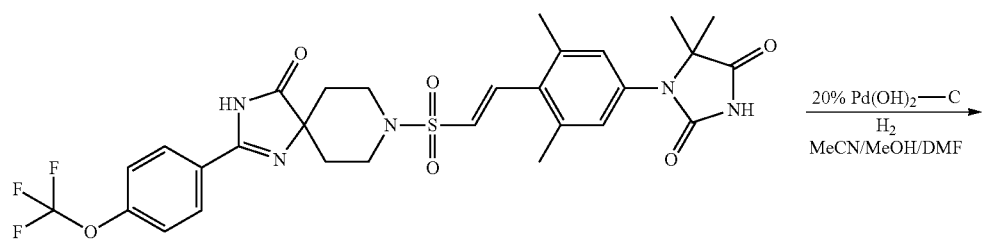

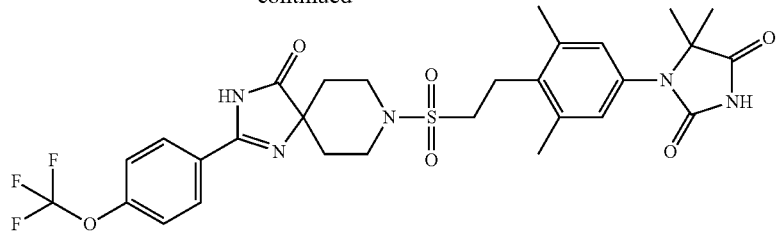

Compound 7

With the use of appropriate starting materials and solvents, 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-5,5-dimethylimidazolidine-2,4-dione (Compound 7) was synthesized by operations similar to those described in Reference Example 2.

MS(ESI) m/z=636 (M+H)+. $^1$H-NMR (400 MHz, CDCl$_3$) δ: 1.47 (6H, s), 1.70-1.78 (2H, m), 2.10-2.19 (2H, m), 2.40 (6H, s), 3.00-3.07 (2H, m), 3.19-3.25 (2H, m), 3.45-3.53 (2H, m), 3.81-3.88 (2H, m), 6.94 (2H, s), 7.35 (2H, d, J=8.0 Hz), 7.73 (1H, brs), 7.93 (2H, d, J=8.0 Hz), 9.37 (1H, brs)

Reference Example 4

1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-1,3-diazaspiro[4.4]nonane-2,4-dione (Compound 8)

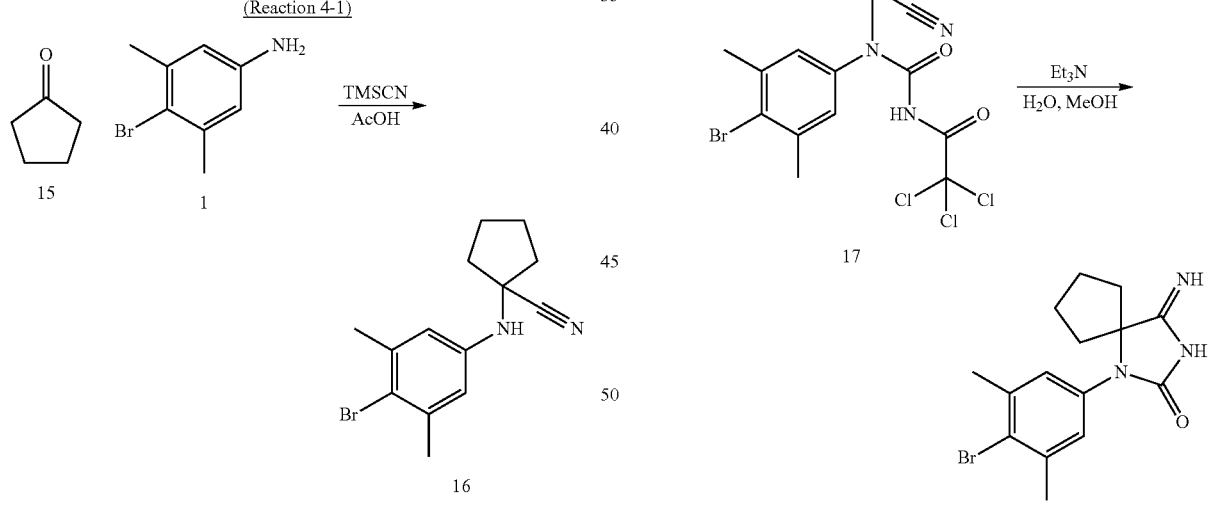

To a mixture of cyclopentanone (42 mg, 0.500 mmol) and 4-bromo-3,5-dimethylaniline (100 mg, 0.500 mmol) in acetic acid (0.5 mL), trimethylsilyl cyanide (0.063 ml, 0.500 mmol) was added at room temperature. The mixture was stirred at room temperature for 1.5 hours under nitrogen atmosphere. The reaction mixture was quenched with 28% aqueous ammonia (1 mL), diluted with water and extracted with dichloromethane. The organic layer was washed with water and brine, dried over anhydrous sodium sulfate, and then concentrated under reduced pressure to afford 1-((4-bromo-3,5-dimethylphenyl)amino)cyclopentanecarbonitrile as a crude product (152 mg).

$^1$H-NMR (400 MHz, CDCl$_3$) δ: 1.83-1.92 (4H, m), 2.07-2.15 (2H, m), 2.33-2.42 (2H, m), 2.37 (6H, m), 3.71 (1H, brs), 6.56 (2H, s)

To a solution of 1-((4-bromo-3,5-dimethylphenyl)amino)cyclopentanecarbonitrile (145 mg, 0.495 mmol) in dichloromethane (5 mL), 2,2,2-trichloroactylisocyanate (0.070 mL, 0.593 mmol) was added at room temperature. The mixture was stirred at room temperature for one hour under nitrogen atmosphere.

Triethylamine (0.103 mL, 0.742 mmol), water (0.045 mL), and methanol (0.10 mL) were added and the mixture was refluxed for 1.5 hours under nitrogen atmosphere. The reaction mixture was cooled, followed by dilution with water and adjustment of its pH to 5 using a 1 N aqueous hydrochloric acid solution, and then extracted with dichloromethane. The organic layer was washed with water and brine, dried over anhydrous sodium sulfate, and then concentrated under reduced pressure to afford 1-(4-bromo-3,5-dimethylphenyl)-4-imino-1,3-diazaspiro[4.4]nonan-2-one as a crude product.

MS(ESI) m/z=336, 338 (M+H)+

(Reaction 4-3)

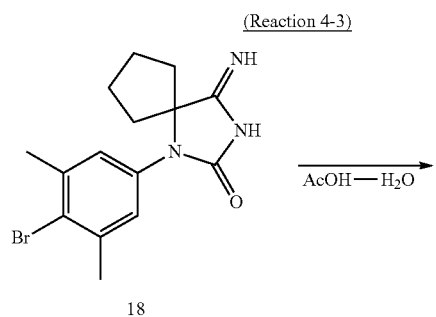

18

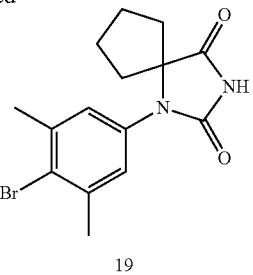

19

A mixture of 1-(4-bromo-3,5-dimethylphenyl)-4-imino-1,3-diazaspiro[4.4]nonan-2-one (the crude product obtained in the previous reaction) in acetic acid (1.0 mL) and water (0.25 mL) was stirred for 1.5 hours at 65° C. under nitrogen atmosphere. After further addition of acetic acid (1.0 mL) and water (0.25 mL), the mixture was stirred for 17 hours at 65° C. under nitrogen atmosphere. The reaction mixture was cooled, followed by dilution with water and adjustment of its pH to 8 using a saturated aqueous sodium hydrogen carbonate solution, and extracted with ethyl acetate. The organic layer was washed with water and brine, dried over anhydrous sodium sulfate, and then concentrated under reduced pressure. The residue was purified by silica gel column chromatography (ethyl acetate—hexane) to afford 1-(4-bromo-3,5-dimethylphenyl)-1,3-diazaspiro[4.4]nonane-2,4-dione (121 mg).

MS(ESI) m/z=337, 339 (M+H)+

(Reaction 4-4)

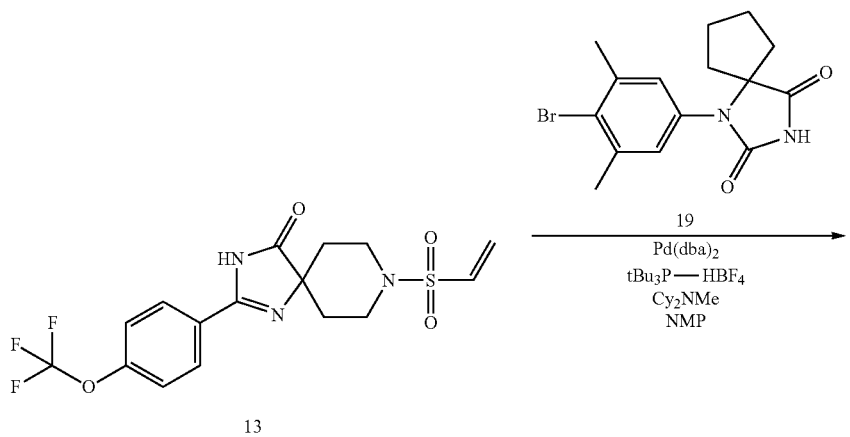

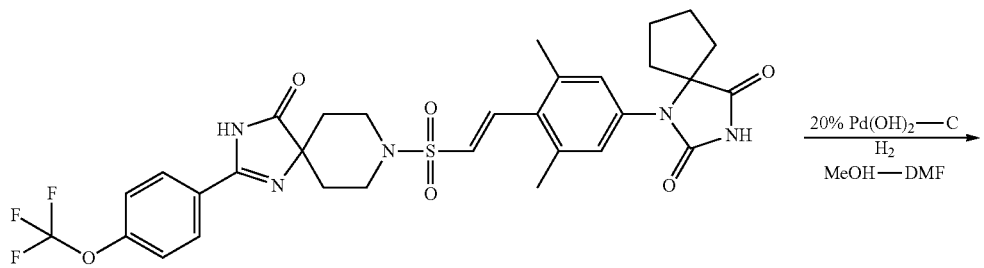

20

-continued

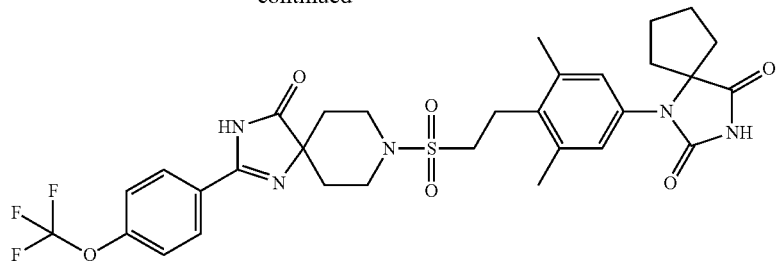

Compound 8

With the use of appropriate starting materials and solvents, 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-1,3-diazaspiro[4.4]nonane-2,4-dione (Compound 8) was obtained by operations similar to those described in Reference Example 2.

MS(ESI) m/z=662 (M+H)+. $^1$H-NMR (400 MHz, DMSO-$d_6$) δ: 1.36-1.44 (2H, m), 1.60-1.70 (4H. m), 1.82-1.91 (2H, m), 1.91-2.06 (4H, m), 2.38 (6H, s), 3.01-3.09 (2H, m), 3.22-3.30 (2H, m), 3.30-3.42 (2H, m), 3.70-3.77 (2H, m), 7.03 (2H, s), 7.57 (2H, d, J=8.4 Hz), 8.14 (2H, d, J=8.4 Hz)

Reference Example 5

1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-8-methyl-1,3,8-triazaspiro[4.5]decane-2,4-dione (Compound 9)

(Reaction 5-1)

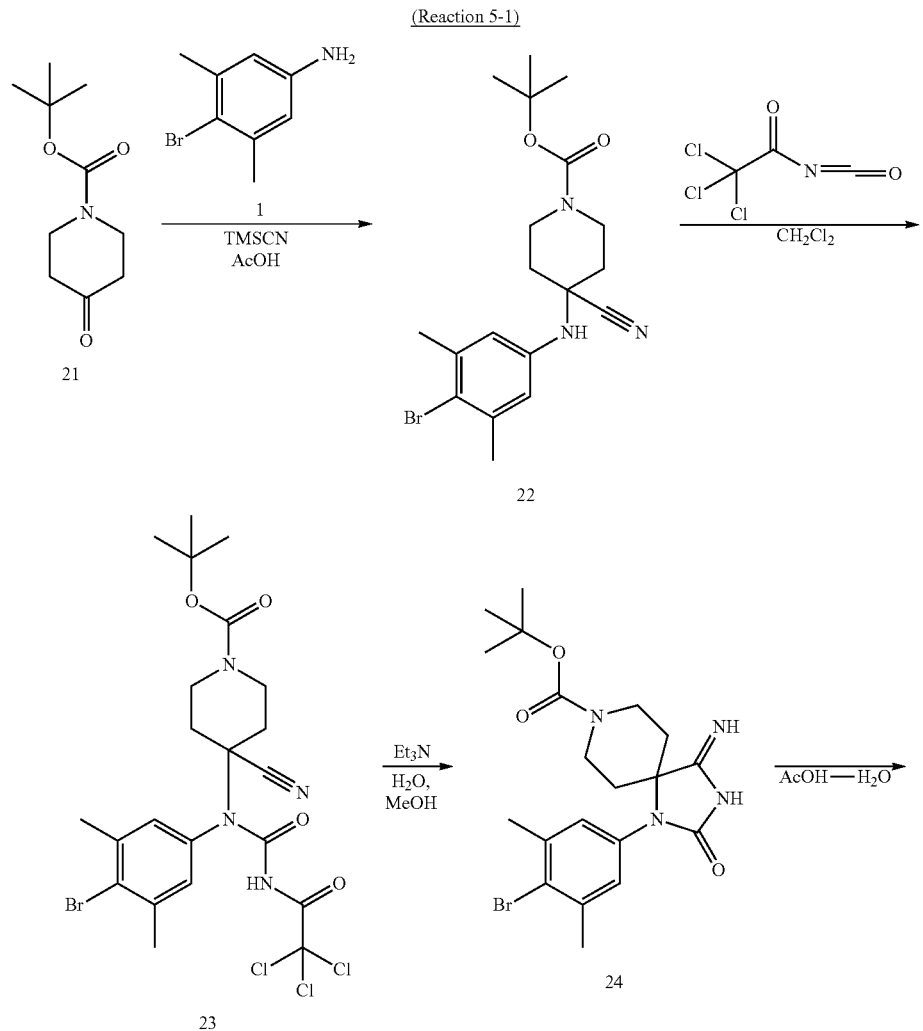

-continued

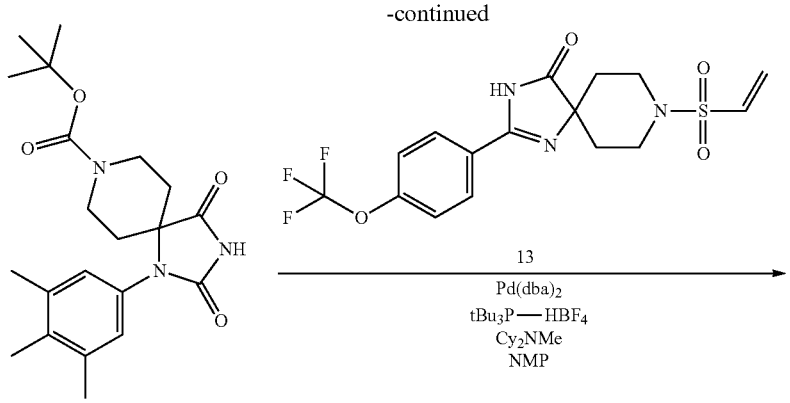

25

13
Pd(dba)₂
tBu₃P—HBF₄
Cy₂NMe
NMP
→

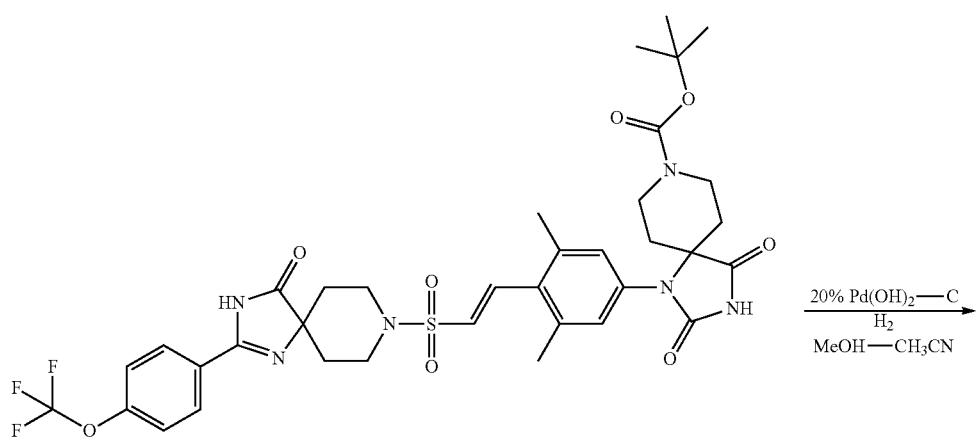

26

20% Pd(OH)₂—C
H₂
MeOH—CH₃CN
→

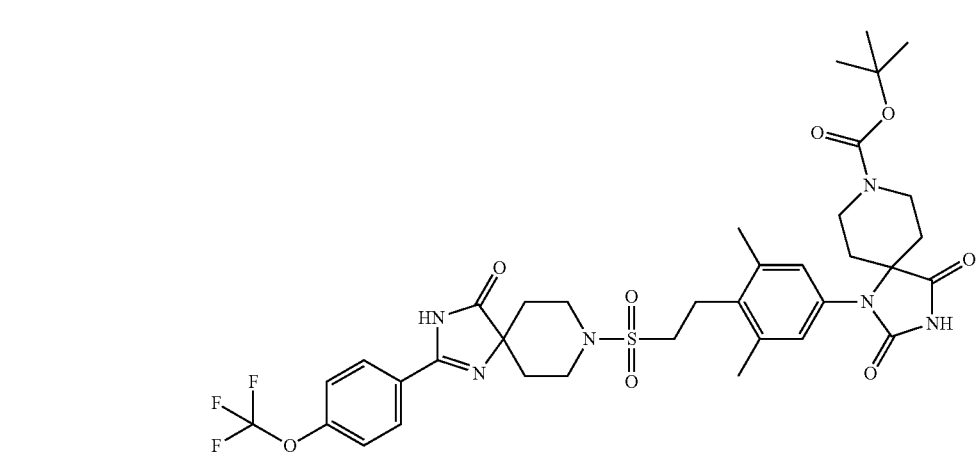

27

With the use of 4-oxopiperidine-1-carboxylic acid tert-butyl ester as a starting material, and the use of an appropriate solvent, 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-2,4-dioxo-1,3,8-triazaspiro[4.5]decan-8-carboxylic acid tert-butyl ester was obtained by operations similar to those described in Reference Example 4.

MS(ESI) m/z=777 (M+H)+.

(Reaction 5-2)

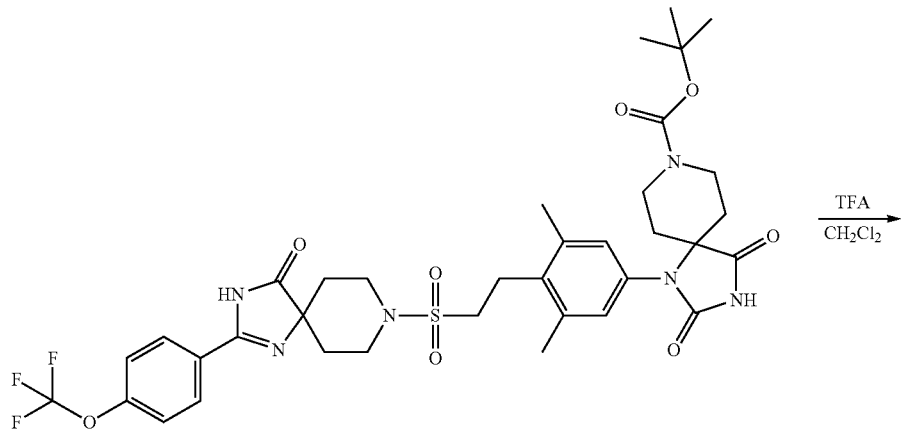

27

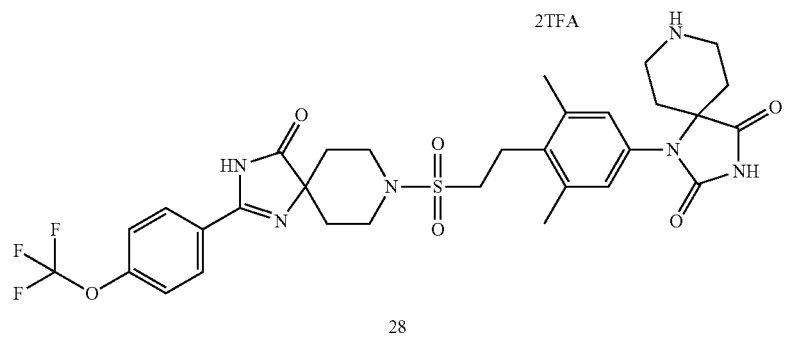

28

To a mixed solution of 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-2,4-dioxo-1,3,8-triazaspiro[4.5]decan-8-carboxylic acid tert-butyl ester (11.7 mg, 0.015 mmol) in dichloromethane (0.13 mL), trifluoroacetic acid (0.05 mL, 0.673 mmol) was added at room temperature. The mixture was placed under a stream of nitrogen, and stirred at room temperature for one hour. The reaction mixture was concentrated under reduced pressure to obtain 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-1,3,8-triazaspiro[4.5]decan-2,4-dione 2 trifluoroacetic acid salt (13.6 mg).

MS(ESI) m/z=677 (M+H)+.

(Reaction 5-3)

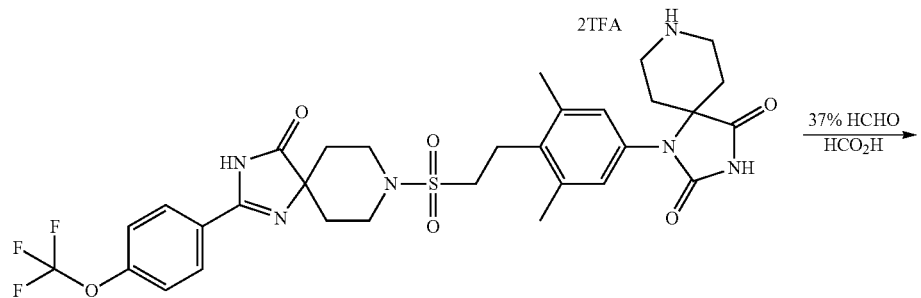

28

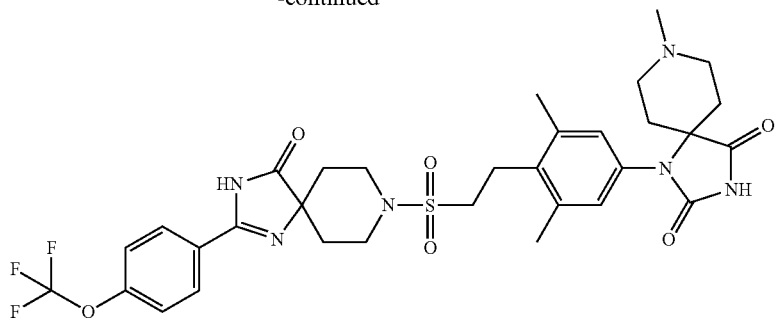

Compound 9

To a mixture of 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-1,3,8-triazaspiro[4.5]decan-2,4-dione 2 trifluoroacetic acid salt (21.1 mg, 0.022 mmol) and formic acid (0.033 mL), a 37% aqueous formaldehyde solution (0.055 mL) was added. The mixture was placed under a stream of nitrogen, and stirred for three hours while heating at 80° C. The reaction mixture was concentrated, and the resulting residue was diluted with ethyl acetate. The organic layer was washed with a diluted aqueous sodium hydroxide solution, dried over anhydrous magnesium sulfate, and then concentrated under reduced pressure. The obtained residue was subjected to column chromatography (dichloromethane—methanol) for purification to obtain 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl-8-methyl-1,3,8-triazaspiro[4.5]decane-2,4-dione (4.5 mg, 30%).

MS(ESI) m/z=691 (M+H)+. $^1$H-NMR (400 MHz, CD$_3$OD) δ: 1.76-1.84 (2H, m), 1.92-2.02 (2H, m), 2.02-2.12 (4H, m), 2.38 (3H, s), 2.46 (6H, s), 2.81-2.88 (2H, m), 2.92-3.02 (2H, m), 3.23 (4H, s), 3.51-3.60 (2H, m), 3.72-3.80 (2H, m), 7.01 (2H, s), 7.48 (2H, d, J=8.0 Hz), 8.10 (2H, d, J=8.0 Hz)

Reference Example 6

5-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-2-oxa-5,7-diazaspiro[3.4]octane-6,8-dione (Compound 10)

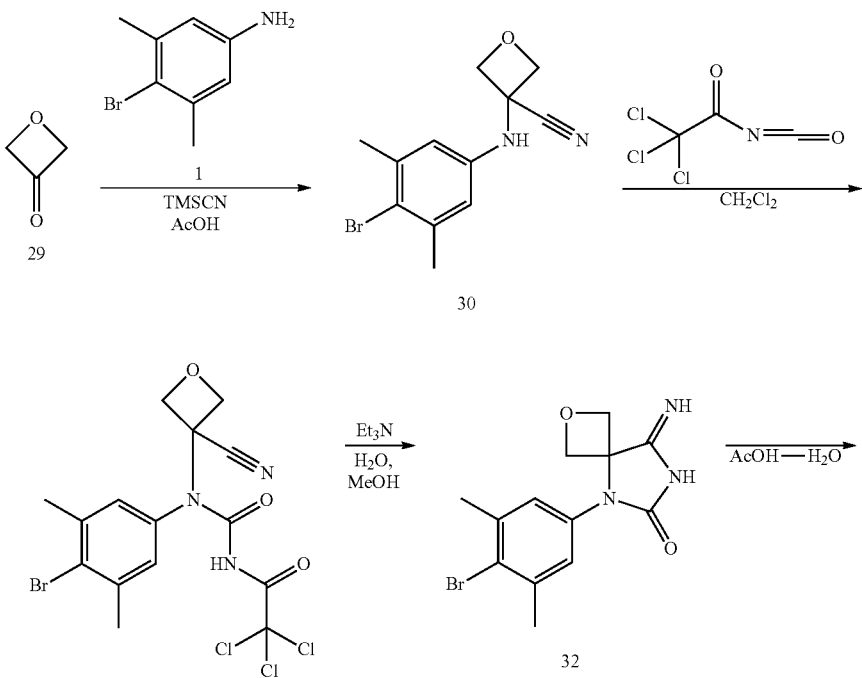

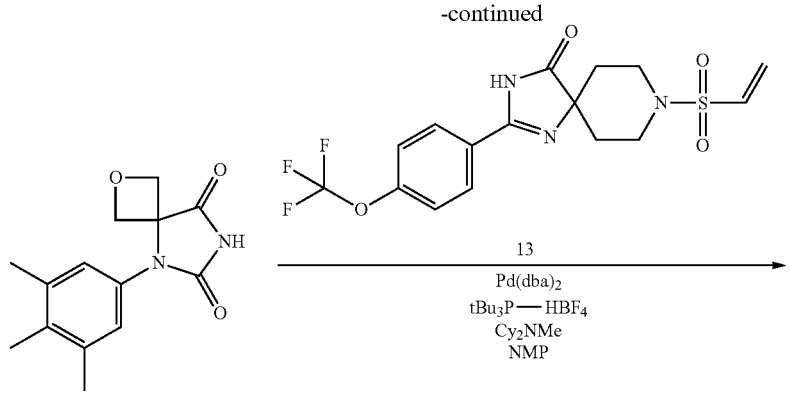

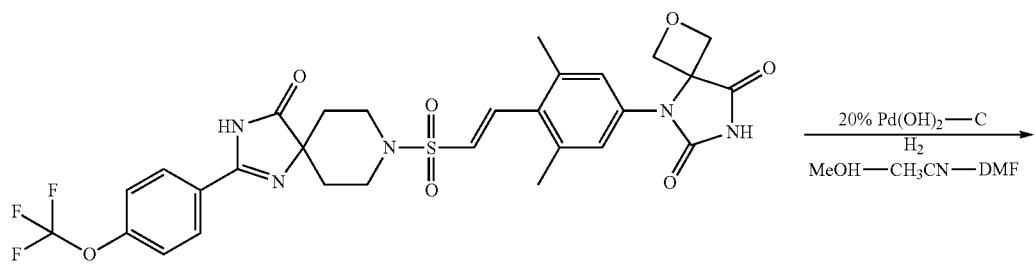

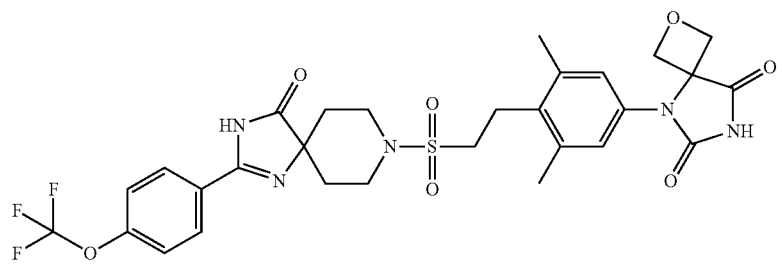

Compound 10

With the use of oxetane-3-one as a starting material, and the use of appropriate solvents, 5-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-2-oxa-5,7-diazaspiro[3.4]octane-6,8-dione was obtained by operations similar to those of Reference Example 4.

MS(ESI) m/z=650 (M+H)+. $^1$H-NMR (400 MHz, CDCl$_3$) δ: 1.69-1.77 (2H, m), 2.12-2.22 (2H, m), 2.45 (6H, s), 3.03-3.11 (2H, m), 3.22-3.29 (2H, m), 3.46-3.53 (2H, m), 3.84-3.91 (2H, m), 4.86 (2H, d, J=7.2 Hz), 5.03 (2H, d, J=7.2 Hz), 7.07 (2H, s), 7.35 (2H, d, J=8.4 Hz), 7.98 (2H, d, J=8.4 Hz), 8.56 (1H, s), 10.34 (1H, s)

Reference Example 7

4-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-4,6-diazaspiro[2.4]heptane-5,7-dione (Compound 11)

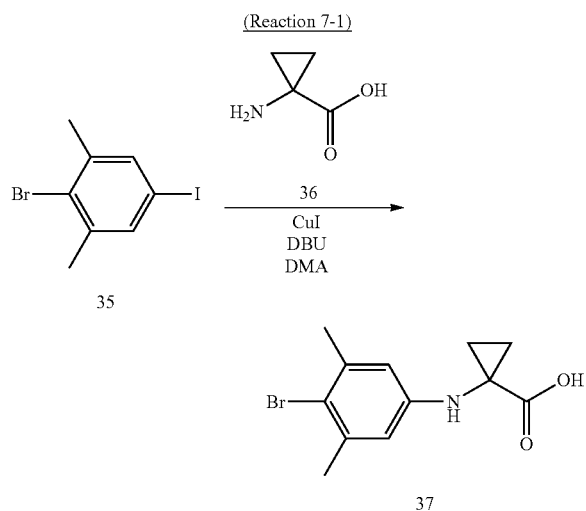

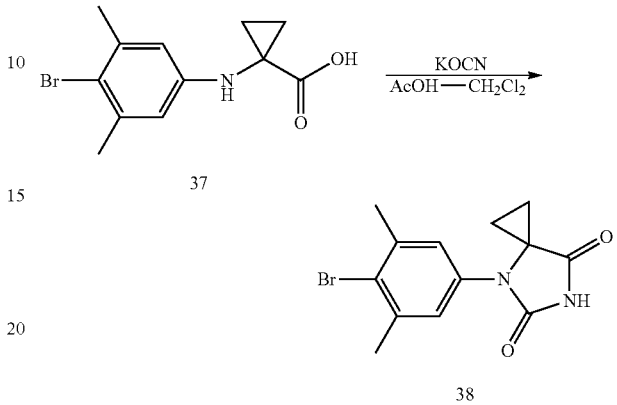

A mixture of 2-bromo-5-iodo-1,3-dimethylbenzene (300 mg, 0.965 mmol), 1-aminocyclopropane carboxylic acid (195 mg, 1.93 mmol), copper iodide (I) (37 mg, 0.194 mmol), and diazabicycloundecene (0.50 mL, 3.35 mmol) in dimethylacetamide (2.6 mL) was stirred at 120° C. for three hours under nitrogen atmosphere. The reaction mixture was purified by silica gel column chromatography (Wakosil C18, acetonitrile-water (0.1% formic acid)) to afford 1-((4-bromo-3,5-dimethylphenyl)amino)cyclopropane carboxylic acid (219 mg, 80%).

MS(ESI) m/z=284, 286 (M+H)+.

To a mixture of 1-((4-bromo-3,5-dimethylphenyl)amino) cyclopropane carboxylic acid (198 mg, 0.697 mmol) in acetic acid (3 mL) and dichloromethane (1.5 mL), potassium cyanate (424 mg, 5.23 mmol) was added at room temperature. The mixture was stirred at room temperature for one hour, and then stirred at 60° C. for two hours. A saturated aqueous sodium hydrogen carbonate solution was added to adjust pH to 8, and this mixture was extracted with ethyl acetate. The organic layer was washed with water and brine, dried over anhydrous sodium sulfate, and then concentrated under reduced pressure. The residue was purified by silica gel column chromatography (ethyl acetate—hexane) to afford 4-(4-bromo-3,5-dimethylphenyl)-4,6-diazaspiro[2.4] heptane-5,7-dione (49 mg, 23%).

MS(ESI) m/z=309, 311 (M+H)+.

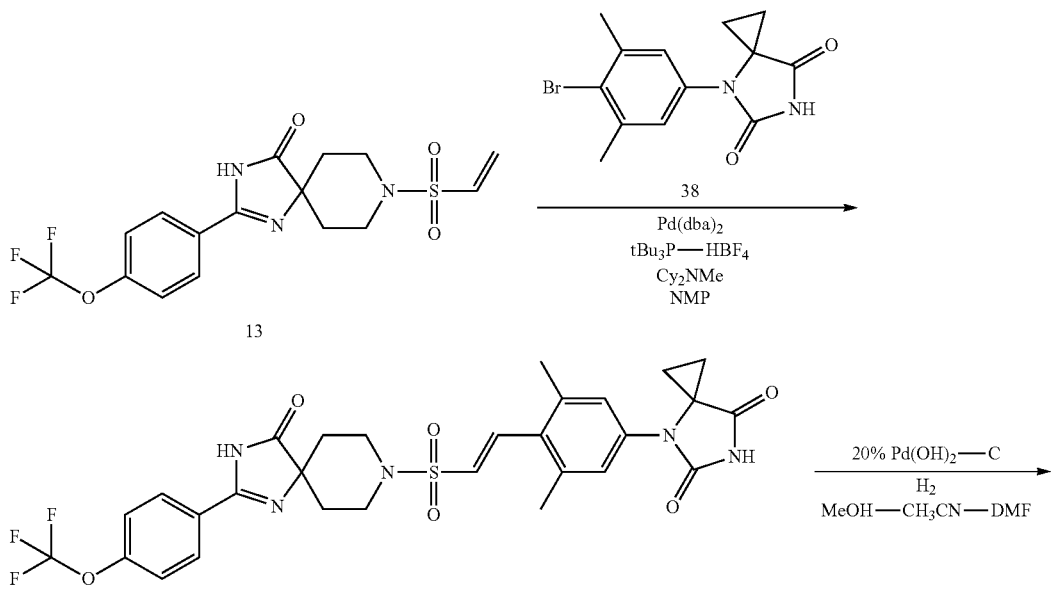

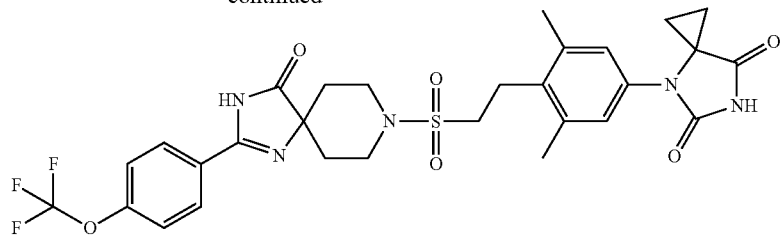

Compound 11

With the use of appropriate starting materials and solvents, 4-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-4,6-diazaspiro[2.4]heptane-5,7-dione (Compound 11) was obtained by operations similar to those of Reference Example 2.

MS(ESI) m/z=634 (M+H)+. $^1$H-NMR (400 MHz, DMSO-$d_6$) δ: 0.99-1.03 (2H, m), 1.19-1.27 (4H, m), 1.58-1.64 (2H, m), 1.81-1.90 (2H, m), 2.35 (6H, s), 2.99-3.04 (2H, m), 3.22-3.29 (2H, m), 3.67-3.73 (2H, m), 6.95 (2H, s), 7.56 (2H, d, J=8.4 Hz), 8.12 (2H, d, J=8.4 Hz)

Reference Example 8

1-(3,5-dimethyl-4-(2-((4-oxo-2-(3-(trifluoromethyl)phenyl)-1,3,8-triazaspiro[4.5]deca-1-en-8-yl) sulfonyl)ethyl)phenyl)-1,3-diazaspiro[4.4]nonane-2,4-dione (Compound 12)

(Reaction 8)

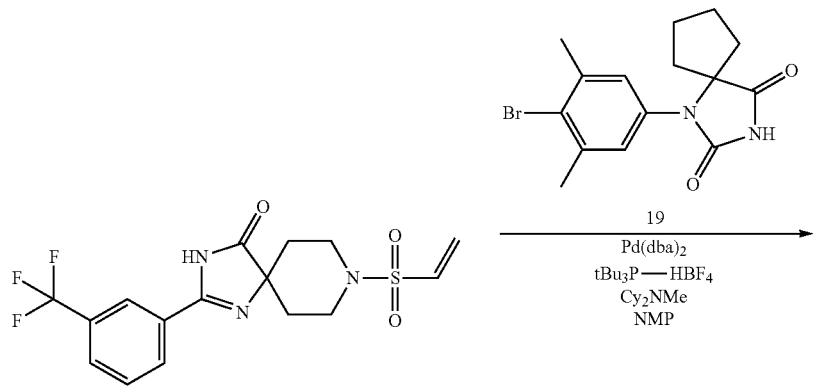

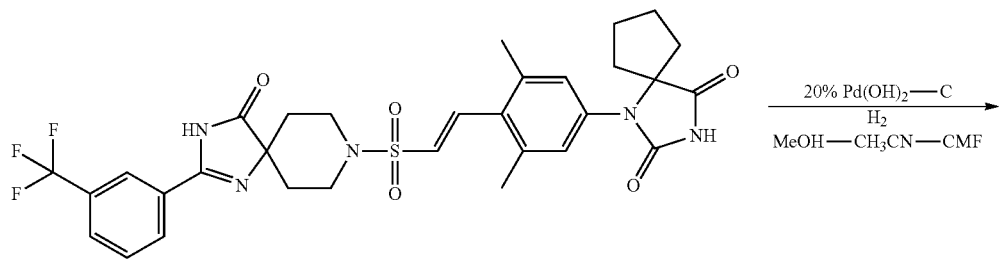

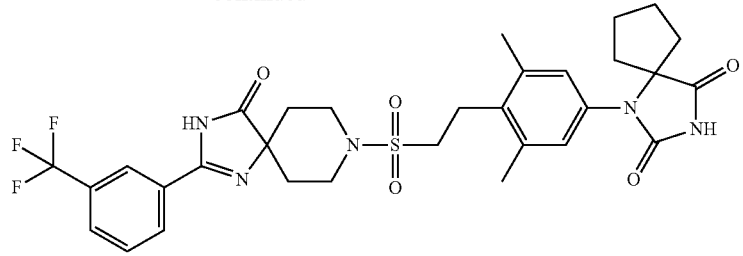

Compound 12

With the use of appropriate starting materials and solvents, 1-(3,5-dimethyl-4-(2-((4-oxo-2-(3-(trifluoromethyl)phenyl)-1,3,8-triazaspiro[4.5]deca-1-en-8-yl) sulfonyl)ethyl)phenyl)-1,3-diazaspiro[4.4]nonane-2,4-dione was obtained by operations similar to those of Reference Example 2.

MS(ESI) m/z=646 (M+H)+. $^1$H-NMR (400 MHz, DMSO-$d_6$) δ: 1.40-1.48 (2H, m), 1.62-1.71 (4H, m), 1.88-1.97 (2H, m), 1.97-2.08 (4H, m), 2.41 (6H, s), 3.03-3.10 (2H, m), 2.29-3.34 (2H, m), 3.38-3.47 (2H, m), 3.72-3.79 (2H, m), 7.06 (2H, s), 7.84 (1H, dd, J=7.6, 7.6 Hz), 8.02 (1H, d, J=7.6 Hz), 8.33 (1H, d, J=7.6 Hz), 8.38 (1H, s)

REFERENCE TEST EXAMPLES

For the compounds of the present invention, test results on the activity of cAMP production via the human PTH1R, activity of cAMP production via the rat PTH1R, metabolic stability using human liver microsomes, metabolic stability using rat hepatocyte, and calcemic action in TPTX rat models are shown in Reference Test Examples 1 to 5, respectively. Compounds described in WO2010/126030A1, which are shown in Table 3, were used as comparative compounds.

TABLE 3

| Comparative Example | Structural formula |
|---|---|
| Comparative Example 1<br>WO2010/126030A1<br>Compound 792 | 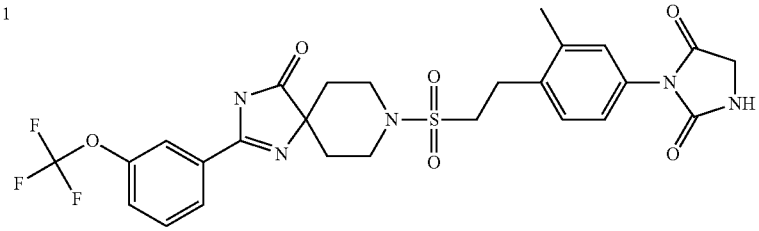 |
| Comparative Example 2<br>WO2010/126030A1<br>Compound 799 | 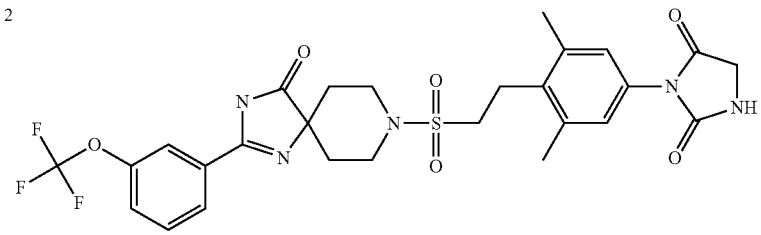 |
| Comparative Example 3<br>WO2010/126030A1<br>Compound 800 | 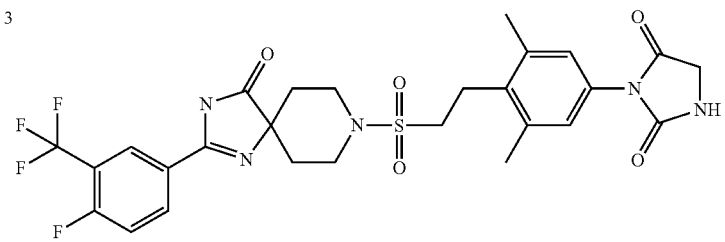 |

TABLE 3-continued

| Comparative Example | Structural formula |
| --- | --- |
| Comparative Example 4<br>WO2010/126030A1<br>Compound 878 | 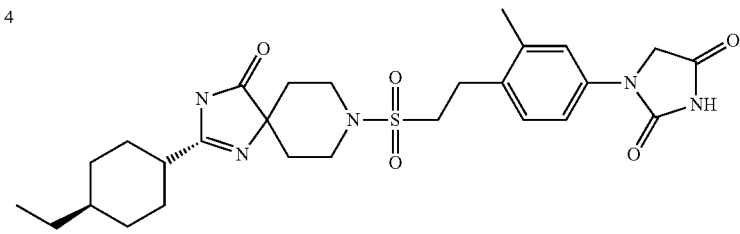 |
| Comparative Example 5<br>WO2010/126030A1<br>Compound 879 | 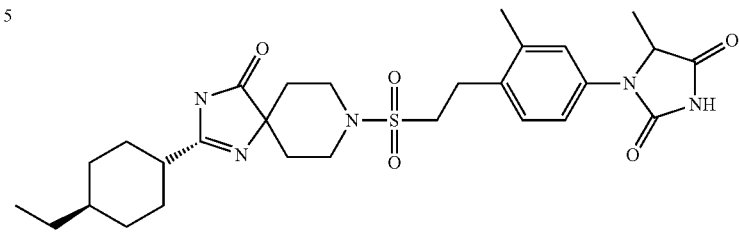 |
| Comparative Example 6<br>WO2010/126030A1<br>Compound 887 | 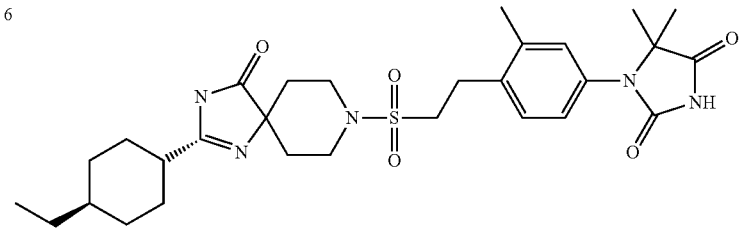 |

Reference Test Example 1

Measurement of In Vitro cAMP Signal Activity of Compounds Via the Human PTH (Peptides)

Human PTH(1-34) and calcitonin were purchased from Peptide Institute, Inc. (Osaka, Japan), dissolved in 10 mM acetic acid to 1 mM and stored in a −80° C. freezer.

(Cell Culture)

Cells were cultured in Dulbecco's modified Eagle's medium (DMEM) supplemented with 10% fetal bovine serum (Hyclone), 100 units/ml penicillin G and 100 μg/ml streptomycin sulfate (Invitrogen Corp) at 37° C. in a humidified atmosphere containing 5% $CO_2$.

cAMP signal transduction analysis utilized LLC-PK1 cells not expressing the PTH1R, and HKRK-B7 cells, that is, LLC-PK1 cells overexpressing the human PTH1R at 9.5× $10^5$ receptors/cell (Takasu et al., J. Bone. Miner. Res. 14:11-20, 1999).

(cAMP Stimulation)

HKRK-B7 or LLC-PK1 cells were seeded into a 96-well plate at 1×$10^5$ cells/well and incubated overnight. On the following day, 50 μl of cAMP assay buffer (DMEM, 2 mM IBMX, 0.2 mg/ml bovine serum albumin, 35 mM Hepes-NaOH, pH 7.4) containing human PTH(1-34) or each compound was added and the plate was placed in a 37° C. incubator. The cells were incubated for 20 minutes. After removing the medium, the cells were washed with 100 μl of cAMP assay buffer once. The plate was placed on dry ice powder to freeze the cells and then removed from the dry ice. The cells were lysed with 40 μl of 50 mM HCl and frozen again on dry ice. The amount of intracellular cAMP produced was measured using a commercially available cAMP EIA kit (Biotrack cAMP EIA system, GE health care).

(Calculation of 20% Effective Concentration (EC20) and 50% Effective Concentration (EC50) in the Measurement of In Vitro cAMP-Inducing Ability)

Analyses were performed using a variable gradient S-shaped dose-response curve equation. The cAMP signaling activity of human PTH(1-34) at 100 nM was defined as 100%, and the concentration at which each compound shows 20% or 50% cAMP signaling activity was calculated as EC20 or EC50.

The results obtained with HKRK-B7 cells are shown in Table 4.

The degree of cAMP response in LLC-PK1 cells was lower than the degree in HKRK-B7 cells.

TABLE 4

| Compound | EC20 (μM) | EC50 (μM) |
| --- | --- | --- |
| Compound 1 | 1.3 | 5.8 |
| Compound 2 | 2.4 | 14 |
| Compound 3 | 1.5 | 7.2 |
| Compound 4 | 1.6 | 7.4 |
| Compound 5 | 1.7 | 8.1 |
| Compound 6 | 2.0 | 9.0 |
| Compound 7 | 1.1 | 4.1 |
| Compound 8 | 1.0 | 3.6 |
| Compound 9 | 2.6 | 12 |
| Compound 10 | 5.0 | 21 |

TABLE 4-continued

| Compound | EC20 (μM) | EC50 (μM) |
|---|---|---|
| Compound 11 | 1.5 | 11 |
| Comparative Example 1 | 1.5 | 4.8 |
| Comparative Example 2 | 3.1 | 13 |
| Comparative Example 3 | 2.0 | 9.0 |
| Comparative Example 4 | >505 | >1000 |
| Comparative Example 5 | 3.1 | 25 |
| Comparative Example 6 | 3.6 | 32 |

Reference Test Example 2

Measurement of the Compounds' In Vitro cAMP Signaling Activity Via the Rat PTH1R Instead of HKRK-B7 cells, LLC-PK46_RATO_PTH1R cells overexpressing rat PTH1R, which were established at Chugai Pharmaceutical, were used to take measurements in a similar manner to Reference Test Example 1.

The results obtained by using LLC-PK46_RATO_PTH1R cells are shown in Table 5.

The EC20 values of in vitro cAMP signaling activity of the rat PTH1 receptor had a good correlation with those of human PTH1R. A good correlation between rat and human was also seen for the EC50 values.

TABLE 5

| Compound | EC20 (μM) | EC50 (μM) |
|---|---|---|
| Compound 7 | 0.5 | 2.4 |
| Compound 8 | 0.4 | 1.9 |
| Compound 10 | 3.0 | 12 |
| Compound 11 | 0.8 | 3.2 |
| Comparative Example 1 | 0.8 | 2.3 |

Reference Test Example 3

Examination of Metabolic Stability Using Human Liver Microsomes

In 0.1 M phosphate buffer (pH7.4), human liver microsomes were incubated with a compound or a comparative example in the coexistence of NADPH at 37° C. for a specified amount of time. The concentration of the parent compound at each reaction time was measured using LC/MS/MS, and inherent clearance (μL/min/mg protein) was calculated from the slope of the reaction time versus residual rate.

<Assay Conditions>
Compound concentration: 1 μM
Microsome: 0.5 mg/mL
NADPH: 1 mM
Reaction time: 0, 5, 15, and 30 minutes The results are shown in Table 6. Compounds 1 to 11 showed high metabolic stability against human liver microsomes in comparison to Comparative Examples 1 to 6.

TABLE 6

| Compound | Clearance (μl/min/mg) |
|---|---|
| Compound 1 | 21 |
| Compound 2 | 38 |
| Compound 3 | 29 |
| Compound 4 | 27 |
| Compound 5 | 37 |
| Compound 6 | 29 |
| Compound 7 | 30 |
| Compound 8 | 35 |
| Compound 9 | 28 |
| Compound 10 | 29 |
| Compound 11 | 19 |
| Compound 12 | 63 |
| Comparative Example 1 | 84 |
| Comparative Example 2 | 61 |
| Comparative Example 3 | 74 |
| Comparative Example 4 | 74 |
| Comparative Example 5 | 112 |
| Comparative Example 6 | 154 |

Reference Test Example 4

Examination of Metabolic Stability Using Rat Hepatocyte

Liver cells were prepared from the liver of rats (SD, female) by a collagenase perfusion method. A compound of the Reference Examples or a Comparative Example was added, and this was incubated at 37° C. for a specified amount of time, followed by addition of a reaction-stopping solution. The concentration of the parent compound at each reaction time was measured using LC/MS/MS, and inherent clearance (μL/$10^6$ cells/min) was calculated from the slope of the reaction time versus residual rate.

<Assay Conditions>
Cell concentration: 1×$10^6$ cells/mL
Compound concentration: 1 μM
Medium: Williams' medium E
Reaction time: 0, 15, 30, 60, 120, and 240 minutes
Reaction-stopping solution: acetonitrile/2-propanol (4/6, v/v)

The results are shown in Table 7. The rat hepatocyte metabolic stability of Compounds 2, 4, 5, 6, 7, 8, 9, 10, and 11 increased compared to Comparative Examples 1, 2, 3, 5, and 6.

TABLE 7

| Compound | Clearance (μL/$10^6$ cells/min) |
|---|---|
| Compound 1 | 7.6 |
| Compound 2 | 3.0 |
| Compound 3 | 17 |
| Compound 4 | 2.2 |
| Compound 5 | 1.0 |
| Compound 6 | 1.4 |
| Compound 7 | 0.9 |
| Compound 8 | 3.0 |
| Compound 9 | 1.8 |
| Compound 10 | 0.3 |
| Compound 11 | −0.6 |
| Comparative | 5.8 |

TABLE 7-continued

| Compound | Clearance (μL/10⁶ cells/min) |
| --- | --- |
| Example 1 | |
| Comparative Example 2 | 5.9 |
| Comparative Example 3 | 22 |
| Comparative Example 5 | 22 |
| Comparative Example 6 | 22 |

Reference Test Example 5

Calcemic Action in the TPTX Rat Model

Four-week old female Crl:CD(SD) rats were obtained from Charles River Japan (Atsugi Breeding Center), and were acclimated to standard laboratory conditions of 20-26° C. and 35-75% humidity for one week. The rats were given tap water and were fed ad libitum with standard rodent chow (CE-2) (CLEA Japan, Inc.) containing 1.1% calcium, 1.0% phosphoric acid, and 250 IU/100 g of vitamin D3.

TPTX was performed on five-week old rats. Some of the individuals were subjected to sham operation (Sham). Individuals whose serum Ca concentration was less than 8 mg/dL on four days after the operation were selected for use as TPTX rats. On five days after the operation, the rats were assigned to eight TPTX groups and one Sham group (n=5, each group) based on their body weight and serum Ca concentration measured on four days after the operation. The solvent alone was orally administered to the Sham group and the TPTX-Vehicle group at a volume of 10 mL/kg. Each test article was orally administered individually to each TPTX test article group by dissolving it in a solvent at a dose of 30 mg/10 mL/kg. The solvent composition was 10% dimethylsulfoxide (Wako Pure Chemical Industries, Ltd.), 10% Cremophor EL (Sigma-Aldrich Japan LLC), 20% hydroxypropyl-β-cyclodextrin (Nihon Shokuhin Kako Co., Ltd.), glycine (Wako Pure Chemical Industries, Ltd.); and the pH was adjusted to 10. Immediately before administration of each sample, Pre-blood collection was performed, and blood collection was carried out at 2, 6, 10, and 24 hours after administration to measure the serum Ca concentration. Each blood collection was carried out from the jugular vein under isoflurane inhalation anesthesia.

Serum Ca measurement: Serum obtained by centrifugation from the collected blood was measured by using an automatic analyzer TBA-120FR (Toshiba Medical Systems Corporation).

For statistical analysis of the animal studies, data are shown as mean±standard error (SE). Statistical analysis were performed by unpaired test of the SAS Preclinical Package (Ver. 5.00.010720, SAS Institute Japan, Tokyo, Japan). A p-value of <0.05 was regarded as statistically significant. Statistically significant of each test article group comparing to the TPTX-Vehicle group, the Comparative Example 1 group, and the Comparative Example 2 group was shown as #, *, and ∫ respectively.

Figure 9:
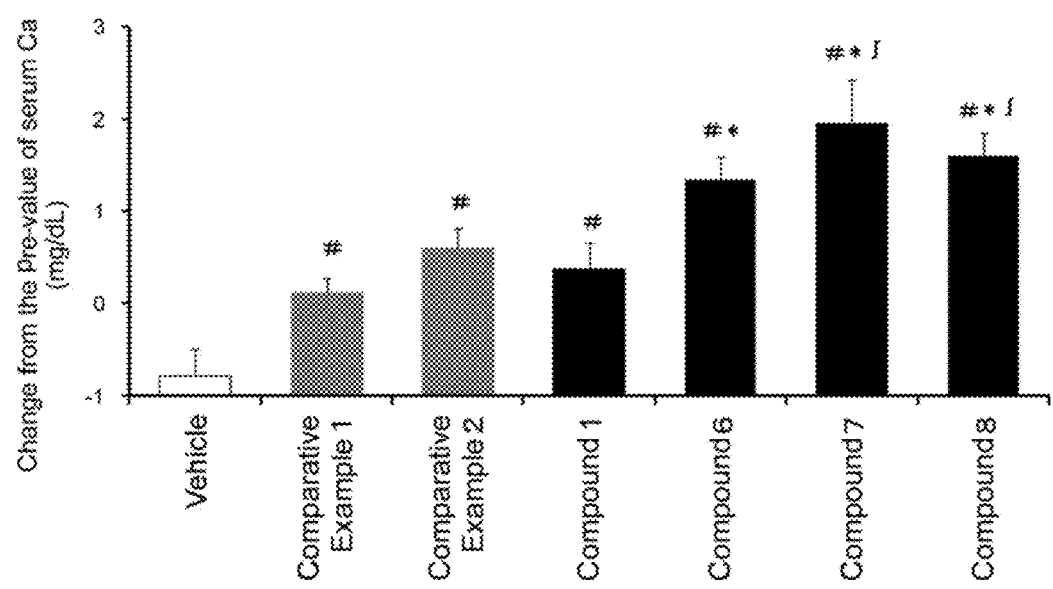
FIG. 9 shows the level of average change in serum Ca concentration up to 24 hours after oral administration of each compound at a dose of 30 mg/kg to TPTX rat models.

The Pre-value for the serum Ca concentration was 9.9 mg/dL for the Sham group, and 5.3-6.2 mg/dL for each of the TPTX groups. The serum Ca concentrations for each compound up to 24 hours after administration are shown in FIG. 9 as the average amount of change from the Pre-value. Furthermore, for all of the compounds, the serum Ca concentration peaked at six hours after administration or ten hours after administration of each compound.

Compounds 6, 7, and 8 which have high rat hepatocyte metabolic stability showed large positive changes from the Pre-value, and their oral administration showed strong effects on calcemic action. On the other hand, Compound 1, and Comparative Examples 1 and 2 which have low rat hepatocyte metabolic stability showed smaller positive changes from the Pre-value compared to Compounds 6, 7, and 8. In particular, Compounds 7 and 8 were statistically significant compared to Comparative Examples 1 and 2.

Furthermore, Compounds 6, 7, and 8 which have high rat hepatocyte metabolic stability showed individual maximum values of 7.8 to 8.5 mg/dL at six or ten hours after administration, and achieved the therapeutic target range of serum Ca concentration of 7.6 to 8.8 mg/dL in hypoparathyroidism patients. On the other hand, this therapeutic target range could not be achieved at any of the measurement times for Compound 1, and Comparative Examples 1 and 2 which have low rat hepatocyte metabolic stability.

From the above-mentioned test results, Compounds 6, 7, and 8, which have strong cAMP-signaling activities in cells forced to express rat PTH1R and high stability against metabolic breakdown in rat hepatocytes were found to show strong effects on calcemic action in rats when administered orally. These compounds also have cAMP-signaling activity in cells forced to express human PTH1R and high metabolic stability against human liver microsomes compared to the Comparative Compounds; and they are expected to have high therapeutic effects when administered orally to hypoparathyroidism patients. Furthermore, compounds represented by Formula (1), which have cAMP-signaling activity in cells forced to express human PTH1R and show metabolic stability against human liver microsomes to the same degree as Compounds 6, 7, and 8, are also expected to have high therapeutic effects in hypoparathyroidism patients.

INDUSTRIAL APPLICABILITY

The present invention provides pharmaceuticals for preventing, treating, and facilitating recovery and cure of osteoporosis, decrease of bone mass in periodontal disease, alveolar bone defect after tooth extraction, osteoarthritis, articular cartilage deficiency, adynamic bone disease, achondroplasia, hypochondroplasia, osteomalacia, bone fracture, and such, which induce bone/cartilage anabolism by non-invasive systemic exposure or local exposure to hydantoin derivatives that have high metabolic stability and exhibit strong PTH-like effects.

The invention claimed is:

1. A pharmaceutical composition for inducing bone and/or cartilage anabolism, which comprises as an active ingredient a compound represented by general formula (1) below or a pharmacologically acceptable salt thereof:

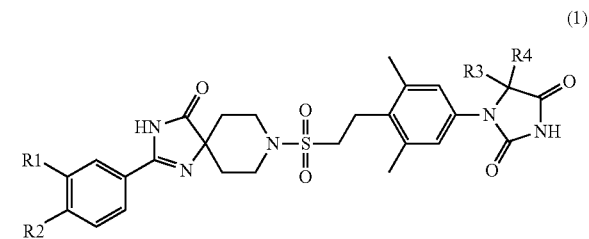

wherein
A) R1 and R2 are independently:
1) hydrogen atom;
2) halogen atom;
3) an alkyl group comprising one or two carbons that may be substituted with one to five fluorine atoms; or
4) an alkoxy group comprising one or two carbons that may be substituted with one to five fluorine atoms, provided that R1 and R2 are not both hydrogen atoms; or
B) R1 and R2 bond with each other to form a group represented by the formula below:

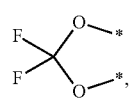

wherein each * indicates the position of bonding with the phenyl portion; and wherein
a) R3 and R4 are independently a methyl group that may be substituted with one to three fluorine atoms; or
b) R3 and R4, together with a bound carbon atom, form a three- to six-membered carbocyclic ring, wherein, one of the carbon atoms forming the ring may be replaced with an oxygen atom, a sulfur atom, or a methyl-substituted or unsubstituted nitrogen atom.

2. The pharmaceutical composition of claim 1, wherein R1 and R2 of the compound represented by said general formula (1) or a pharmacologically acceptable salt thereof are selected from the combinations below:
1) R1 is a hydrogen atom or a halogen atom, and R2 is a hydrogen atom, a trifluoromethyl group, or a trifluoromethoxy group, provided that R1 and R2 are not both hydrogen atoms);
2) R1 is a trifluoromethyl group or a trifluoromethoxy group, and R2 is a hydrogen atom or a halogen atom;
3) R1 and R2 bond with each other to form a group represented by the formula below:

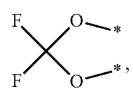

wherein, each * indicates the position of bonding with the phenyl portion; and
R3 and R4 are methyl groups; or
R3 and R4, together with a bound carbon atom, form a ring selected from below:

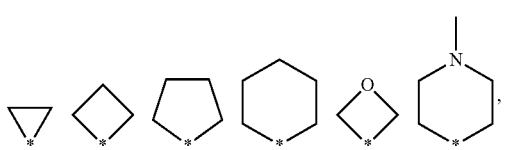

wherein * indicates the position of bonding with the imidazolidine-2,4-dione portion.

3. The pharmaceutical composition of claim 1, wherein R1 and R2 of the compound represented by said general formula (1) or a pharmacologically acceptable salt thereof are selected from the combinations below:

1) R1 is a trifuloromethoxy group and R2 is a fluorine atom;
2) R1 is a bromine atom and R2 is a hydrogen atom;
3) R1 is a trifuloromethoxy group and R2 is a fluorine atom;
4) R1 is a fluorine atom and R2 is a trifluoromethoxy group;
5) R1 is a trifluoromethyl group and R2 is a hydrogen atom;
6) R1 is a hydrogen atom and R2 is a trifluoromethoxy group;
7) R1 and R2 bond with each other to form a group represented by the formula below:

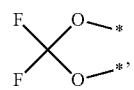

wherein each * indicates the position of bonding with the phenyl portion; and
R3 and R4 are methyl groups; or
R3 and R4, together with a bound carbon atom, form a ring selected from below:

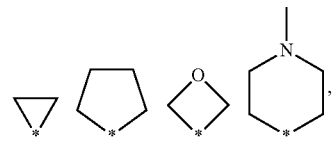

wherein * indicates the position of bonding with the imidazolidine-2,4-dione portion.

4. The pharmaceutical composition of claim 1, wherein R3 and R4 of the compound represented by said general formula (1) or a pharmacologically acceptable salt thereof are methyl groups.

5. The pharmaceutical composition of claim 1, wherein R3 and R4 of the compound represented by said general formula (1) or a pharmacologically acceptable salt thereof, together with a bound carbon atom, form a ring selected from below:

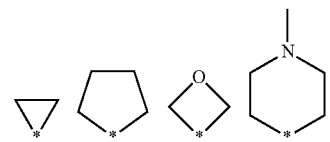

wherein * indicates the position of bonding with the imidazolidine-2,4-dione portion.

6. The pharmaceutical composition of claim 1, which comprises as an active ingredient a compound or pharmacologically acceptable salt thereof, wherein the compound is selected from the group consisting of:
1-(4-(2-((2-(4-fluoro-3-(trifluoromethoxy)phenyl)-4-oxo-1,3,8-triazaspiro[4.5]deca-1-en-8-yl)sulfonyl)ethyl)-3,5-dimethylphenyl)-5,5-dimethylimidazolidine-2,4-dione;
1-(4-(2-((2-(3-bromophenyl)-4-oxo-1,3,8-triazaspiro[4.5]deca-1-en-8-yl)sulfonyl)ethyl)-3,5-dimethylphenyl)-5,5-dimethylimidazolidine-2,4-dione;

1-(4-(2-((2-(4-fluoro-3-(trifluoromethyl)phenyl)-4-oxo-1,3,8-triazaspiro[4.5]deca-1-en-8-yl)sulfonyl)ethyl)-3,5-dimethylphenyl)-5,5-dimethylimidazolidine-2,4-dione;

1-(4-(2-((2-(3-fluoro-4-(trifluoromethoxy)phenyl)-4-oxo-1,3,8-triazaspiro[4.5]deca-1-en-8-yl)sulfonyl)ethyl)-3,5-dimethylphenyl)-5,5-dimethylimidazolidine-2,4-dione;

1-(4-(2-((2-(2,2-difluorobenzo[d][1,3]dioxol-5-yl)-4-oxo-1,3,8-triazaspiro[4.5]deca-1-en-8-yl)sulfonyl)ethyl)-3,5-dimethylphenyl)-5,5-dimethylimidazolidine-2,4-dione;

1-(3,5-dimethyl-4-(2-((4-oxo-2-(3-(trifluoromethyl)phenyl)-1,3,8-triazaspiro[4.5]deca-1-en-8-yl)sulfonyl)ethyl)phenyl)-5,5-dimethylimidazolidine-2,4-dione;

1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-5,5-dimethylimidazolidine-2,4-dione);

1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-1,3-diazaspiro[4.4]nonane-2,4-dione;

1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-8-methyl-1,3,8-triazaspiro[4.5]decane-2,4-dione;

5-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-2-oxa-5,7-diazaspiro[3.4]octane-6,8-dione; and 4-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-4,6-diazaspiro[2.4]heptane-5,7-dione.

7. The pharmaceutical composition of claim 1, wherein the compound is 1-(3,5-dimethyl-4-(2-((4-oxo-2-(3-(trifluoromethyl)phenyl)-1,3,8-triazaspiro[4.5]deca-1-en-8-yl)sulfonyl)ethyl)phenyl)-5,5-dimethylimidazolidine-2,4-dione or a pharmacologically acceptable salt thereof.

8. The pharmaceutical composition of claim 1, wherein the compound is 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-5,5-dimethylimidazolidine-2,4-dione or a pharmacologically acceptable salt thereof.

9. The pharmaceutical composition of claim 1, wherein the compound is 1-(3,5-dimethyl-4-(2-((4-oxo-2-(4-(trifluoromethoxy)phenyl)-1,3,8-triazaspiro[4.5]deca-1-en-8-yl)sulfonyl)ethyl)phenyl)-1,3-diazaspiro[4.4]nonane-2,4-dione or a pharmacologically acceptable salt thereof.

10. A method for inducing bone and/or cartilage anabolism, which comprises administering a compound of claim 1 or a pharmaceutically acceptable salt thereof in a pharmaceutically effective amount to a patient in need of prevention or treatment of osteoporosis, improvement of decrease of bone mass in periodontal disease, facilitation of recovery from alveolar bone defect after tooth extraction, prevention or treatment of osteoarthritis, facilitation of recovery from articular cartilage deficiency, prevention or treatment of adynamic bone disease, prevention or treatment of achondroplasia, prevention or treatment of hypochondroplasia, prevention or treatment of osteomalacia, or facilitation of recovery from bone fracture.

11. The method of claim 10, wherein the method for inducing bone and/or cartilage anabolism is a method for preventing or treating osteoporosis, a method for improving decrease of bone mass in periodontal disease, a method for facilitating recovery from alveolar bone defect after tooth extraction, a method for preventing or treating osteoarthritis, a method for promoting recovery from articular cartilage deficiency, a method for preventing or treating adynamic bone disease, a method for preventing or treating achondroplasia, a method for preventing or treating hypochondroplasia, a method for preventing or treating osteomalacia, or a method for facilitating recovery from bone fracture.

* * * * *